(12) United States Patent
Weigl et al.

(10) Patent No.: US 6,454,945 B1
(45) Date of Patent: Sep. 24, 2002

(54) MICROFABRICATED DEVICES AND METHODS

(75) Inventors: Bernhard H. Weigl; Paul Yager, both of Seattle, WA (US); James P. Brody, Pasadena, CA (US); Mark R. Holl, Shoreline, WA (US); Fred K. Forster, Seattle, WA (US); Eric Altendorf, Edmonds, WA (US); Paul C. Galambos, Albuquerque, NM (US); Margaret Kenny, Edmonds, WA (US); David Schutte, Auburn, WA (US); Gregory Hixson, Bothell, WA (US); Diane Zebert, Seattle, WA (US); Andrew Kamholz, Seattle, WA (US); Caicai Wu, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 09/703,764

(22) Filed: Nov. 1, 2000

Related U.S. Application Data

(63) Continuation-in-part of application No. 09/500,398, filed on Feb. 8, 2000, which is a continuation of application No. 09/346,852, filed on Jul. 2, 1999, which is a division of application No. 08/663,916, filed on Jun. 14, 1996, now Pat. No. 5,932,100, which is a continuation-in-part of application No. 08/829,679, filed on Mar. 31, 1997, now Pat. No. 5,972,710, which is a continuation-in-part of application No. 08/625,808, filed on Mar. 29, 1996, now Pat. No. 5,716,852.
(60) Provisional application No. 60/000,261, filed on Jun. 16, 1995.

(51) Int. Cl.[7] .............................................. B02D 11/00
(52) U.S. Cl. ..................... 210/634; 210/243; 210/511; 210/748; 73/61.71; 204/600; 209/1; 209/155; 422/101; 436/177
(58) Field of Search ............................... 210/134, 137, 210/143, 198.1, 243, 511, 634, 639, 739, 748; 422/62, 69, 70, 81, 101, 63; 436/177, 178, 180, 43, 52, 53; 204/600; 209/1, 155; 73/61.71

(56) References Cited

U.S. PATENT DOCUMENTS

| 3,449,938 A | 6/1969 | Giddings |
| 3,795,489 A | 3/1974 | Warnick et al. |

(List continued on next page.)

FOREIGN PATENT DOCUMENTS

| EP | 0 294 701 B1 | 12/1988 |
| EP | 0 345 782 A2 | 12/1989 |

(List continued on next page.)

OTHER PUBLICATIONS

Afromowitz, M.A. and Samaras, J.E., (1989), "Pinch Field–Flow Fractionation Using Flow Injection Techniques," *Separation Science and Technology* 24(5&6):325–339.

(List continued on next page.)

*Primary Examiner*—Joseph W. Drodge

(57) ABSTRACT

This invention provides microfabricated systems for extraction of desired particles from a sample stream containing desired and undesired particles. The sample stream is placed in laminar flow contact with an extraction stream under conditions in which inertial effects are negligible. The contact between the two streams is maintained for a sufficient period of time to allow differential transport of the desired particles from the sample stream into the extraction stream. In a preferred embodiment the differential transport mechanism is diffusion. The extraction system of this invention coupled to a microfabricated diffusion-based mixing device and/or sensing means allows picoliter quantities of fluid to be processed or analyzed on devices no larger than silicon wafers. Such diffusion-based mixing or sensing devices are preferably channel cell systems for detecting the presence and/or measuring the quantity of analyte particles in a sample stream.

29 Claims, 19 Drawing Sheets

U.S. PATENT DOCUMENTS

| | | | |
|---|---|---|---|
| 4,147,621 A | 4/1979 | Giddings | |
| 4,214,981 A | 7/1980 | Giddings | 209/155 |
| 4,250,026 A | 2/1981 | Giddings et al. | 209/155 |
| 4,683,212 A | 7/1987 | Uffenheimer | 436/52 |
| 4,726,929 A | 2/1988 | Gropper et al. | 422/68 |
| 4,737,268 A | 4/1988 | Giddings | 209/12 |
| 4,756,884 A | 7/1988 | Hillman et al. | 422/73 |
| 4,830,756 A | 5/1989 | Giddings | 210/739 |
| 4,894,146 A | 1/1990 | Giddings | 209/12 |
| 4,908,112 A | 3/1990 | Pace | |
| 5,007,732 A | 4/1991 | Ohki et al. | 356/73 |
| 5,039,426 A | 8/1991 | Giddings | 210/695 |
| 5,141,651 A | 8/1992 | Giddings | 210/748 |
| 5,156,039 A | 10/1992 | Giddings | 73/1 R |
| 5,193,688 A | 3/1993 | Giddings | 209/155 |
| 5,240,618 A | 8/1993 | Caldwell et al. | 210/748 |
| 5,250,263 A | 10/1993 | Manz | 422/81 |
| 5,288,463 A | 2/1994 | Chemelli | 422/58 |
| 5,304,487 A | 4/1994 | Wilding et al. | 435/291 |
| 5,322,626 A | 6/1994 | Frank et al. | 210/634 |
| 5,389,523 A | 2/1995 | Plant et al. | |
| 5,389,524 A | 2/1995 | Larsen et al. | 435/29 |
| 5,465,849 A | 11/1995 | Wada et al. | 209/214 |
| 5,480,614 A | 1/1996 | Kamahori | 422/70 |
| 5,498,392 A | 3/1996 | Wilding et al. | 422/68.1 |
| 5,534,328 A | 7/1996 | Ashmead et al. | 210/97 |
| 5,549,819 A | 8/1996 | Nickerson | 210/511 |
| 5,554,339 A | 9/1996 | Cozzette et al. | 422/69 |
| 5,571,410 A | 11/1996 | Swedberg et al. | 422/69 |
| 5,585,011 A | 12/1996 | Saaski et al. | 216/56 |
| 5,585,069 A | 12/1996 | Zanzucchi et al. | 422/100 |
| 5,587,128 A | 12/1996 | Wilding et al. | 435/287.3 |
| 5,599,432 A | 2/1997 | Manz et al. | 204/451 |
| 5,599,503 A | 2/1997 | Manz et al. | 422/82.05 |
| 5,603,351 A | 2/1997 | Cherukuri et al. | 137/1 |
| 5,605,662 A | 2/1997 | Heller et al. | 422/69 |
| 5,618,432 A | 4/1997 | Rewitzer et al. | 210/634 |
| 5,632,957 A | 5/1997 | Heller et al. | 422/69 |
| 5,635,358 A | 6/1997 | Wilding et al. | 435/7.2 |
| 5,637,469 A | 6/1997 | Wilding et al. | 435/287.2 |
| 5,639,423 A | 6/1997 | Northrup et al. | 435/287.3 |
| 5,674,743 A | 10/1997 | Ulmer | 435/287.2 |
| 5,681,484 A | 10/1997 | Zancucchi et al. | 216/56 |
| 5,707,799 A | 1/1998 | Hansmann et al. | 435/6 |
| 5,716,852 A | 2/1998 | Yager et al. | 436/172 |
| 5,726,404 A | 3/1998 | Brody | 200/81 R |
| 5,726,751 A | 3/1998 | Altendorf et al. | 356/246 |
| 5,747,349 A | 5/1998 | van den Engh et al. | 436/172 |
| 5,748,827 A | 5/1998 | Holl et al. | 385/141 |
| 5,842,787 A | 12/1998 | Kopf-Sill et al. | 366/340 |
| 5,869,004 A | 2/1999 | Parce et al. | 422/100 |
| 5,922,210 A | 7/1999 | Brody et al. | 210/767 |
| 5,932,100 A | 8/1999 | Yager et al. | 210/634 |
| 5,948,684 A | 9/1999 | Weigl et al. | 436/52 |
| 5,961,832 A | 10/1999 | Shaw et al. | 210/85 |
| 5,971,158 A | 10/1999 | Yager et al. | 209/155 |
| 5,974,867 A | 11/1999 | Forster et al. | 73/61.41 |
| 6,007,775 A | 12/1999 | Yager et al. | 422/57 |
| 6,136,272 A | 10/2000 | Weigl et al. | 422/82.05 |
| 6,159,739 A | 12/2000 | Weigl et al. | 436/52 |

FOREIGN PATENT DOCUMENTS

| | | |
|---|---|---|
| EP | 0 381 501 A2 | 8/1990 |
| EP | 0 645 169 A1 | 3/1995 |
| WO | WO93/22053 | 11/1993 |
| WO | WO93/22054 | 11/1993 |
| WO | WO93/22055 | 11/1993 |
| WO | WO93/22058 | 11/1993 |
| WO | WO93/22421 | 11/1993 |
| WO | WO 95/27211 | 10/1995 |
| WO | WO96/12540 | 10/1995 |
| WO | WO96/12541 | 10/1995 |
| WO | WO96/04547 | 2/1996 |
| WO | WO96/15576 | 5/1996 |
| WO | WO97/00125 | 1/1997 |
| WO | WO 97/02357 | 1/1997 |

OTHER PUBLICATIONS

Brody, J.P. and Yager, P., (Jun. 1996), "Low Reynolds Number Micro–fluidic Devices," *Solid State Sensor & Actuator Workshop,* Hilton Head, S.C., Jun. 2–6, 1996.

Elwenspoek, M. et al., (Dec. 1994), "Towards integrated mocroliquid handling systems," *J. Micromech. Microeng.* 4:227–245.

Faucheux, L.S., et al. (Feb. 1995), "Optical Thermal Ratchet," *Physical Rev. Letters* 74(9):1504–1507.

Forster, F.K. et al., (Nov. 1995), "Design, Fabrication and Testing of Fixed–Valve Micro–Pumps," *ASME International Mechanical Engineering Congress & Exposition,* San Francisco, ASME.

Fuh, C.B. et al., (1993), "Rapid Diffusion Coefficient Measurements Using Analytical SPLITT Fractionation: Application to Proteins," *Anal. Biochem.* 208:80–87.

Giddings, J.C., (1988), "Continuous Separation in Split–Flow Thin (SPLITT) Cells: Potential Applications to Biological Materials," *Sep. Sci.Technol.* 23(8&9):80–87.

Giddings, J.C. et al., "Outlet Stream Splitting for Sample Concentration in Field–Flow Fractionation," *Separation Science and Technology* (1983) 18(3):293–306.

Giddings, J.C., "Optimized Field–Flow Fractionation System Based on Dual Stream Splitters," *Anal. Chem.* (1985) 57:945–947.

Giddings, J.C. , (Jun. 1993), "Field–Flow Fractionation: Analysis of Macromolecular, Colloidal and Particulate Materials," *Science* 260:1456–1465.

Gravesen, P. et al., (1993), "Microfluidics—a review," *J. Micromechanics and Microengineering* 3(4):168–182.

Harrison, D.J. et al., (Aug. 1993), "Micromachining a miniaturized capillary electrophoresis–based chemical analysis system on a chip," *Science* 261:895–897.

Kittilsand, G. and Stemme, G., (1990), "A Sub–micron Particle Filter in Silicon," *Sensors and Actuators* A21–A23:904–907.

Leff, H.S. and Rex, A.F., (1990), "Resource Letter MD–1: Maxwell's demon," *Am. J. Physics* 58(3):201–209.

Levin, S. and Tawil, G., (Sep. 1993), "Analytical SPLITT Fractionation in the Diffusion Mode Operating as a Dialysis–like system Devoid of Membrane. Application to Drug–Carrying Liposomes," *Anal. Chem.* 65:2254–2261.

Manz, A. et al. (1994), "Electroosmotic pumping and electrophoretic separations for miniaturized chemical analysis system," *J. Micromech. Microeng.* 4:257–265.

Manz, A., (1993), "Planar Chips Technology for Miniaturzation of Separation Systems: A Developing Perspective inChemical Monitoring," *Adv. Chromatog.* 33:1–6.

Ramsey, J.M. et al. (Oct. 1995), "Microfabricated chemical measurement systems," *Nature Medicine* 1(10):1093–1096.

Rousselet, J., et al. (Aug. 1994), "Directional motion of brownian particles induced by a periodic asymmetric potential," *Nature* 370:446–448.

Shoji, S. and Esashi, M. (Dec. 1994), "Microflow devices and systems," *J. Micromechanics and Microengineering* 4:157–171.

Springston et al., (1987), "Continiuous Particle Fractionation Based on Gravitational Sedimentationin Split–Flow Thin Cells," *Analytical Chemistry* 59:344–350.

Verpoorte et al., (Dec. 1994), Three–Dimensional microflow manifods for minaturized chemical analysis systems, *J. Micromech. Microeng.* 4:246–256.

Wallis, G. and Pomerantz, D.I., (Sep. 1969), "Field assisted glass–metal sealing," *J. Applied Physics* 40(10):3946–3949.

Weigl, GH and Yager, P., (Apr. 1996), "Silicon–Microfabricated Diffusion–Based Optical Chemical Sensor," presented at the *Europtrode Conf.*, Zurich, Switzerland, Apr. 2–3, 1996.

Wilding, P. et al., (Jan. 1994), "Manipulation and Flow to Biological Fluids in Straight Channels Micromachined in Silicon," *J. Clin. Chem.* 40(1):43–47.

Williams, P.S. et al., (1992), "Continuous SPLITT Fractionation Based on a Diffusion Mechanism," *Ind. Eng. Chem. Res.* 31:2172–2181.

Yue, V. et al., (Sep. 1994), "Miniature Field–Flow Fractionation Systems for Analysis of Blood Cells," *Clin. Chem.* (1994) 40:1810–1814.

Chmelík et al., (1991), "Isoelectric focusing field–flow fractionation," *J. Chromatography* 545(2):349–358.

Petersen, K.E. (May 1982), "Silicon as a Mechanical Material," *Proc. IEEE* 70(5):420–457.

Reisman, A. et al. (1979) "The Controlled Etching of Silicon in Catalyzed Ethylenediamine–Pyrocatechol–Water Solutions," *J. Electrochem. Soc.* 126:1406–1415.

Weigl, B.H. et al. (Feb. 1997), "Fluorescence and absorbance analyte sensing in whole blood and plasma based on diffusion separation in silicon–microfabricated flow structures," SPIE Proceedings, J. Lakowitz (ed.), *Fluorescence Sensing Technology III* (Feb. 9–11).

Weigl, B.H. et al. (Nov. 1996), "Diffusion–Based Optical Chemical Detection in Silicon Flow Structures," *Analytical Methods & Instrumentation Special Issue μTAS 96*, pp. 174–184.

Weigl, B.H. et al. (Nov. 1996), "Rapid sequential chemical analysis in microfabricated flow structures using multiple fluorescent reporter beads," *μTAS 96* (Nov' 96).

Miyake, R. et al., "A Development of Micro Sheath Flow Chamber," in Proceedings of the IEEE Micro Electro Mechanical Systems Workshop (1991) Nara, Japan pp265–270.

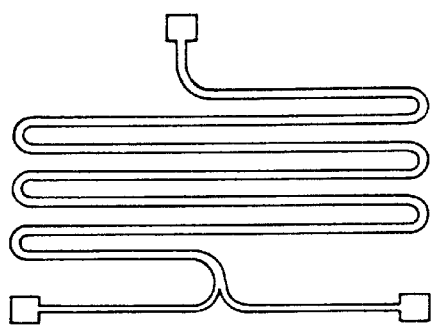
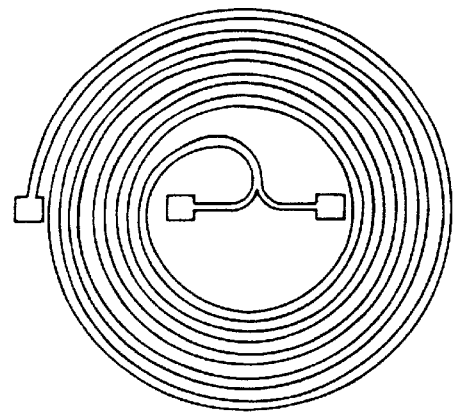
FIG. 17  FIG. 18
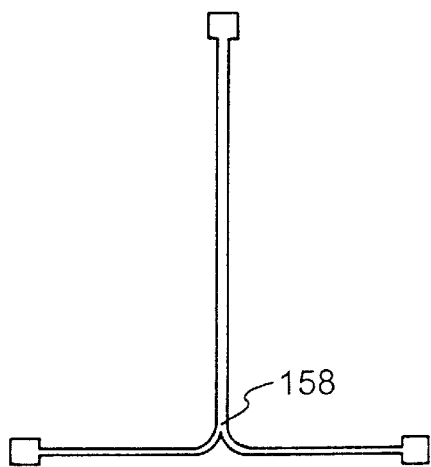
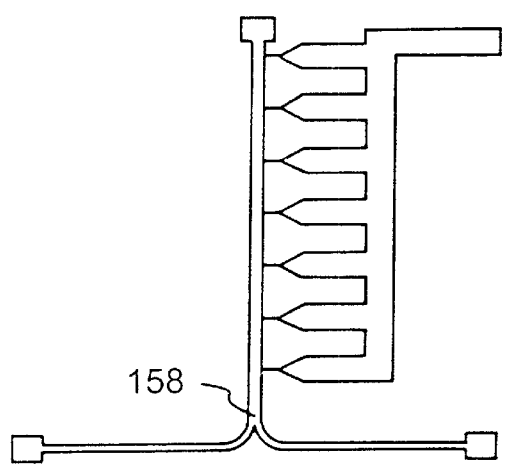
FIG. 19A  FIG. 19B

MICROFABRICATED DEVICES AND METHODS

CROSS-REFERENCE TO RELATED APPLICATIONS

This application is a continuation-in-part of application Ser. No. 09/500,398, filed Feb. 8, 2000, a continuation of application Ser. No. 09/346,852 filed Jul. 2, 1999, which is a divisional application of application Ser. No. 08/663,916 filed Jun. 14, 1996, now U.S. Pat. No. 5,932,100 issued Aug. 3, 1999, claiming priority to application Ser. No. 60/000,261 filed Jun. 16, 1995; and this application is also a continuation-in-part of application Ser. No. 08/829,679 filed Mar. 31, 1997, now U.S. Pat. No. 5,972,710, which is a continuation-in-part of application Ser. No. 08/625,808 filed Mar. 29, 1996, now U.S. Pat. No. 5,716,852, all of the foregoing applications being incorporated herein by reference to the extent not inconsistent herewith.

This invention was made with government support under Army research contract DAMD17-94-J-4460 awarded by the U.S. Army. The government has certain rights in the invention.

FIELD OF THE INVENTION

This invention relates generally to microfabricated extraction systems and methods for separating analytes from streams containing other constituents by differential transport principles such as diffusion and applied fields. The invention is useful, for example, for processing blood to separate a stream containing smaller particles such as albumin molecules from a stream containing cells. In another aspect this invention relates generally to microsensors and methods for analyzing the presence and concentration of small particles in streams containing both these small particles and larger particles by diffusion principles, and is useful, for example, for analyzing blood to detect the presence of small particles such as hydrogen, sodium or calcium ions in a stream containing cells.

BACKGROUND OF THE INVENTION

In Maxwell's famous gedanken (thought) experiment, a demon operates a door between two boxes of gas at the same temperature. The demon sorts the molecules, keeping the faster molecules in one box and the slower in the other, violating the basic laws of thermodynamics. This paradox has since been resolved in many different ways. Leff, H. S. and Rex, A. F. (1990), "Resource letter md-1: Maxwell's demon," Am. J. Physics 58:201–209.

A similar arrangement can be used to separate particles. Consider a mixture of particles of two different sizes suspended in water in one box and pure water in the other. If the demon opens and closes the door between the boxes quickly enough so that none of the larger particles have time to diffuse through the doorway, but long enough so that some of the smaller particles have enough time to diffuse into the other box, some separation will be achieved.

Recently two experiments have been done where a spatially asymmetric potential is periodically applied in the presence of a number of Brownian particles. Faucheux, L. S., et al. (1995), "Optical thermal ratchet," Physical Rev. Letters 74:1504–1507; Rousselet, J., et al. (1994), "Directional motion of Brownian particles induced by a periodic asymmetric potential," Nature 370:446–448. This has been shown to lead to a directed motion of the particles at a rate depending on the diffusion coefficient. One experiment (Rousselet, J., et al. (1994), "Directional motion of Brownian particles induced by a periodic asymmetric potential," Nature 370:446–448) used microfabricated electrodes on a microscope slide to apply an electric field for the potential. This idea is also the subject of European Patent Publication 645169 of Mar. 29, 1995, for "Separation of particles in a fluid using a saw-tooth electrode and an intermittent excitation field," Adjari, A., et al. The other experiment (Faucheux, L. S., et al. (1995), "Optical thermal ratchet," Physical Rev. Letters 74:1504–1507) used a modulated optical tweezer arrangement.

Chemical analysis of biological samples is constrained by sample size. Withdrawing a few milliliters of blood from an adult may have little effect, but repeating this procedure every hour or even withdrawing this amount once from an infant can significantly alter the health of the subject. For these reasons, a miniaturized blood analysis system would be useful. Furthermore, while many sophisticated tests that have great importance for critical care can be performed in major hospital laboratories, a substantial impact could be made on the practice of emergency medicine if some key tests could be performed on the patient at the site of injury. For some assays it is vital to make measurements in the absence of red blood cells, so some form of separation of cells from plasma is required.

Diffusion is a process which can easily be neglected at large scales, but rapidly becomes important at the microscale. The average time t for a molecule to diffuse across a distance d is $2t=d^2/D$ where D is the diffusion coefficient of the molecule. For a protein or other large molecule, diffusion is relatively slow at the macroscale (e.g. hemoglobin with D equal to $7 \times 10^{-7} cm^2/s$ in water at room temperature takes about $10^6$ seconds (ten days) to diffuse across a one centimeter pipe, but about one second to diffuse across a 10 $\mu$m channel).

Using tools developed by the semiconductor industry to miniaturize electronics, it is possible to fabricate intricate fluid systems with channel sizes as small as a micron. These devices can be mass-produced inexpensively and are expected to soon be in widespread use for simple analytical tests. See, e.g., Ramsey, J. M. et al. (1995), "Microfabricated chemical measurement systems," Nature Medicine 1:1093–1096; and Harrison, D. J. et al (1993), "Micromachining a miniaturized capillary electrophoresis-based chemical analysis system on a chip," Science 261:895–897.

Miniaturization of analytic instruments is not a simple matter of reducing their size. At small scales different effects become important, rendering some processes inefficient and others useless. It is difficult to replicate smaller versions of some devices because of material or process limitations. For these reasons it is necessary to develop new methods for performing common laboratory tasks on the microscale.

Devices made by micromachining planar substrates have been made and used for chemical separation, analysis, and sensing. See, e.g., Manz, A. et al. (1994), "Electroosmotic pumping and electrophoretic separations for miniaturized chemical analysis system," J. Micromech. Microeng. 4:257–265.

Field flow fractionation devices involve particle size separation using a single inlet stream. See, e.g. Giddings, J. C., U.S. Pat. No. 3,449,938, Jun. 17, 1969, "Method for Separating and Detecting Fluid Materials"; Giddings, J. C., U.S. Pat. No. 4,147,621, Apr. 3, 1979, "Method and Apparatus for Flow Field-Flow Fractionation"; Giddings, J. C., U.S. Pat. No. 4,214,981, Jul. 29, 1980, "Steric Field-Flow Fractionation"; Giddings, J. C. et al., U.S. Pat. No. 4,250, 026, Feb. 10, 1981, "Continuous Steric FFF Device for The Size Separation of Particles"; Giddings, J. C. et al. (1983), "Outlet Stream Splitting for Sample Concentration in Field-Flow Fractionation," Separation Science and Technology 18:293–306; Giddings, J. C. (1985), "Optimized Field-Flow Fractionation System Based on Dual Stream Splitters," Anal. Chem. 57:945–947; Giddings, J. C., U.S. Pat. No. 4,830,756, May 16, 1989, "High Speed Separation of Ultra-High Molecular Weight Polymers by Hyperlayer Field-Flow Fractionation"; Giddings, J. C., U.S. Pat. No. 5,141,651, Aug. 25, 1992, "Pinched Channel Inlet System for Reduced Relaxation Effects and Stopless Flow Injection in Field-Flow Fractionation"; Giddings, J. C., U.S. Pat. No. 5,156,039, Oct. 20, 1992, "Procedure for Determining the Size and Size Distribution of Particles Using Sedimentation Field-Flow Fractionation"; Giddings, J. C., U.S. Pat. No. 5,193,688, Mar. 16, 1993, "Method and Apparatus for Hydrodynamic Relaxation and Sample Concentration in Field-Flow Fraction Using Permeable Wall Elements"; Caldwell, K. D. et al., U.S. Pat. No. 5,240,618, Aug. 31, 1993, "Electrical Field-Flow Fractionation Using Redox Couple Added to Carrier Fluid"; Giddings, J. C. (1993), "Field-Flow Fractionation: Analysis of Macromolecular, Colloidal and Particulate Materials," Science 260:1456–1465; Wada, Y. et al., U.S. Pat. No. 5,465,849, Nov. 14, 1995, "Column and Method for Separating Particles in Accordance with Their Magnetic Susceptibility"; Yue, V. et al. (1994), "Miniature Field-Flow Fractionation Systems for Analysis of Blood Cells," Clin. Chem. 40:1810–1814; Afromowitz, M. A. and Samaras, J. E. (1989), "Pinch Field Flow Fractionation Using Flow Injection Techniques," Separation Science and Technology 24(5 and 6):325–339.

Thin-channel split flow fractionation (SPLITT) technology also provides particle separation in a separation cell having a thin channel. A field force is exerted in a direction perpendicular to the flow direction. Particles diffuse or are otherwise transported from a particle-containing stream across a transport stream to a particle-free stream. The device for operating the process is generally fabricated from glass plates with Teflon sheets used as spacers to form the channels. The channel depth can therefore be no smaller than the spacers, which are generally about 100 to 120 $\mu$m thick. See, e.g., Giddings, J. C., U.S. Pat. No. 4,737,268, Apr. 12, 1988, "Thin Channel Split Flow Continuous Equilibrium Process and Apparatus for Particle Fractionation"; Giddings, J. C., U.S. Pat. No. 4,894,146, Jan. 16, 1990, "Thin Channel Split Flow Process and Apparatus for Particle Fractionation"; Giddings, J. C., U.S. Pat. No. 5,093,426, Aug. 13, 1991, "Process for Continuous Particle and Polymer Separation in Split-Flow Thin Cells Using Flow-Dependent Lift Forces"; Williams, P. S. et al. (1992), "Continuous SPLITT Fractionation Based on a Diffusion Mechanism," Ind. Eng. Chem. Res. 31:2172–2181; and Levin, S. and Tawil, G. (1993), "Analytical SPLITT Fractionation in the Diffusion Mode Operating as a Dialysis-like System Devoid of Membrane. Application to Drug-Carrying Liposomes," Anal. Chem. 65:2254–2261.

An object of this invention is to provide a microfabricated extraction system utilizing differential transport principles in which an analyte can be extracted, detected and quantified.

The advantages, as disclosed herein, of diffusion separation devices on the microscale, e.g., having channel depths no greater than about 100 $\mu$m, do not appear to have been recognized in the prior art. See, e.g., Kittilsand, G. and Stemme, G. (1990), Sensors and Actuators A21–A23:904–907, and Wilding, P. et al. (1994), J. Clin. Chem. 40:43–47. None of the foregoing publications describe a channel system capable of analyzing small particles in very small quantities of sample containing larger particles, particularly larger particles capable of affecting the indicator used for the analysis. No devices or methods using indicator streams within the cell system are described.

All publications, patents and patent applications referred to herein are hereby incorporated by reference.

SUMMARY OF THE INVENTION

Microfluidic devices allow one to take advantage of diffusion as a rapid separation mechanism. Flow behavior in microstructures differs significantly from that in the macroscopic world. Due to extremely small inertial forces in such structures, practically all flow in microstructures is laminar. This allows the movement of different layers of fluid and particles next to each other in a channel without any mixing other than diffusion. On the other hand, due to the small lateral distances in such channels, diffusion is a powerful tool to separate molecules and small particles according to their diffusion coefficients, which are usually a function of their size.

In one aspect, this invention provides an extraction method and device distinguished from conventional filtration techniques and devices in possessing advantages of size, production economy, integrability with micro chemical analysis systems, low power consumption, and which may be operated in either a sample-to-sample or continuous processing mode. The device is particularly well suited to integration with microfabricated chemical analysis systems in which, for example, a preferred embodiment provides a microfabricated extraction device or system capable of providing a diluted plasma product having a volume ranging from picoliters to nanoliters starting from samples as small as a microliter of whole blood, with a comparable extraction stream volume.

The extraction system is useful as an element in an integrated system of microfluidic and detection elements (such as optical detectors) for tests of medical interest on blood, and also has applications in many other areas of analytical chemistry. In a preferred embodiment useful for blood analysis, the device allows for the extraction of plasma constituents from whole blood, thereby producing a cell-free fluid stream for subsequent analysis.

The microfabricated extraction system of this invention in simplest concept is illustrated by a diffusion extraction device comprising microchannels in the shape of an "H". A mixture of particles suspended in a sample stream enters the extraction channel (the crossbar of the "H") from one of the arms, e.g. the top left, and an extraction stream (a dilution stream) enters from the bottom left. The two streams flow together in the extraction channel; however, due to the small size of the channels, the flow is laminar and the streams do not mix. The sample stream exits as by-product stream at the upper right and the extraction stream exits as product stream from the lower right. While the streams are in parallel laminar flow in the extraction channel, particles having a greater diffusion coefficient (smaller particles such as albumin, sugars and small ions) have time to diffuse into the extraction stream, while the larger particles (e.g. blood cells) remain in the sample stream. Particles in the exiting extraction stream (now called the product stream) may be analyzed without interference from the larger particles.

In this patent application, the flow direction of a channel is called its length (L). The channel dimension in the direction of particle transport at right angles to the length (L) is called its depth (d). The third channel dimension at right angles to both the length and depth is called its width (w). The depth (d) is therefore perpendicular to the plane of interface of the sample and extraction streams. Table 1 lists other abbreviations used herein.

TABLE 1

| | |
|---|---|
| V | Volume |
| $V_{ss}$ | Sample stream flow rate (m³/s) |
| $V_{es}$ | Extraction stream flow rate (m³s) |
| $V_{ps}$ | Product stream flow rate (m³s) |
| $V_{bps}$ | By-product stream flow rate (m³s) |
| $V_{ind}$ | Indicator dye stream flow rate (m³s) |
| $V_{ds}$ | Detection stream flow rate (m³s) |
| $C_{i,ss}$ | Sample stream constituent i concentration (kg/kg) |
| $C_{i,es}$ | Extraction stream constituent i concentration (kg/kg) |
| $C_{i,bps}$ | By-product stream constituent i concentration (kg/kg) |
| $C_{i,ps}$ | Product stream constituent i concentration (kg/kg) |
| $C_{dye,ind}$ | Indicator stream dye concentration (kg/kg) |
| $C_{i,ds}$ | Detector stream constituent i concentration (kg/kg) |
| d | Diffusion direction extraction channel depth (m) |
| w | Extraction channel width (m) |
| L | Extraction channel length (m) |
| $a_\%$ | Percentage deviation from equilibrium concentration |
| $L_{a\%}$ | Device length required to achieve $a_\%$ (m) |
| $z_s$ | Interface streamline location between sample and extraction streams at the extraction channel entrance (m) |
| $z_p$ | Interface streamline location between the by-product and product streams (m) |
| P | Absolute pressure within the fluid stream (Pa) |
| $\Delta p$ | Differential pressure between the entrance and exit of the extraction channel (Pa) |
| $D_i$ | Binary diffusion coefficient of constituent i (m²/s) |
| $\mu$ | Fluid viscosity (Pa · s) |
| $\rho$ | Fluid density (kg/m³) |
| $\xi$ | Equilibrium normalized constituent concentration for an infinite length extraction channel (dimensionless) |
| $\tilde{c}$ | Normalized constituent concentration (dimensionless) |
| x | Channel length coordinate direction (flow direction) |
| y | Channel width coordinate direction |
| z | Diffusion direction coordinate |
| $\tilde{x}, \tilde{z}$ | Non-dimensional normalized variables (dimensionless) |
| w/d | Aspect ratio |
| D | Diffusion coefficient |
| Re | Reynolds number |
| T | Temperature |
| u | Axial velocity |

The length of the extraction channel and the extraction channel flow velocity are key parameters determining the amount of time the particles have to diffuse into the extraction stream. The particles in the case described above are differentially transported from the sample stream to the extraction stream using diffusion as the transport mechanism. Other means for effecting differential transport of the desired particles can also be used. The term "differential transport" means that a portion of the desired particles are transported from the sample stream into the extraction stream to the substantial exclusion of the undesired particles. For example, magnetic, electrical or other forces can be applied across the extraction stream, temperature gradients can be used, or absorbent or adsorbent materials such as antibodies can be added to the extraction stream to capture the desired particles.

The microfabricated device of this invention for extracting desired particles from a sample stream containing said particles comprises: a sample stream inlet; an extraction stream inlet; an extraction channel having an aspect ratio (channel width to depth) less than 50 in fluid communication with said sample stream inlet and said extraction stream inlet for receiving a sample stream from said sample stream inlet in parallel laminar flow with an extraction stream from said extraction stream inlet; a by-product stream outlet in fluid communication with said extraction channel for receiving a by-product stream comprising at least a portion of said sample stream from which desired particles have been extracted; and a product stream outlet in fluid communication with said extraction channel for receiving a product stream comprising at least a portion of said extraction stream and comprising desired particles extracted from said sample stream.

In this extraction embodiment, the sample stream and extraction stream inlets and the by-product stream and product stream outlets may comprise channels, reservoirs, ports, or other containers. The sample stream inlet is designed to receive a sample stream containing "desired particles," i.e. particles it is desired to extract so that their presence may be detected. The sample stream also includes other particles which are not extracted, termed "undesired particles" herein. These undesired particles include particles which might interfere with the detection of the desired particles. In a preferred embodiment, the sample stream comprises whole blood. The desired particles may be albumin or other blood plasma components, and the undesired particles are blood cells. The device is especially useful for obtaining cell-free plasma from whole blood. Other fluids for which the present invention is useful include solutions or suspensions of DNA fragments of different lengths, or proteins of varying sizes. Sample streams useful in the practice of this invention include fermentation broths, raw sewage, liquefied food samples, soil samples and biological fluids such as sputum, urine, and cerebral spinal fluid.

The diffusion analysis embodiment of this invention (also referred to herein as the "T-sensor") provides a channel cell system for detecting the presence of analyte particles in a sample stream also comprising larger particles comprising: a laminar flow channel; at least two inlet means in fluid connection with said laminar flow channel for respectively conducting into said laminar flow channel (1) an indicator stream, said indicator stream preferably comprising an indicator substance, for example, a pH-sensitive dye, which indicates the presence of said analyte particles by a detectable change in property when contacted with said analyte particles, and (2) said sample stream; wherein said laminar flow channel has a depth sufficiently small to allow laminar flow of said streams adjacent to each other and a length sufficient to allow analyte particles to diffuse into said indicator stream to the substantial exclusion of said larger particles in said sample stream to form a detection area; and outlet means for conducting said streams out of said laminar flow channel, preferably to form a single mixed stream.

The channel cell system of a preferred embodiment of the diffusion analysis embodiment of this invention comprises channel grooves in the form of a "T" or a "Y" having a central trunk and two branches etched into the surface of a silicon microchip, which surface is thereafter covered with a glass sheet. The central groove is formed of the trunk of the "T" or "Y", and the branches are the inlet means in fluid connection with the laminar flow channel for respectively conducting the sample and indicator streams into the laminar flow channel.

In the simplest embodiment of this diffusion analysis invention, a single indicator stream and a single sample stream are used; however, the methods and devices of this invention may also use multiple sample and/or indicator streams, and reference or calibration streams, all in laminar flow with each other. The preferred embodiments of this diffusion analysis invention utilize liquid streams, although the methods and devices are also suitable for use with gaseous streams. The term "fluid connection" means that fluid flows between the two or more elements which are in fluid connection with each other.

This invention farther provides a microfluidic system comprising a plurality of inlets; means for controlling fluid flow through at least one of said inlets connected with said inlet; a laminar flow channel in fluid communication with said inlets having an aspect ratio (w/d) less than 50; and at least one outlet in fluid communication with said laminar flow channel. Preferably the system also comprises means for controlling fluid flow through said outlet. The microfluidic system may have a plurality of (two or more) outlets, and preferably has means for controlling fluid flow through at least one of said outlets connected with that outlet. In one embodiment of this invention, the system has two inlets. It may have two outlets, at least three, or at least four outlets. In one embodiment it has at least six inlets and at least six outlets.

Also provided is a microfluidic system comprising a plurality of inlets; means for controlling fluid flow through at least one of said inlets connected with said inlet; a laminar flow channel in fluid communication with said inlets; at least three outlets in fluid communication with said laminar flow channel; and means for controlling fluid flow through at least one of said outlets connected with said outlet. In one embodiment, the system has at least four outlets, e.g., at least six inlets and at least six outlets.

Means for controlling fluid flow may be connected to all inlets, all outlets, all but one outlet, all but one inlet, and in a preferred embodiment are connected to all inlets and all but one outlet, or all outlets and all but one inlet. The means for controlling fluid flow may be any means known to the art, including pressure control means such as columns of water, electroendoosmotic forces, optical forces, gravitational forces and surface tension forces.

The laminar flow channel is designed to contain at least a first and second fluid stream in side-by-side laminar flow. Preferably the channel is long enough such that particles contained in one of the fluid stream can diffuse into the second stream for separation or detection.

Further provided herein is a method for creating a fluid interface between two or more streams flowing within a microfluidic channel comprising: simultaneously flowing said streams into a laminar flow channel having an aspect ratio (w/d) less than 50; and allowing said streams to flow in side-by-side laminar flow within said channel. The streams may be of equal volume and/or flow rate or unequal volume and/or flow rate. In the latter case, where a greater volume of one stream is flowed into the one stream than the other, or a lesser volume is allowed to exit the channel from one stream than the other, a fluid barrier can be formed between the streams. The streams may comprise a particle-containing stream and a particle-receiving stream, such that particles contained in the particle-containing stream are allowed to diffuse into the particle-receiving stream.

Further provided is a microfluidic device comprising: a microfluidic channel having a first end and a second end; and means for simultaneously introducing at least two fluids into said first end of said channel.

The devices of this invention preferably have no internal structures, i.e. structures such as splitters within the channel, not including outlet port configurations, which would interfere with the parallel laminar flow of streams therein.

The term "detection" as used herein means determination that a particular substance is present. Typically, the concentration of a particular substance is determined. The methods and apparatuses of this invention can be used to determine the concentration of a substance in a sample stream.

The input streams of this invention include a sample stream containing particles to be extracted, detected or analyzed. In the separation embodiment, a second input stream is referred to as the extraction or dilution stream. In the diffusion analysis embodiment, a second input stream is referred to as the indicator stream. In the separation embodiment, the laminar flow channel is sometimes referred to as the extraction channel, and in the diffusion analysis embodiment the laminar flow channel is sometimes referred to as the diffusion channel.

One preferred embodiment entails the incorporation in the extraction or indicator stream of an adsorbent material such as a receptor with specificity for the desired ligand particles, onto an effectively non-diffusing substrate, such as plastic beads or high molecular weight polymers. Another preferred embodiment utilizes an effectively non-diffusing absorbent particulate material with specificity for the desired particles. Such materials are considered "effectively non-diffusing" when they do not diffuse into the sample stream, or do not diffuse into the sample stream in quantities large enough to interfere with detection of the undesired particles in the by-product stream. In the absorbent embodiment, desired particles are absorbed within the effectively non-diffusing absorbing particulate material, whereas in the adsorbent embodiment, the desired particles attach to the surface of the effectively non-diffusing substrate plastic beads or to ligands attached thereto. Numerous suitable ligands for desired particles in the adsorbent/absorbent embodiment are known to the art, and specific teachings relative to these techniques are disclosed in application Ser. No. 08/876,038 filed Jun. 14, 1996, now U.S. Pat. No. 5,971,158 issued Oct. 26, 1999.

In the diffusion analysis embodiment of this invention, the channel cell system of this invention may comprise external detecting means for detecting changes in an indicator substance carried within the indicator stream as a result of contact with analyte particles. Detection and analysis is done by any means known to the art, including optical means, such as optical spectroscopy, and other means such as absorption spectroscopy or fluorescence, by chemical indicators which change color or other properties when exposed to the analyte, by immunological means, electrical means, e.g. electrodes inserted into the device, electrochemical means, radioactive means, or virtually any microanalytical technique known to the art including magnetic resonance techniques, or other means known to the art to detect the presence of an analyte such as an ion, molecule, polymer, virus, DNA sequence, antigen, microorganism or other factor. Preferably optical or fluorescent means are used, and antibodies, DNA sequences and the like are attached to fluorescent markers.

The term "particles" refers to molecules, cells, large molecules such as proteins, small molecules comprised of one or several atoms, and ions. The particles may be suspended or dissolved in the stream. The term "stream" refers to a carrier fluid such as water or other liquid, air or other gas, containing desired and/or undesired particles. The term "particles" as used herein does not include the molecules of the carrier stream.

The term "extraction" refers to the separation of at least a portion, i.e. a detectable portion, of desired particles from the sample stream to the substantial exclusion of undesired particles. It is recognized that very small amounts of undesired particles may be transported into the extraction stream; however, the presence of such undesired particles will be minimized such that they do not interfere with detection or subsequent processing of the streams containing the desired particles.

The methods of this invention are designed to be carried out such that all flow is laminar. In general, this is achieved in a device comprising microchannels of a size such that the Reynolds number for flow within the channel is below about 1, preferably below about 0.1. The term "laminar flow" of two streams means stable, side-by-side, non-recirculating, flow of two streams without mixing. There are no zones of recirculation, and turbulence is negligible.

The input or sample stream may be any stream containing particles of the same or different size, for example blood or other body fluid, contaminated drinking water, contaminated organic solvents, urine, biotechnological process samples, e.g. fermentation broths, and the like. The particles to be separated, or analyzed ("the analyte"), may be any smaller particles in the input stream capable of diffusing into the extraction or indicator stream in the device, e.g. hydrogen, calcium or sodium ions, proteins, e.g. albumin, organic molecules, drugs, pesticides, and other particles. In a preferred embodiment when the sample stream is whole blood, small ions such as hydrogen and sodium diffuse rapidly across the channel, whereas larger particles such as those of large proteins, blood cells, etc. diffuse slowly. Preferably the particles to be separated or analyzed are no larger than about 3 micrometers, more preferably no larger than about 0.5 micrometers, or are no larger than about 1,000,000 MW, and more preferably no larger than about 50,000 MW.

The diffusion analysis system includes an indicator stream introduced into one of the inlet means comprising a liquid carrier which may contain substrate particles such as polymers or beads having an indicator substance immobilized thereon. The indicator substance is preferably a substance which changes in fluorescence or color in the presence of analyte particles, such as a dye, enzymes, and other organic molecules that change properties as a function of analyte concentration. The term "indicator substance" is also used to refer to polymeric beads, antibodies or the like having dyes or other indicators immobilized thereon. It is not necessary that the indicator stream comprise an indicator substance when detection means such as those directly detecting electrical, chemical or other changes in the indicator stream caused by the analyte particles are used. The system may also include an analyte stream comprising substrate particles such as polymer beads, antibodies and the like on which an indicator substance is immobilized. The liquid carrier can be any fluid capable of accepting particles diffusing from the feed stream and containing an indicator substance. Preferred indicator streams comprise water and isotonic solutions such as salt water with a salt concentration of about 10 mM NaCl, KCl or MgCl, or organic solvents like acetone, isopropyl alcohol, ethanol, or any other liquid convenient which does not interfere with the effect of the analyte on the indicator substance or detection means.

In the devices of this invention, the streams may be separated at the end of the conduit at any arbitrary location by precise regulation of the exit flow rate of the outlets, something which is not possible at higher Reynolds numbers not satisfying the non-recirculating and non-turbulent criteria.

In the separation embodiment of this invention, the extraction stream inlet is designed to receive an extraction stream capable of accepting desired particles when in laminar flow contact with the sample stream. The extraction stream can be any fluid capable of accepting particles being transported from the sample stream. Preferred extraction streams are water and isotonic solutions such as physiological saline. Other useful extractant streams comprise organic solvents such as acetone, isopropyl alcohol, supercritical carbon dioxide or ethanol. Air and other gases may also be used as sample and extraction streams.

In the separation embodiment, the by-product stream comprises the sample stream from which a portion of the desired particles have been extracted and may or may not, as discussed below, be comprised of a fraction of the extraction stream into which desired particles have been conveyed from the sample stream. The by-product stream outlet is designed to conduct the by-product stream (composed of the sample stream and perhaps a portion of the extraction stream) that is removed from the extraction channel to disposal, recycle, or other system component, for further processing.

In this separation embodiment, the product stream comprises at least a portion of the extraction stream into which desired particles have been extracted. The product stream outlet, which as stated above, may comprise a product stream channel, is designed to conduct the product stream containing a detectable quantity of desired particles to a detection or further processing area or system component. A sufficient quantity of the extraction stream must be present in the product stream, comprising a sufficient quantity of desired particles, such that the presence of the desired particles is detectable in the product stream by means known to the art. The product stream may be conducted to a reservoir chamber, or other device where it may be further treated, e.g. by mixing, separating, analyzing, heating or otherwise processing, for example as disclosed in Wilding, P., et al. U.S. Pat. No. 5,304,487 issued Apr. 19, 1994, incorporated herein by reference.

The channel cell may be fabricated by microfabrication methods known to the art, e.g. as exemplified herein, a method comprising forming channels in a silicon microchip, such as by etching grooves into the surface of the silicon microchip and placing a glass cover over the surface. Precision injection molded plastics may also be used for fabrication. The term "microfabricated" refers to devices capable of being fabricated on silicon wafers readily available to those practicing the art of silicon microfabrication and having the feature sizes and geometries producible by such methods as LIGA, thermoplastic micropattern transfer, resin based microcasting, micromolding in capillaries (MIMIC), wet isotropic and anisotropic etching, laser assisted chemical etching (LACE), and reactive ion etching (RIE), or other techniques known within the art of microfabrication. In the case of silicon microfabrication, larger wafers will accommodate a plurality of the devices of this invention in aplurality of configurations. A few standard wafer sizes are 3", 4", 6", and 8". Application of the principles presented herein using new and emerging microfabrication methods is within the scope and intent of the claims hereof.

The inlets need only be sized large enough to conduct the streams into parallel laminar flow, e.g., the device may comprise channels less than or equal to about 5 mm in length, less than about 100 micrometers in depth and less than or equal to 5 mm in width. The outlets may similarly be minimal in size, comprising channels with dimensions as stated above for the inlets. These inlets and outlets may be as long, deep and wide as required by the system of which they are a part, however, they preferably have a volume less than about 2.5 microliters to accommodate small sample sizes.

The width and depth of the inlet and outlet channels must be large enough to allow passage of the undesired particles, preferably anywhere between about 2 or 3 times the diameter of the undesired particles in the sample stream and less than or equal to about 5 mm. Particle sizes range from one or a few Å for small organic and inorganic molecules and ions to about 0.01 micrometers in depth for proteins, to about 0.1–1 micrometers for flexible long-chained molecules, to about 8 micrometers for red blood cells, to about 15 micrometers for most white blood cells, and up to about 25 micrometers for some white blood cells. The laminar flow channel must additionally be large enough to allow passage of particles used in the extraction or indicator stream, such as adsorbent or absorbent particles, and is preferably between about 2 or 3 times the diameter of such particles and less than or equal to 5 mm. The laminar flow channel is most preferably less than 100 micrometers in order to achieve particle transport in a reasonable period of time. The width and depth of the laminar flow channel and outlet channels must be large enough to allow passage of the desired particles, and any other particles associated with them, such as adsorbent or absorbent particles, and are preferably between about 2 or 3 times the diameter of any absorbent or adsorbent particles present in the streams and less than or equal to 5 mm. If the width dimension is in the wafer thickness direction, then for the silicon microfabricated embodiments of the microscale devices of the present invention, the width of the channels, inlets and outlets is less than the silicon wafer thickness, i.e. about 300 micrometers.

If the depth dimension is in the wafer thickness direction, then for the silicon microfabricated embodiments of the microscale extraction devices of the present invention the depth of the inlet and outlet is less than the silicon wafer thickness, i.e. about 300 micrometers. Preferably the depth, particularly of the laminar flow channel, is less than about 200 micrometers, and more preferably less than about 100 micrometers.

The laminar flow channel (called the "extraction channel" in the separation embodiment) receives the inflow of the sample and extraction streams from the sample and extraction stream inlets and conducts these streams in parallel laminar flow for a distance sufficient to allow extraction of the desired particles into the extraction stream. In the diffusion analysis embodiment of this invention, the laminar flow channel is long enough to permit small analyte particles to diffuse from the sample stream and have a detectable effect on an indicator substance or detection means, preferably at least about 2 mm long. The length of the flow channel depends on its geometry. The diffusion coefficient of the analyte, which is usually inversely proportional to the size of the analyte, affects the desired flow channel length. For a given flow speed, particles with smaller diffusion coefficients require a longer flow channel to have time to diffuse into the indicator stream.

The laminar flow channel can be straight or non-straight, i.e., convoluted. A convoluted flow channel as used herein refers to a flow channel which is not straight. A convoluted channel can be, for example, coiled in a spiral shape or comprise one or a plurality of "hairpin" curves, yielding a square wave shape. Convoluted channels provide longer distances for diffusion to occur, thereby allowing for measurement of analytes with larger diffusion coefficients, e.g., typically larger analytes. In preferred embodiments of this invention wherein a silicon microchip is the substrate plate in which the flow channel is formed, the channel length of a straight flow channel is between about 5 mm and about 50 mm. In preferred embodiments of this invention wherein the flow channel is convoluted, i.e., non-straight, the length of the flow channel is defined or limited only by the size of the microchip or other substrate plate into which the channel is etched or otherwise formed. The channel width (diffusion direction) is preferably between about 20 micrometers and about 1 mm. The channel is more preferably made relatively wide, e.g. at least about 200 micrometers, which makes it easier to measure indicator fluorescence with simple optics, and less likely for particles to clog the channel. However, the channel can be made as narrow as possible while avoiding clogging the channel with the particles being used. Narrowing the width of the channel makes diffusion occur more rapidly, and thus detection can be done more rapidly. The channel depth is small enough to allow laminar flow of two streams therein, preferably no greater than about 1000 micrometers and more preferably between about 50 micrometers and about 400 micrometers.

In some embodiments of the diffusion analysis invention, the laminar flow channel may be long enough to allow the indicator and sample streams to reach equilibrium with respect to the analyte particles within the channel. Equilibrium occurs when the maximum amount of smaller particles have diffused into the indicator stream.

Alternatively, to allow more time for diffusion to occur, the flow rate can be decreased. However, several factors limit the minimum flow rate and therefore make a longer flow channel desirable in some cases. First, the flow rate is achieved by a pumping means or pressure source, some of which cannot produce as low a pressure and flow rate as may be desired, to allow enough time for diffusion of particles with small diffusion coefficients. Second, if the flow rate is slow enough and some particles are of significantly different density from the surrounding fluid streams, particles denser than the surrounding fluid streams may sink to the bottom of the flow channel and particles less dense than the surrounding fluid streams may float to the top of the flow channel. It is preferable that the flow rate be fast enough that hydrodynamic forces substantially prevent particles from sticking to the bottom, top, or walls of the flow channel. Third, a small change in pressure leads to larger errors in measurement accuracy at lower flow rates. Fourth, at low flow rates, other factors, such as changes in viscosity of fluids, can lead to larger errors in measurement accuracy.

The inlet and outlet channels are preferably between about 2 to 3 times the maximum-sized stream particulate diameter and about 100 micrometers in width and between about 2 to 3 times the diameter of the maximum-sized particles and less than about 100 micrometers in depth, and the extraction channel is between about 2 to 3 times the diameter of the maximum-sized particles and about ⅔ the wafer thickness in width, between about 2 to 3 times the diameter of the maximum-sized particles and less than about 100 micrometers in depth, and between about 4 and about 10 times the diameter of the maximum-sized particles and less than or equal to 5 mm long.

In an embodiment of the separation device in which the particle transport direction is rotated 90 degrees from that of the "H" design, called the "flat extraction device" herein, the inlet channels have a width equal to the extraction channel width at the entrance to the extraction channel of preferably between 2 and 3 particle diameters and about 500 micrometers, and the extraction channel is preferably between about 2 and 3 times the diameter of maximum-sized particles and less than or equal to 5 mm in width, between about 2 and 3 times the diameter of the maximum-sized particles and less than about 100 micrometers in depth, and between about 4 and about 10 times the diameter of the maximum-sized particles and less than or equal to 5 mm long.

The term "aspect ratio" as used herein refers to the ratio of the width to the depth of a channel.

The laminar flow channels of this invention preferably have an aspect ratio less than 50. The aspect ratio may be less than 25 or any number from less than 1 to 49. Microfabricated devices of this invention which can be manufactured with laminar flow channels having aspect ratios less than 50 and having depths less than 100 micrometers have numerous advantages over similar constructions with larger aspect ratios and larger laminar flow channel depths. Motive forces on particles capable of effecting differential transport of desired particles within the laminar flow channel are the result of local field gradients. Ultra-small transport distances enable differential transport of desired particles faster than undesired particles in short periods of time, allowing for significant minimization of the size needed for the device at moderate extraction channel flow rates. In addition lower flow rates can be used.

Devices within the size range described above yield distinctive advantages when evaluated in the following performance categories: (a) power consumption to achieve objective, (b) size of device required to achieve the objective, and (c) integratability of devices in a plurality of systems for management and processing of very small fluid volumes in a batch (sample to sample) mode.

Some fields known to the art which may be used for differential transport of the particles in the devices of this invention are those produced by:

Sedimentation

Electrical energy

Temperature gradients

Cross Flow

Dielectrical gradients

Shear forces

Magnetic forces

Concentration gradients

Means for producing such fields are known to the art in connection with mesoscale and macroscale devices.

Because of the small sizes of the channels described herein, differential transport of desired particles by diffusion or other means occurs extremely rapidly, e.g. within less than about 300 seconds, and if desired, less than about one second. Devices according to this invention can be fabricated which will detect the presence or determine the concentration of desired or undesired particles in the product and/or by-product streams where these particles occur in less than five minutes, or if desired in less than four minutes, or less than three minutes, or less than two minutes, or less than one minute, or less than ten seconds, or less than one second.

In the microfabricated devices of this invention in comparison to the larger-scale devices of the prior art having channel depths greater than 100 micrometers, samples of much smaller size, e.g. about 1 mL, and down to about 1 picoliter, may be treated, whereas in larger devices, very small samples could be absorbed onto the channel walls. In addition, low Reynolds numbers for the flow are achieved, allowing for laminar flow and minimizing or totally eliminating turbulence which would interfere with differential extraction of desired particles.

In the separation embodiment of this invention, a portion of the desired particles in the sample stream (having larger diffusion coefficients than the undesired particles, or being more susceptible than the undesired particles to transport into the extraction stream when differential transport means are applied to the system) is transported to the product stream. When the extraction is diffusion-based, some of the smaller particles will always remain in the sample stream; however, the percentage of desired particles transported to the product stream can be increased by increasing the time of contact of the sample and extraction streams, e.g. by increasing the length of the extraction channel or reducing the flow velocity. For simple diffusion systems, the process may be timed such that the two streams are in contact up to the point where the concentration of smaller particles in both streams is almost equal.

The sample and extraction streams may have different properties e.g. viscosities, densities, surface energies, diffusion coefficients, homogeneities, chemical compositions and the like, which may affect the differential transport rates. System parameters may need to be adjusted and optimized to take account of these differing properties, as will be apparent to those skilled in the art.

The sample and extraction streams are kept in contact in the extraction channel for a period of time sufficient to allow an analyzable quantity of desired particles to be transported into the extraction stream. The amount of product recovered from the device may be between about 0.001 picoliter/sec and about 50 microliters/sec or more. For example, illustrated herein is an optimal flow rate for the product stream of about 200 nanoliters/sec. As is known in the art, even the very small amounts of analytes present in such small product streams may be detected by spectroscopic and other means.

Successful operation of the inventions described herein requires precise control of volume flow rates on three of the four channels of the device (i.e. sample, extraction, product, and by-product streams). The fourth channel need not and should not be regulated, as leaving this channel unregulated will allow the device to accommodate unpredictable changes in volume of the sample because of $\Delta V$ of mixing of the sample and extraction streams. Means for achieving precisely regulated flow rates are known to the art. For devices with more or less inputs and outputs, flow control means connected to all but one of these are preferred.

To aid in controlling the size of particles being transported to the product stream in a diffusion-based extraction system of this invention, and reduce the appearance of larger particles in the product stream, a fluid barrier may be created in the extraction channel. Such a fluid barrier is present when the extraction stream is present in sufficient volume to cause a portion of the extraction stream to flow through the by-product exit with the exiting by-product stream, as illustrated in FIG. 3. Smaller particles diffusing into the extraction stream must cross the width of this fluid barrier before being able to exit with the product stream. Such fluid barriers formed on a larger scale are discussed in Williams P. S., et al. (1992), "Continuous SPLITT Fractionation Based on a Diffusion Mechanism," Ind. Eng. Chem. Res. 2172–2181, incorporated herein by reference.

By controlling the pressure of the sample and extraction streams, the ratio of volume from each that enters the extraction channel can be controlled. The volume ratio of the sample stream and the extraction stream can also be set by the geometry of the outlet and inlet channels for a fixed delivery pressure on the sample and extraction streams. The volume flow rate of the product and by-product streams may also be controlled by manipulating the product and by-product stream pressures or by using arbitrary port (inlet) pressures and altering the flow resistance of the inlets. Whatever the control mode, the inlet and outlet channels must satisfy the criteria for minimum channel dimensions based on the size of the particulate to be processed as described above. If the volume of the extraction stream entering the extraction channel is greater than the volume of the sample stream, and the two exit streams are identical, a fluid barrier is formed. If the volume flow rate of the product stream is too small to accommodate the entire volume flow of the extraction stream then a fluid barrier will also be formed.

The diffusion analysis system of this invention, in addition to the sample and indicator stream inlet channels and the outlet channels, may also comprise specimen channels and outlet means such as smaller channels for conducting specimen streams from the indicator stream at successive intervals along the length of the laminar flow channel, and means including viewports and fluorescence detectors for measuring changes in an indicator substance in each specimen stream, whereby concentration of the analyte in the sample stream may be determined.

Dual detection embodiments of the device of the present invention which allow for detection of both undissolved and dissolved analytes are also provided. Detection of both undissolved and dissolved analytes can be achieved in one dual detection device: dissolved particles can be detected in the flow channel of the T-sensor and undissolved particles can be detected in a v-groove channel or sheath flow module, either or both of which can be in fluid connection with a T-sensor flow channel. Branching flow channels can provide for fluid connection between a T-sensor flow channel and a v-groove channel and/or sheath flow module.

The channel cell systems of this invention can be in fluid connection with a v-groove flow channel, which preferably has a width at the top small enough to force the particles into single file but large enough to pass the largest particles without clogging. V-groove channels are formed by anisotropic EPW (ethylenediamine-pyrocatechol-water) etching of single crystalline silicon microchips, providing access to reflective surfaces with precisely etched angles relative to the surface of the microchip (Petersen, Proc. IEEE 70(5): 420–457,1982). (U.S. patent application Ser. No. 08/534, 515 (U.S. Pat. No. 5,726,751), "Silicon Microchannel Optical Flow Cytometer," which is incorporated by reference herein in its entirety, discloses a flow cytometer comprising a v-groove flow channel formed by micromachining a silicon microchip.) The cross-section of such a channel is like a letter V, and thus is referred to as a v-groove channel. An optical head comprising a laser and small and large angle photodetectors adapted for use with a v-groove flow channel can be employed as well. As described in U.S. patent application Ser. No. 08/534,515 (U.S. Pat. No. 5,726,751), detectors placed at small and large angles with respect to the portion of the probe beam reflected from the v-groove wall can be used to count particles, such as cells, and distinguish them by size (via small angle detector) and structure/morphology (via large angle detector). Using an appropriate laser or LED source, e.g., a blue laser, which can be determined by routine choice by those of ordinary skill in the art, fluorescence detection can be performed by placing an appropriate filter in front of the large angle detector.

The laminar flow channel can be in fluid connection with a v-groove channel allowing for dual detection of dissolved and undissolved, single-file particles with one device. The fluid streams can flow first through a T-sensor flow channel and then through a v-groove channel, viabranching flow channels. Alternatively, the fluid stream can flow first through a v-groove channel and then through a laminar flow channel, e.g., of a diffusion analysis device of this invention.

An alternative means of achieving single file particle flow through a flow channel is the sheath flow module disclosed in U.S. patent application Ser. No. 08/823,747, "Device and Method for 3-Dimensional Alignment of Particles in Microfabricated Flow Channels," filed Mar. 26, 1997, now U.S. Pat. No. 6,159,739 issued Dec. 12, 2000, and specifically incorporated in its entirety by reference herein. The sheath flow module includes a first plate of material having formed therein a laminar fluid flow channel; at least two inlets, each inlet joining the laminar flow channel at a junction, the first inlet junction being wider than the second inlet junction, and an outlet from the flow channel. A second plate, e.g., a transparent cover plate, seals the module and allows for optical measurements. A transparent cover plate allows for optical measurements by reflection, in cases where the first plate is a reflective material, e.g., silicon. A first inlet allows for introduction of a first fluid into the flow channel. The first fluid is the sheath fluid. A second inlet allows for introduction of a second fluid into the sheath fluid while it is flowing through the flow channel. The second fluid is the center fluid. Because the second inlet junction is narrower than the first inlet junction, the center fluid becomes surrounded on both sides by the sheath fluid. After all fluids have been introduced and sheath flow has been achieved, the depth of the flow channel can be decreased, leading to vertical hydrodynamic focusing. Optionally, the width of the flow channel can be decreased, leading to horizontal hydrodynamic focusing. The decrease in depth and width can be gradual or abrupt Hydrodynamic focusing in the sheath flow module leads to single file particle flow.

The sheath flow module can be in fluid connection with the channel cell system of the present invention. The fluid streams can flow first through a T-sensor flow channel and then through a sheath flow module. Alternatively, the fluid stream can flow first through a sheath flow module and then through a T-sensor flow channel.

Channel cells of this invention may include multiple inlet branches in fluid connection with the laminar flow channel for conducting a plurality of inlet streams into said channel. These may be arranged in a "candelabra"-like array or may be arranged successively along a "crossbar" for the "T," the branches of the "Y," or the inlet bar of the "H" configuration, the only constraint being that laminar flow of all the streams must be preserved.

Inlet means include the inlet channels or "branches" and may also include other means such as tubes, syringes, and the like which provide means for injecting feed fluid into the device. Outlet means include collection ports, and/or means for removing fluid from the outlet, including receptacles for the fluid, means inducing flow by capillary action, pressure, gravity, and other means known to the art. Such receptacles may be part of an analytical or detection device.

Embodiments of the devices of the present invention which allow for optical measurements in transmission are provided. In such embodiments, the channel cell system, or at least an analyte detection area, may transect the width of the substrate plate in which the channel cell system is formed. Substrate plate as used herein refers to the piece of material in which the channel cell system of this invention is formed, e.g., a silicon wafer and a plastic sheet. The analyte detection area, and optionally other parts of the channel cell system, lie between optically transparent plates in a space which cuts through the entire width of the substrate plate. Analyte detection area as used herein refers to that portion of the indicator stream where analyte particles create a detectable change in the indicator stream.

Optical measurements exploiting reflected light are referred to herein as detection by reflection, whereas optical measurements exploiting transmitted light are referred to herein as detection by transmission.

Extraction devices of this invention may comprise means for controlling the volume of extraction stream in the extraction channel with respect to the volume of the sample stream, which means include a product stream outlet smaller than required to allow the entire extraction stream to exit coupled with a by-product stream outlet large enough to handle the excess extraction stream. Extraction devices of this invention may comprise multiple product stream outlets so that product streams comprising different types of desired particles may be recovered.

The separation devices of this invention may be utilized as a sample pretreatment system for an analytical system including sensing means for detecting desired particles in the product stream. Such means include means for mixing the product stream with an indicator stream which interacts with the desired particles so as to allow them to be detected by sensing means known to the art, including optical means, such as optical spectroscopic equipment, and other means such as absorption spectroscopic equipment or means for detecting fluorescence, chemical indicators which change color or other properties when exposed to the desired particles of analyte, immunological means, electrical means, e.g. electrodes inserted into the device, electrochemical means, radioactive means, or virtually any microanalytical technique known to the art including magnetic resonance equipment or other means known to the art to detect the presence of analyte particles such as ions, molecules, polymers, viruses, DNA sequences, antigens, microorganisms, or other factors. Preferably, optical or fluorescent means are used, and antibodies, DNA sequences and the like are attached to fluorescent markers. Indicators and microfabricated mixing means, as well as detection and sensing means are described, e.g in copending application Ser. No. 08/625,808 (U.S. Pat. No. 5,716,852) incorporated herein by reference.

In a preferred embodiment of this invention the differential extraction device described above is integrated into an analytical system comprising means for further processing the product and/or by-product streams, such as diffusion-based mixing devices for mixing the product stream with an indicator substance (e.g. the T-sensor device), and detection chambers wherein the presence of desired analyte particles may be detected. These additional processing means are preferably incorporated with the differential extraction device in a "lab-on-a-chip," fabricated on a standard silicon wafer. In a preferred embodiment, the system comprises quantitation means for determining the concentration of the analyte particles (desired or undesired particles) in the product and/or by-product stream and/or determining the concentration of the analyte particles in the sample stream. Such means include spectroscopic equipment, potentiometric, amperometric, and dielectric relaxation equipment. Concentration determinations can be made by calculation or calibration by means known to the art and disclosed herein.

The differential extraction devices of this invention are used in a method for extraction of at least a portion of desired particles from a sample stream comprising said desired particles and also containing undesired particles, comprising: introducing said sample stream into the sample stream inlet of a microfabricated extraction device as described above; introducing an extraction stream into the extraction channel of said extraction device; and withdrawing a product stream comprising desired particles from the product stream outlet of said device.

Methods are also provided for detecting the presence of analyte particles in a sample stream, preferably a liquid stream, also comprising larger particles comprising: conducting said sample stream into a laminar flow channel; conducting an indicator stream, said indicator stream preferably comprising an indicator substance which indicates the presence of said analyte particles, by a detectable change in property when contacted with particles of said analyte into said laminar flow channel, whereby said sample stream and said indicator stream flow in adjacent laminar streams in said channel; allowing analyte particles to diffuse into said indicator stream; and detecting the presence of particles of the analyte in said indicator stream.

The methods are performed in either batch or continuous mode operation. In batch mode, sample sizes may be as small as about one picoliter, preferably no more than about 250 microliters and more preferably are no more than about 50 microliters, although sample sizes of up to 1 mL or 10 mL or greater are also contemplated. The methods are completed in a time period from less than 1 second to no more than about 5 minutes, although, again, the device can be fabricated to allow batch processing times of 10, 30, or 45 seconds, or 1, 2, 3 or 4 minutes, or less.

The batch method includes a start-up transition period wherein the fluid (which may be a gas) present within the device is displaced by the extraction and sample indicator and analyte streams as they enter the laminar flow channel until such time as the streams exist in a nearly equilibrium mass transport state.

A diffusion period follows during which time the streams are in contact in the laminar flow channel for a period of time sufficient to allow sufficient desired particles to be differentially transported into the other stream for analysis or further processing.

A shut-down device flush period then may be required during which a cleansing fluid such as water (or soap solution) or air or sequential combinations of water (or soap solution) and air is cycled through the device to remove both desired and undesired particles which may have been retained on the surface of the device.

The batch method of the separation embodiment of this invention which involves processing of one single, discrete sample at a time, may include recycle of the by-product stream into the sample stream inlet and repetition of the process to increase the amount of desired particles removed from the original sample. In this embodiment a sample of the undesired particles is generated which may be useful for subsequent analysis. The processes of this invention can be repeated until the desired particles have been substantially completely extracted from the sample stream.

In the continuous mode of this invention, the process may be continued for periods greater than 5 minutes. The steady state nature of this method makes longer signal integration times possible in the diffusion analysis embodiment.

Multiple devices of the separation embodiment of this invention can be arranged in series for the continuous mode so that the by-product stream from each device becomes the incoming sample stream to the next. This continuous application produces a series of finely regulated dilutions of the desired particles as well as a substantially clean stream of undesired particles upon exit from the last device of the series. In such an embodiment, the clean undesired particle by-product stream may also be routed to detection elements of the type mentioned above or to particulate sorting devices, counters, or sizing elements, such as a Si microfabricated flow cytometer, e.g. a silicon-based v-groove flow cytometer as described in U.S. patent application Ser. No. 08/534,515 filed Sep. 27, 1995, now U.S. Pat. No. 5,726,751; and 08/621,170 filed Mar. 20, 1996, now U.S. Pat. No. 5,747,349 issued May 5, 1998, incorporated herein by reference, or for further use. For example, in continuous mode, the devices of this invention may be used for dialysis, and the clear plasma stream recycled to a patients body.

The flow rate of the input streams is preferably between about 5 micrometers/second and about 5000 micrometers/ second, more preferably about 25 micrometers/second. Preferably the flow rate for both streams is the same.

The methods and systems of the diffusion analysis embodiment of this invention include determining the concentration of the analyte particles in the sample stream by detecting the position within the laminar flow channel of analyte particles from the sample stream diffusing into the indicator stream causing a detectable change in the indicator stream or in an indicator substance in the indicator stream. The sample stream and the indicator stream may be allowed to reach equilibrium within the laminar flow channel. The location of the boundary of the detection area (i.e. that portion of the indicator stream containing diffused particles at a detectable concentration) with the unaffected indicator stream may be used to provide information about flow speed and/or sample concentration. The physical location of this boundary in the channel for a given analyte stays the same over time as long as the flow speed is constant and the sample unchanged. The location and size of the detection area can be varied by varying flow rate, sample concentration, and/or concentration of an indicator substance so as to optimize the signal for detection.

Information useful for determining the concentration of the analyte particles in the sample stream may be obtained by providing means for conducting specimen streams from the indicator stream at successive intervals along the length of the laminar flow channel, such as smaller channels equipped with viewports as described herein. Detection means such as those listed above are used to measure signals from the indicator stream. Changes in the intensity of the signals from specimen channel to specimen channel may be used to calculate the concentration of analyte particles in the original sample.

Advantages of the diffusion analysis system include the fact that analytes can be determined optically in turbid and strongly colored solutions such as blood without the need for prior filtering or centrifugation; cross-sensitivities of indicator dyes to larger sample components (a common problem) can be avoided; and the indicator can be kept in a solution in which it displays its optimal characteristics (e. g., cross-sensitivities to pH or ionic strength can be suppressed by using strongly buffered solutions). Measurements of the indicator stream at several locations along the channel can compensate for some remaining cross-sensitivities. In addition, the flow channel can be wide, which makes it easy to measure the indicator fluorescence with simple optics. No membrane is needed; the system is less subject to biofouling and clogging than membrane systems. The system is also tunable in that sample or indicator stream concentrations and/or flow rates can be varied to optimize the signal being detected. For example, if a reaction takes about five seconds, the system can be adjusted so that the reaction will be seen in the central portion of the device.

The sample stream may contain particles larger than the analyte particles which are also sensitive to the indicator substance. These do not diffuse into the indicator stream and thus do not interfere with detection of the analyte.

Additionally, a method for determining kinetic rate constants as a function of distance traveled by the input streams from the joint where the two streams meet is provided. Generally, kinetic measurements are made by plotting a physical property related to concentration versus time, i.e., time of reaction. The method provided herein for making kinetic measurements as a function of distance traveled by the sample and indicator stream, rather than as a function of time, is advantageous for the following reasons. The constituents of the streams, i.e., the particles, and the concentrations thereof, at a given position in the flow channel remain constant, given that the flow rate is constant. This method allows for integrating the data from detection, e.g., optical measurements, over time, thereby increasing the accuracy of the data collected and hence of the calculated/determined rate constants. Furthermore, if an experimental error occurs during detection, e.g. in the collection of data, at a given time, one can merely perform the detection measurement again, at the distance/position in the flow channel where the error occurred. In prior art methods of making kinetic measurements, if data at a given time point are lost due to experimental error, those data cannot be collected again during the same experiment.

Further applications of the principles set forth above are described in U.S. patent application Ser. No. 08/656,155 filed May 31, 1996 (now U.S. Pat. No. 5,726,404), U.S. patent application Ser. No. 60/000,281 filed Jun. 16, 1995, and U.S. patent application Ser. No. 08/665,218 filed Jun. 14, 1996 (now U.S. Pat. No. 5,922,210), U.S. patent application Ser. No. 08/621,170 filed Mar. 20, 1996 (now U.S. Pat. No. 5,747,349), U.S. patent application Ser. No. 08/534,515 filed Sep. 27, 1995 (now U.S. Pat. No. 5,726,571), U.S. patent application Ser. No. 08/736,336 filed Oct. 23, 1996 (now U.S. Pat. No. 5,748,827), U.S. patent application Ser. No. 08/823,747 filed Mar. 26, 1997 (now U.S. Pat. No. 6,159,739), U.S. patent application Ser. No. 08/876,038 filed Jun. 13, 1997 (now U.S. Pat. No. 5,971,158), U.S. patent application Ser. No. 08/938,584 filed Sep. 26, 1997, (now U.S. Pat. No. 6,136,272), U.S. patent application Ser. No. 08/938,093 filed Sep. 26, 1997 (now U.S. Pat. No. 6,007,775), U.S. patent application Ser. No. 08/961,345 filed Oct. 30, 1997 (now U.S. Pat. No. 5,974,867), U.S. patent application Ser. No. 08/938,585 filed Sep. 26, 1997, U.S. patent application Ser. No. 08/900,926 filed Jul. 25, 1997 (now U.S. Pat. No. 5,948,684), U.S. patent application Ser. No. 09/080,691 filed May 18, 1998, U.S. patent application Ser. No. 60/067,082 filed Nov. 20, 1997, U.S. patent application Ser. No. 09/196,473 filed Nov. 19, 1998, U.S. patent application Ser. No. 09/169,533 filed Oct. 9, 1998 (now U.S. Pat. No. 6,067,157), U.S. patent application Ser. No. 60/135,417 filed May 21, 1999, U.S. patent application Ser. No. 09/503,553 filed Feb. 14, 2000, U.S. patent application Ser. No. 09/574,797 filed May 19, 2000, U.S. patent application Ser. No. 60/137,386 filed Jun. 3, 1999, and U.S. patent application Ser. No. 09/579,666 filed May 26, 2000, all of which are incorporated herein by reference to the extent not inconsistent herewith.

BRIEF DESCRIPTION OF THE DRAWINGS

FIG. 17 shows a convoluted flow channel in a square wave shape.

FIG. 18 shows a convoluted flow channel in a coiled shape.

FIG. 19A shows a T-sensor with a rounded T-joint.

FIG. 19B shows a viewport-T-sensor with a rounded T joint.

FIG. 21, comprising

FIG. 22, comprising

DETAILED DESCRIPTION OF THE PREFERRED EMBODIMENTS

The microscale channel cells of this invention are useful to separate smaller particles from larger particles in a sample stream based on the fact that the diffusion coefficient of a particle is substantially inversely proportional to the size of the particle so that larger particles diffuse more slowly than smaller particles, on the fact that diffusion occurs more quickly at the microscale of this invention than in larger scale separation devices known to the art and on the fact that laminar, non-turbulent flow can be induced in adjacent streams at the microscale.

Diffusion of small molecules occurs rapidly over typical microfabricated dimensions. The relationship between the size of a particle, $r_a$, the diffusion coefficient, D, and temperature, T, is due to Einstein and for the simplest case, spherical particles, this can be written as:

$$D = \frac{k_b T}{6 \pi \mu r_a}. \qquad (1)$$

The characteristic distance, l, which a particle with diffusion coefficient D will diffuse in time, t, is $$l = \sqrt{Dt}. \qquad (2)$$

Table 2 gives some typical diffusion coefficients and characteristic times.

TABLE 2

Some typical values for different sized particles and molecules. The characteristic time to diffuse 10 μm is given.

| Particle | D(20° C.) | t |
| --- | --- | --- |
| 0.5 μm sphere | 5 × 10⁻⁹ cm²/sec | 200 sec |
| Protein (hemoglobin) | 7 × 10⁻⁷ cm²/sec | 1 sec |
| Small Molecule (fluorescein) | 5 × 10⁻⁶ cm²/sec | 0.2 sec |

Figure 1:
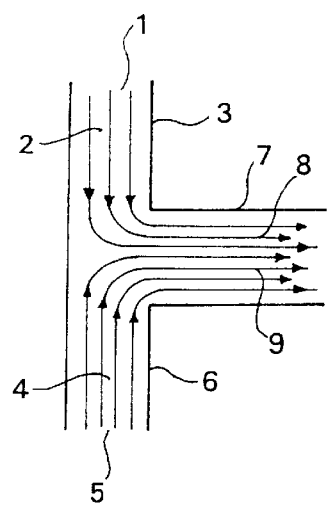
FIG. 1 shows a microchannel configuration showing laminar flow of two input streams having a low Reynolds number.

As shown in FIG. 1, in microchannels of small enough dimensions, inertial effects are negligible, such that a sample stream 2 entering a sample stream inlet 1 can flow from a sample stream channel 3 into an extraction channel 7 without mixing with an extraction stream 4 entering an extraction stream inlet 5 and flowing from an extraction stream inlet channel 6 into extraction channel 7. The two streams in the extraction channel 7 form a laminar sample stream 8 and a laminar extraction stream 9.

Figure 2:
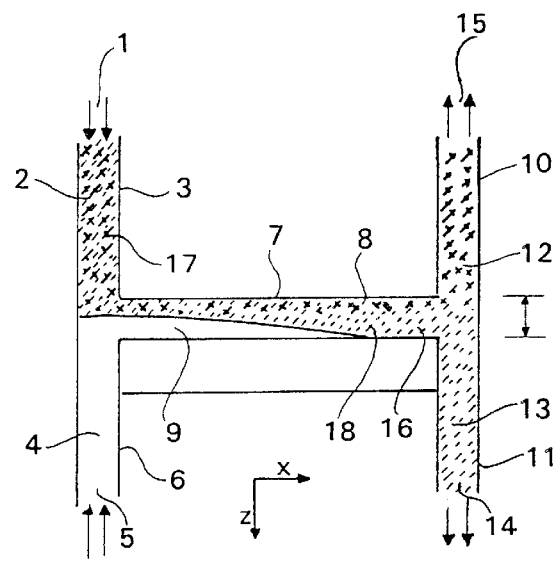
FIG. 2 shows a microchannel configuration illustrating the diffusion of smaller particles from a sample stream into an extraction stream.

In FIG. 2, the arrows at the upper left show the direction of flow in sample stream channel 3 of sample stream 2 entering sample stream inlet 1, and the arrows at the lower left show the direction of flow in extraction stream inlet channel 6 of extraction stream 4 entering extraction stream inlet 5. Sample stream 2 contains larger ("undesired") particles 17 and smaller ("desired") particles 18 (shown by cross-hatching). The sample stream 2 and extraction stream 4 come together in laminar flow in extraction channel 7 to form laminar sample stream 8 and laminar extraction stream 9 and the smaller desired particles 18 begin to diffuse from laminar sample stream 8 into laminar extraction stream 9 to form laminar product stream 16 which contains diffused smaller desired particles 18. The laminar sample stream 8 flows into by-product outlet channel 10 to form by-product stream 12, and leaves the channel through by-product outlet 15. The laminar extraction stream 9 receives smaller desired particles 18 diffused from laminar sample stream 8 and becomes laminar product stream 16 which in product outlet channel 11 becomes product stream 13 and leaves the channel through product outlet 14.

Figure 3:
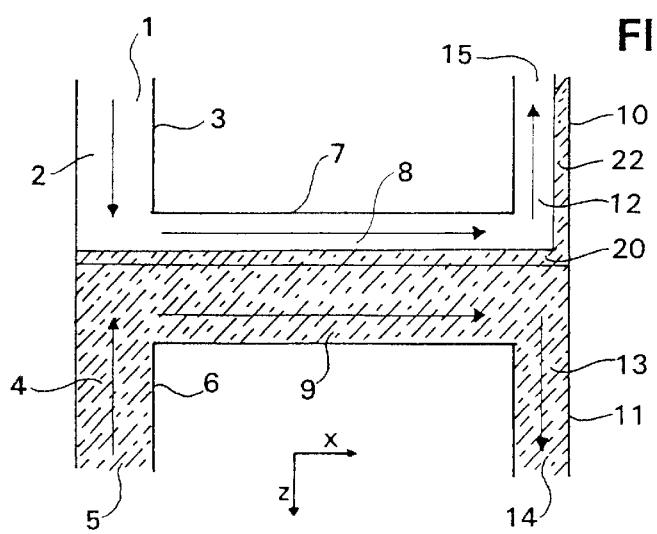
FIG. 3 shows a microchannel configuration illustrating the formation of a fluid barrier between a sample stream and an extraction stream.

In FIG. 3, the direction of the arrow at the upper left shows the direction of flow in sample stream channel 3 of sample stream 2 entering through sample stream inlet 1. The direction of the arrow at the lower left shows the direction of flow in extraction stream inlet channel 6 of extraction stream 4 entering through extraction stream inlet 5. Extraction stream 4 is indicated by cross-hatching. The upper arrow in extraction channel 7 shows the direction of flow of laminar sample stream 8 and the lower arrow in extraction channel 7 shows direction of flow of laminar extraction stream 9. When the volume of extraction stream 4 is greater than the amount which can exit through product outlet channel 11 and product outlet 14, part of laminar extraction stream 9 exits through by-product outlet channel 10 and by-product outlet 15 as excess extraction stream 22. This excess extraction stream 22 is in laminar flow in extraction channel 7 and forms fluid barrier 20. Smaller desired particles 18 (not shown in FIG. 3; see FIG. 2) in the sample stream 2 diffuse from laminar sample stream 8 through fluid barrier 20 into laminar extraction stream 9 to form product stream 16 (not shown in FIG. 3; see FIG. 2).

Figure 4:
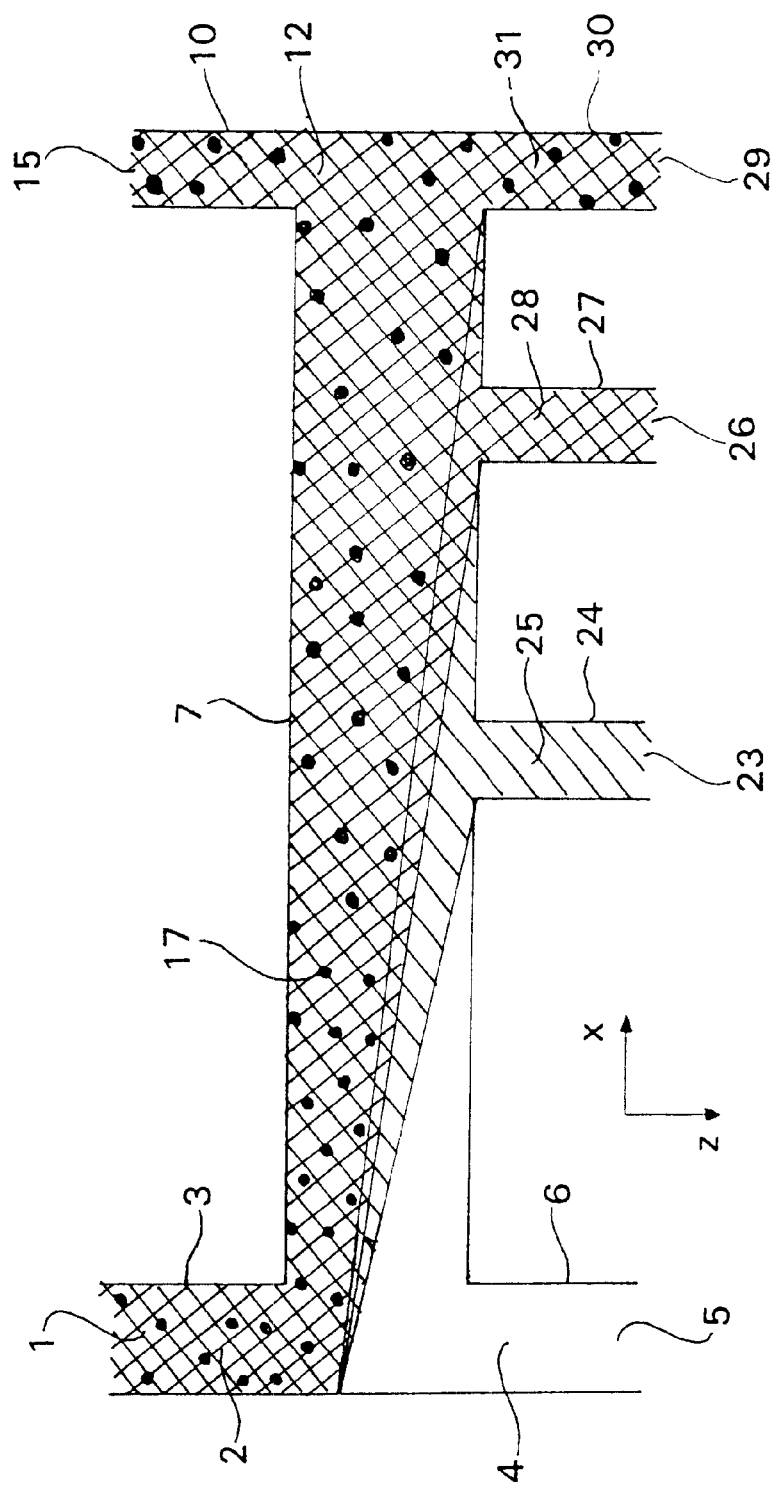
FIG. 4 shows a microchannel configuration (not to scale) illustrating an embodiment of this invention having multiple product channels to separate different sized particles. Black circles represent the largest particle sizes. Diagonal lines running from upper left to lower right represent medium sized particles, and diagonal lines running from lower left to upper right represent the smallest sized particles.

In FIG. 4 another embodiment of the invention is shown. A sample stream 2 containing large particles (black dots), medium-sized particles (diagonal lines from upper left to lower right), and small particles (diagonal lines from lower left to upper right) enters sample stream inlet 1. An extraction stream 4 enters extraction stream inlet 5 and flows to meet sample stream 2 in extraction channel 7. Small particles with larger diffusion coefficients which diffuse most rapidly exit first product outlet 23 in first exiting product stream 25 flowing through first product outlet channel 24 which is placed closest to the sample stream inlet 1. Medium-sized particles with medium-range diffusion coefficients exit along with small particles through second product outlet 26 in second exiting product stream 28 through second product outlet channel 27 placed further from sample stream inlet 1 than first product outlet channel 24 so as to allow more time for medium-sized particles to diffuse into the extraction stream. Large particles which have smaller diffusion coefficients and which diffuse more slowly exit third product outlet 29 in third exiting product stream 31 through third product outlet channel 30, along with small and medium-sized particles. The by-product stream 12 in feed exit channel 10 exiting through by-product outlet 15 also contains particles of all three sizes.

Figure 5:
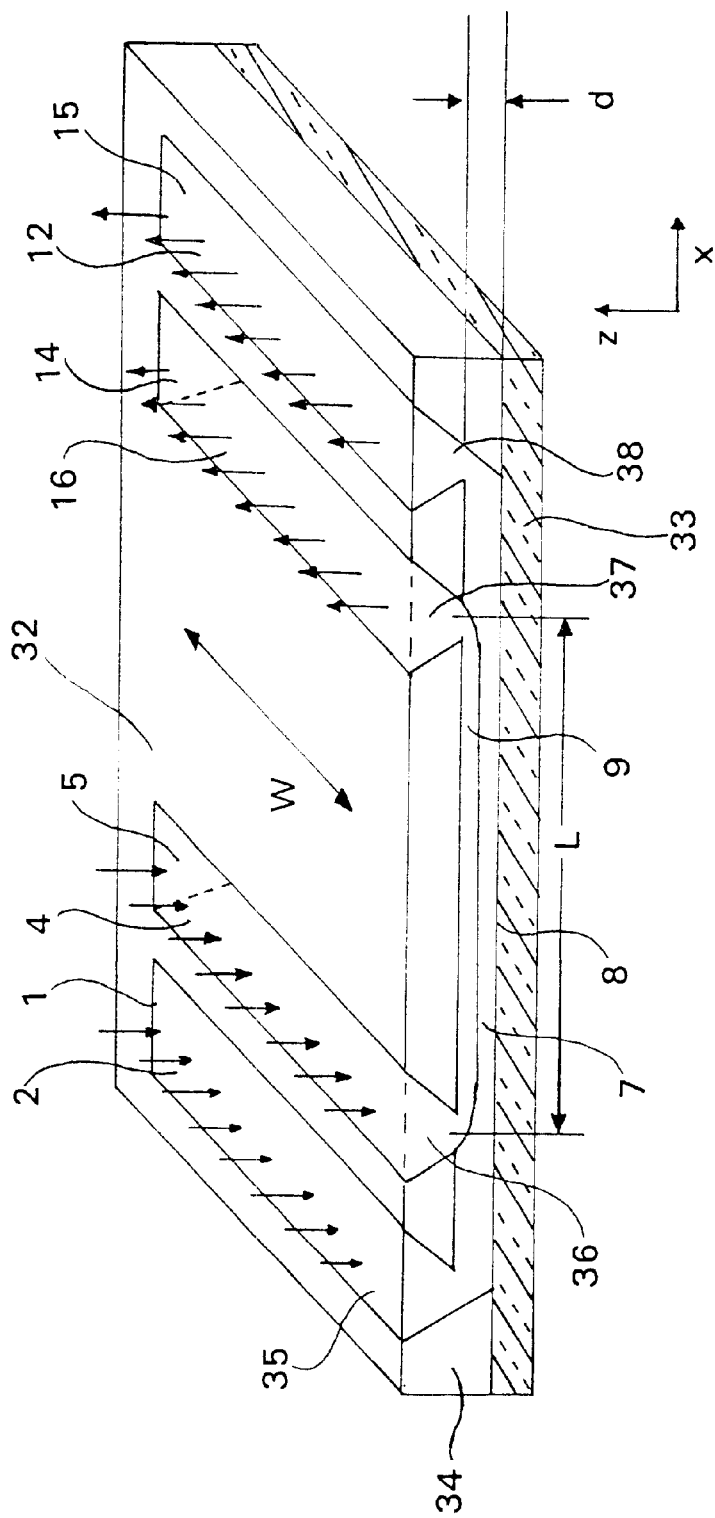
FIG. 5 shows a perspective view of microfabricated flat diffusion extraction system design with the diffusion direction rotated 90° from the "H" design shown in FIGS. 1–4.
Figure 6:
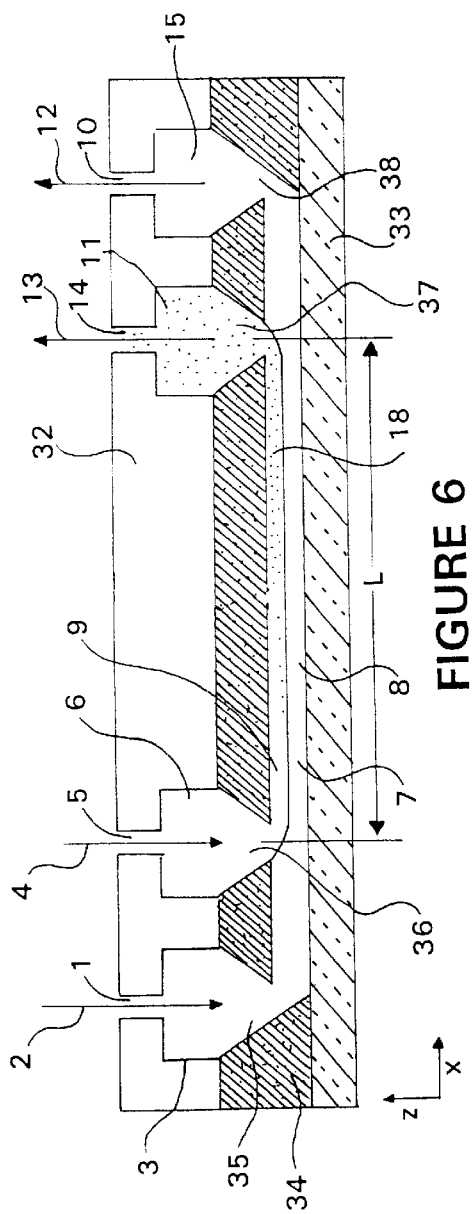
FIG. 6 shows a plan view of the microfabricated flat diffusion extraction system design of FIG. 5.

FIG. 5 shows a perspective view and FIG. 6 shows a plan view of a further embodiment of the invention, a "flat extraction device," in which the diffusion direction in extraction channel 7 is rotated 90° from the embodiments shown in FIGS. 1–4. This embodiment provides the advantage that the volume of material which can be processed is no longer limited by the width of the extraction channel 7.

The flat extraction device of FIGS. 5 and 6 is made by etching a silicon substrate 34 to provide sample stream inlet groove 35, extraction stream inlet groove 36, product stream exit groove 37, and by-product stream exit groove 38, as well as extraction channel 7. A glass cover 33 serves to enclose extraction channel 7. In FIG. 5, the arrows shown pointing downward into sample stream inlet 1 indicate the flow of sample stream 1. Similarly, the arrows pointing down into extraction stream inlet 5 indicate the flow of extraction stream 4. The arrows pointing up from product outlet 14 indicate the flow of product stream 16, and the arrows pointing up from by-product outlet 15 indicate the flow of by-product stream 12. The length of extraction channel 7 is shown as L and the width of the channels is indicated by the dark arrow as w. The depth of the extraction channel 7 is shown as d. A coupling manifold 32 shown in FIG. 6 with openings extends the depth of sample stream inlet groove 35 to form sample stream channel 3 and sample stream inlet 1, extends the depth of extraction stream inlet groove 36 to form extraction stream channel 6 and extraction stream inlet 5, extends the depth of product stream exit groove 37 to form product outlet channel 11 and product outlet 14, and extends the depth of by-product stream exit groove 38 to form by-product outlet channel and by-product exit 15.

In the flat extraction system design shown in FIG. 6 operating by diffusion (concentration gradient) a sample stream 2 shown by the arrow in the upper left enters sample stream inlet 1 and flows in sample stream channel 3. Extraction stream 4 is indicated by an arrow entering extraction stream inlet 5, and flows in extraction stream inlet channel 6. Sample stream 2 flows as a laminar sample stream 8 in extraction channel 7 beneath laminar extraction stream 9. Laminar sample stream 8 is in contact with laminar extraction stream 9 in extraction channel 7 for a length L. Smaller ("desired") particles from laminar sample stream 8 indicated by the stippling in laminar extraction stream 9 flow into product outlet channel 11 as product stream 13 which exits at product outlet 14 as shown by the upward-pointing arrow. By-product stream 12 is the continuation of laminar sample stream 8 past product stream 13 which contains both the larger ("undesired") particles and a portion of the smaller ("desired") particles which have not diffused into product stream 13. By-product stream 12 flows through by-product outlet channel 10 out through by-product outlet 15.

By adjusting the configuration of the channels in accordance with the principles discussed herein to provide an appropriate channel length, flow velocity and contact time between the sample stream and the extraction stream, the size of the particles remaining in the sample stream and diffusing into the product stream can be controlled. The contact time required can be calculated as a function of the diffusion coefficient of the particle D (which generally varies as the linear size of a particle), and the distance d over which the particle must diffuse by $t=d^2/D$. Particles or molecules that have diffusion coefficients larger than D will be in the exiting product stream, and particles or molecules having a diffusion coefficient substantially smaller than D will not. If the diffusion coefficient of the larger particles being separated is about ten times smaller than D, the product should be almost entirely free of the large particles.

A simple calculation shows that few particles or molecules with diffusion coefficients smaller than $D=w_{fb}^2 v/L$ will be found in the exiting product stream, where $w_{fb}$ is the width of the fluid barrier, v is the mean flow velocity of the laminar sample stream and L is the length of the extraction channel. Particles or molecules with diffusion coefficients larger than $D=w^2 v/L$, where w is the width of the extraction channel, will be in the exiting product stream in the same concentration as in the by-product stream.

Means for injecting feed liquid into the device are provided, as when the device of this invention is used as part of an analytical system. Such means include standard syringes and tubes. Means for removing fluid from the product exit may also be provided, including receptacles for the fluid, inducing flow by capillary attraction, pressure, gravity, and other means known to the art as described above. Such receptacles may be part of an analytical or other device for further processing the product stream.

Figure 7:
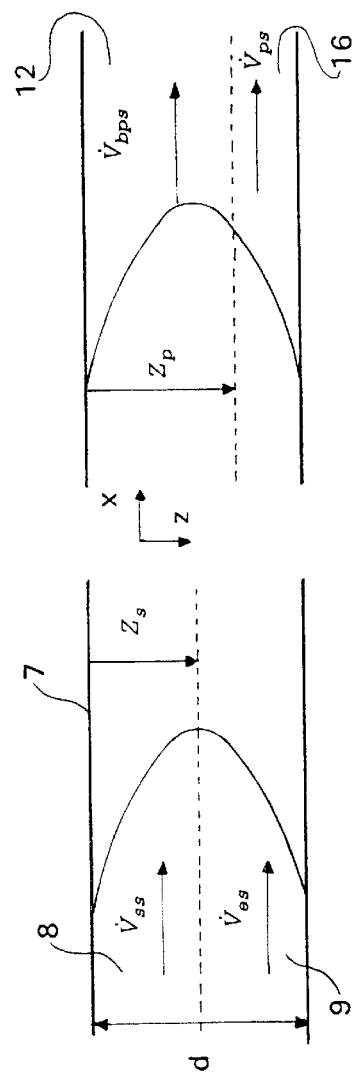
FIG. 7 is a diagram of the entrance and outlet interface streamline in the extraction channel showing the flow rates of the sample, extraction, product and by-product streams.

FIG. 7 shows the extraction channel 7 with laminar extraction stream 9 moving at a velocity $V_{es}$, and laminar sample stream 8 moving at a velocity $V_{ss}$, and having a stream height, (diffusion direction coordinate) $Z_s$ defining the interface streamline location (dotted line) between the laminar sample stream 8 and the laminar extraction stream 9 near the entrance of the extraction channel 7. The combined height of both streams, and thus the depth of the extraction channel 7, is shown as d. The curved line indicates the shape of the velocity profile. As the streams move along the length of the extraction channel 7, laminar sample stream 8 becomes by-product stream 12 moving with a velocity $V_{bps}$ and having a stream height (diffusion direction coordinate) $Z_p$ defining the interface streamline location (dotted line) between the by-product stream 12 and the product stream 13. Laminar extraction stream 9 becomes product stream 13 moving with a velocity $V_{ps}$.

Several steps commonly performed in the chemical assay of a fluid mixture are: (1) precise mixture dilution; (2) extraction of a specific constituent; (3) precise mixing of indicator reagents or test probes (e.g. fluorescently tagged polymer beads); and (4) non-invasive detection of the indicator or probe (e.g. absorbance or fluorescence spectroscopy).

Figure 8:
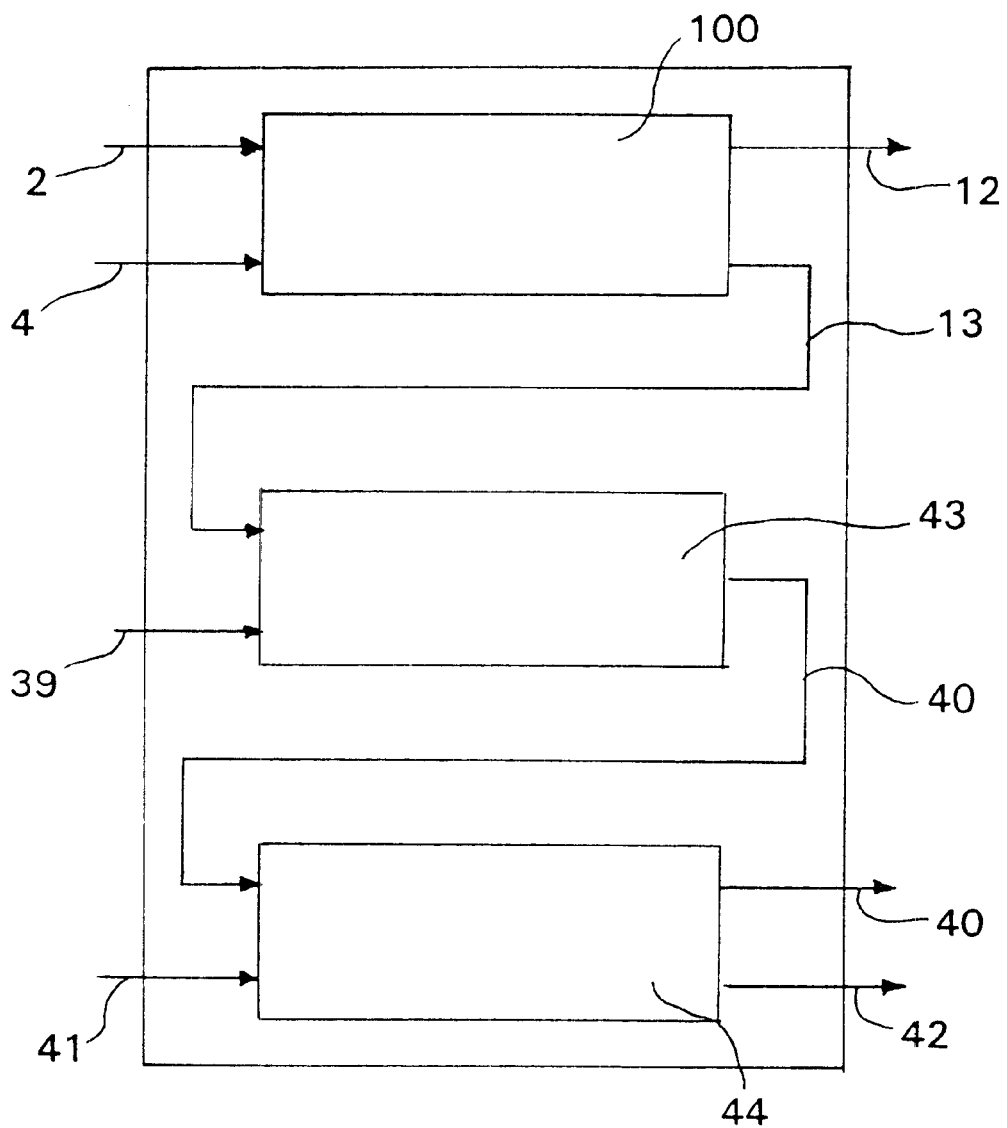
FIG. 8 illustrates the "lab-on-a-chip" concept of this invention for assay of constituents present in a particulate or cell-laden sample stream.

The extraction devices of this invention may be integrated into total analytical systems such as the microfabricated "lab-on-a-chip" illustrated in FIG. 8.

FIG. 8 shows a diffusion-based extraction device 100 of this invention fabricated on a single silicon wafer. A sample stream 2 having a sample stream flow rate $V_{ss}$ and a sample stream constituent i concentration $C_{i,ss}$ flows into the diffusion-based extraction device along with an extraction stream 4 having an extraction stream flow rate $V_{es}$. By-product stream 12 having a by-product stream flow rate $V_{bps}$ and a by-product constituent i concentration $C_{i,bps}$ is removed from the system. Product stream 13 having a product stream flow rate $V_{ps}$ and a product stream constituent i concentration $C_{i,ps}$ flows to a diffusion-based mixing device 43 microfabricated onto the same chip. An indicator dye stream 39 having an indicator dye stream flow rate $V_{ind}$ and an indicator stream dye concentration $C_{dye,ind}$ also flows into the diffusion-based mixing device 43. Detector stream 40 exits diffusion-based mixing device 43 and flows into detection chamber 44 and optical detection means 41 are actuated to detect a signal, preferably a fluorescence signal 42 while detector stream 40 is in the detection chamber 44. Detector stream 40 then exits detection chamber 44 at a detector stream flow rate $V_{ds}$, a detector stream constituent i concentration $C_{i,ds}$ and an indicator dye concentration $C_{dye,ind}$.

The detection strategy presented in FIG. 8 requires constituent extraction from the particulate laden sample, fluorescent indicator mixing with the diluted analyte, and fluorescent optical detection. Critical to the precise operation of the inference technique is the precise regulation of all stream flow rates in the system. Using a calibration between fluorescence intensity and constituent concentration and information precisely defining the constituent extraction and indicator mixing dilution ratios, the concentration of constituent in the original sample stream is estimated. The complete system also includes data reduction, pressure regulation and waste collection. Precise flow control in integrated total analytical systems may in part be achieved using on-chip micro-pumps (Gravesen, P. et al. (1993), "Microfluidics—a review," J. Micromechanics and Microengineering 3(4):168–182; Elwenspoek, M. et al. (1994), "Towards integrated microliquid handling systems," J. Micromechanics and Microengineering 4(4):227–245; and Forster, F. K. et al. (1995), "Design, Fabrication and Testing of Fixed-Valve Micro-Pumps," ASME International Mechanical Engineering Congress & Exposition, San Francisco, ASME).

In both the "H" design for the extraction system, e.g. FIG. 2 as described in the Example, and the flat extraction system of FIGS. 5 and 6, the diffusing constituents migrate into the extraction stream 4 and tend toward an approximate uniform concentration throughout the extraction channel 7. The sample, extraction, and by-product flow rates are externally regulated, thereby fixing the product stream flow rate. In the design of FIG. 2, fabricated as described in the Example hereof, the channel dimension in the diffusion direction (d), is less than 100 $\mu$m in the Example, and the aspect ratio, defined as the channel dimension normal to the diffusion and flow directions (w) divided by the channel depth (d), is less than 1. In the flat diffusion extraction system of FIGS. 5 and 6, the aspect ratio w/d, where d again is less than about 100 $\mu$m, is greater than 1, but still much less than 50.

The distance required for the constituent being extracted to achieve a concentration throughout the microchannel cross section that is within a fixed percentage of the equilibrium concentration is defined as the equilibration length. The constituent concentration within the microchannel is calculated using a 1-D analytical diffusion model. The equilibration length is used to construct a family of process space design curves specific to the extracted constituent. The optimization objective function is specified to identify the design which maximizes the volume flow rate of product stream within constraints imposed by a system microfabricated on a silicon chip.

The methodology is applied to the design of an optimal device for the extraction of albumin (a protein constituent present in human blood) from a carrier sample stream with viscosity approximately that of water. Whole blood typically has a red blood cell (RBC) content of 40–50% by volume, the RBCs having ellipsoidal shape and 8 $\mu$m major axis dimension, and white blood cells having nominal diameters of approximately 15–25 $\mu$m. In this discussion, the analysis is simplified by considering a single viscosity, single diffusivity process model. Considerations relating to multiple viscosity cases are presented hereinafter. The device presented here is specified for a 1% equilibration length (within 1% of the equilibrium concentration of albumin for an infinite length device). This process sensitivity information provides design requirements for upstream and downstream fluidic components and is essential for integration of the device into a "lab on a chip" chemical analysis system.

A process model is defined by its parameters, physical constants, independent variables, dependent variables, and by the equations used to model the process. The extraction process examined in this paper is illustrated below:

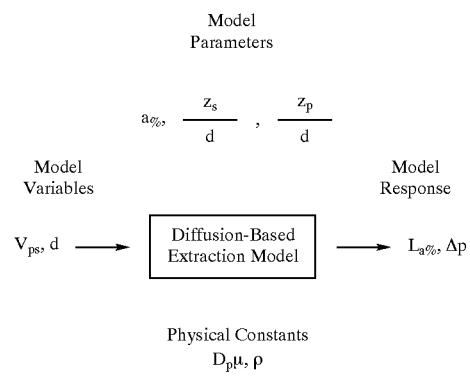

Physical constants cannot be altered with either the design of the device or through its control. There are three physical constants identified above: binary constituent diffusivity, $D_i$; viscosity, $\mu$; and density, $\rho$. The constant parameters are the desired percentage to complete constituent equilibration, $\alpha_\%$, the normalized sample-extraction streamline interface position, $z_s/d$, and the normalized by-product-product streamline interface position, $z_s/d$. The variable model parameters are the product stream flow rate, $V_{ps}$, and the diffusion direction channel depth, d. Under this definition the model outputs are the channel length required to achieve $\alpha_\%$, $L_{\alpha\%}$, and the pressure differential across the extraction channel in the direction of flow, $\Delta p$.

A 2-D flow and constituent transport model of the extraction process is presented. The discussion begins by stating the general 3-D transport problem. Simplifying assumptions are then defined for the 2-D approximations and are applied. Solutions to the resulting descriptive modeling equation and associated boundary conditions are then presented for the inviscid flow case and for a numerical solution to the viscous flow case.

General 3-D Mass Transport Model Equation. The general equation describing the transport of a constituent by both diffusive and convective transport is given as (Cussler, E. L. (1984), *Diffusion. Mass Transfer in Fluid Systems*, Cambridge, Cambridge University Press):

$$\frac{\partial c_i}{\partial t} + v_x \frac{\partial c_i}{\partial x} + v_y \frac{\partial c_i}{\partial y} + v_z \frac{\partial c}{\partial z} = D_i \left[ \frac{\partial^2 c_i}{\partial x^2} + \frac{\partial^2 c_i}{\partial y^2} + \frac{\partial^2 c_i}{\partial z^2} \right] + r_i \quad (3)$$

where: $c_i$ is the concentration of the $i^{th}$ constituent; $D_i$ is the binary diffusion coefficient for the $i^{th}$ constituent; $v_x$, $v_y$, and $v_z$ are the velocity vector components; and $r_i$ is the rate of production of the $i^{th}$ constituent via chemical reactions in the mixture.

2-D Steady Flow Approximation. The mathematical relations representing the modeling assumptions used in this discussion are presented in Equation 4.

$$\frac{\partial c_i}{\partial t} = 0, \quad \text{4(a)}$$

$$\frac{\partial^2 c_i^2}{\partial x^2} = \frac{\partial^2 c_i}{\partial y^2} = 0, \quad \text{4(c)}$$

Equation 4(a) represents the steady state device operation assumption. The extraction device is intended for dynamic operation but steady state operation is used to target a final configuration design configuration. Flow occurs in a single coordinate direction as reflected in Equation 4(b). Equation 4(c) is justified using two arguments: (1) the spatial scale for diffusion is an order of magnitude smaller in the diffusion extraction direction (z-coordinate) than in the channel flow direction (x-coordinate) (the time required for diffusion over a distance 1 is proportional to $l^2/D$); (2) diffusion in the channel width direction (y-coordinate) will tend to flatten the concentration profile in the case of viscous flow and cause the solution to more closely approximate diffusion in the inviscid flow case with identical mean flow velocities. Equation 4(d) is justified in this discussion because there are no chemical equilibrium kinetics reflecting the change of species in the flow stream for the assays of interest considered here. This is not always the case. Application of Equation 4 to Equation 3 yields the simplified relation, $$\frac{\partial c_i}{\partial x} = \frac{D_i}{v_x} \frac{\partial^2 c_i}{\partial z^2}. \quad (5)$$

Non-dimensional Form. Equation 5 can be normalized with respect to the sample stream constituent concentration and the diffusion channel depth by defining the following non-dimensional change of variables, $$\tilde{c}_i = \frac{c_i}{c_{i,0}}, \tilde{x} = \frac{x}{d}, \tilde{z} = \frac{z}{d}, \quad (6)$$

where: $c_{0,i}$ is the concentration of constituent i in the sample stream, and d is the channel depth. Substitution of Equation 6 into Equation 5 yields $$\frac{\partial \tilde{c}_i}{\partial \tilde{x}} = \left[ \frac{D_i}{v_x d} \right] \frac{\partial^2 c_i}{\partial z^2}. \quad (7)$$

The bracketed term in Equation 7 is the inverse of the Peclet number. The Peclet number provides a useful gauge of the relative significance of convective mass transport to diffusion mass transport and is defined as $$Pe = \frac{v_x d}{D_i} \propto \frac{\text{convective transport}}{\text{diffusion transport}}. \quad (8)$$

The concentration is therefore a function of normalized position and the Peclet number, $$\tilde{c}_i(\tilde{x}, \tilde{z}Pe).$$

Steady Flow Entrance Boundary Condition. The position of the streamline separating the sample and extraction streams at the inlet of the extraction device is $z_s$. The boundary condition at the extraction channel inlet, $\tilde{x}=0$, is unity. The extraction stream normalized concentration is zero, $$\tilde{c}_i(0, \tilde{z}) = \begin{cases} 1, & 0 \langle \tilde{z} \langle \frac{z_s}{h} \\ 0, & \frac{z_s}{h} \langle \tilde{z} \langle 1 \end{cases} \quad (9)$$

Infinite Length Channel Far Field Boundary Condition. The far field boundary condition is defined by postulating an infinitely long extraction channel. For such a channel all diffusing constituents must equilibrate across the channel cross-section. Therefore, $$\tilde{c}_i(\infty, \tilde{z}) = \xi \quad (10)$$

where: $\xi$ is the equilibrium normalized concentration. The normalized equilibrium concentration is given as $$\xi = \frac{\dot{V}_{ss}}{V_{ss} + \dot{V}_{ss}} \quad (11)$$

Impermeable Channel Wall Boundary Conditions. During steady state operation of the device adsorption of constituents on the device surfaces is assumed to have equilibrated and therefore the mass flux across a control surface defined by the device boundaries is zero. Therefrom from Fick's law the concentration gradient at the boundary must be zero, $$\frac{\tilde{c}_i(\tilde{x}, 0)}{\tilde{z}} - \frac{\tilde{c}_i(\tilde{x}, 1)}{\tilde{z}} = 0. \tag{12}$$

Inviscid Flow (Plug Flow). If inviscid flow is assumed the velocity across the channel in the z-direction will be constant. With this modeling approximation the location of the streamline interface between the sample and extraction steams is given as $$\frac{z_s}{d} = \xi. \tag{13}$$

The solution to Equation 7 subject to the boundary conditions given by Equation 9, Equation 10, and Equation 12 and the streamline interface location (Equation 9) was derived and is given as $$\tilde{c}_i(\tilde{x}, \tilde{z}) = \xi + \sum_{n=1}^{\infty} \frac{2}{\pi(2n-1)} \sin[(2n-1)\pi\xi]x \tag{14}$$

$$\exp\left[-(2n-1)^2\pi^2\left(\frac{D_i}{v_x d}\right)\tilde{x}\right]\cos[(2n-1)\pi\tilde{z}].$$

Equation 14 was derived using the method of separation of variables. See Folland, G. B. (1992) Fourier Analysis and its Applications, Pacific Grove, Wadsworth & Brooks/Cole Advanced Books and Software, for a detailed presentation of this method and its applications to physical systems.

Viscous Flow—Single Viscosity Fluid. The location of the streamline separating the sample and extraction stream for a viscous flow velocity profile is achieved using conservation of mass. The velocity profile for a single viscosity fluid stream is given as $$v_x(z) = -\frac{d^2}{2\mu}\frac{dP}{dz}\left[\left(\frac{z}{d}\right) - \left(\frac{z}{d}\right)^2\right]. \tag{15}$$

The total volume flow in a channel of depth, d, and width, w, is equal to the sum of the sample and extraction stream flow rates. In terms of the velocity profile this net channel flow rate is given as $$\dot{V}_{ss} + \dot{V}_{es} = w\int_{z=0}^{z=d} v_x(z)dz = -\frac{d^3 b}{12\mu}\frac{dP}{dz} \tag{16}$$

The volume flow rate in the sample stream portion of the extraction channel is given as $$\dot{V}_{ss} = w\int_{z=0}^{z=z_s} v_x(z)dz \tag{17}$$

where $z_s$, is the location of the equilibrium streamline separating the sample and extraction streams. For a viscous flow profile the total sample stream volume flow must reside in the region $0<z<z_s$. Equation 17 may be solved using equations 16 and 15 to yield the cubic relation $$2\left(\frac{z_s}{d}\right)^3 - 2\left(\frac{z_s}{d}\right)^2 + \xi = 0. \tag{18}$$

Any convenient root search technique may be applied to determine the position of the separation streamline separating the sample and extraction streams, $z_s$.

To examine the error associated with assuming inviscid flow a 2-D numerical model was written and used to analyze the flow profile of the "optimal" design suggested by the inviscid flow model. In the numerical simulation model the equation solved is given as $$\frac{\partial^2 \tilde{c}_i}{\partial \tilde{z}^2} = \left[\frac{v_x(\tilde{z})d}{D_i}\right]\frac{\partial \tilde{c}_i}{\partial \tilde{x}}, \tag{19}$$

where the Peclet number is now a function of position within the flow channel due to the viscous flow velocity profile. A centered finite difference in $\tilde{z}$ and upstream difference in $\tilde{x}$ was used to solve the above equation numerically. For $\tilde{z}_s=z_s d=0.5$ a 20% reduction in the required extraction channel length was observed for identical net channel flow rates. Therefore, using the inviscid assumption to generate design curves should give a conservative calculation of the size of the device required for extraction.

Optimization Objective Function. The goal of this design optimization problem was to maximize the volume flow rate of product stream per unit filter channel breadth, w. The function describing this design object is given as $$max\ F(d,L_{\alpha\%})=\dot{V}_{ps}(d,L_{\alpha\%}). \tag{20}$$

where: d is the channel depth, and $L_{\alpha\%}$ is the $a_\%$ equilibration length. Equation 20 describes the design objective and insures maximum device throughput. In other applications competing design objects may also be considered using a multiobjective design objective function where the competing design objectives are ordered using subjective weights to form the composite multiobjective function. On the microscale, in specific applications, it would be advantageous to maximize the ratio of volume flow rate to unit device volume while simultaneously minimizing the surface area to unit device volume (or equivalently maximizing the volume flow rate to unit surface area) of the micro-fluidic device. These ratios are primarily a function of diffusion direction depth which would directly couple into any device design. In addition, it may also be required that the silicon real estate required to realize the device be simultaneously minimized. For each design objective that must be simultaneously optimized, an additional subjective weight is required. Selection of the appropriate weights will vary from one design configuration to another.

Design Constraints. Because the silicon wafers used to produce the micro-fluidic devices are of finite size, there is a practical limit to the maximum allowable filter length.

The $\alpha_\%$ equilibration length, $L_\alpha$, must be less than the maximum practical filter length, $L_{max}$, or $$L_{\alpha-1\%}<L_{max}. \tag{21}$$

Similarly, the channel must be sufficiently deep such that any particulate present in sample and extraction streams will not violate the extraction stream simply due to geometric confinement in the channel, $d>d_{min}$. Further, the channel must not be so deep that the strength of the silicon wafer is excessively compromised, $d<d_{max}$. Combining these two constraints yields the single constraint equation $$d_{min}<d<d_{max}. \tag{22}$$

Finally, the maximum time allowable to complete a set of extraction and subsequent analysis operations will determine a minimum acceptable product stream flow rate for the device. That is, $$\dot{V}_{ps}>\dot{V}_{ps,min}. \tag{23}$$

Figure 9:
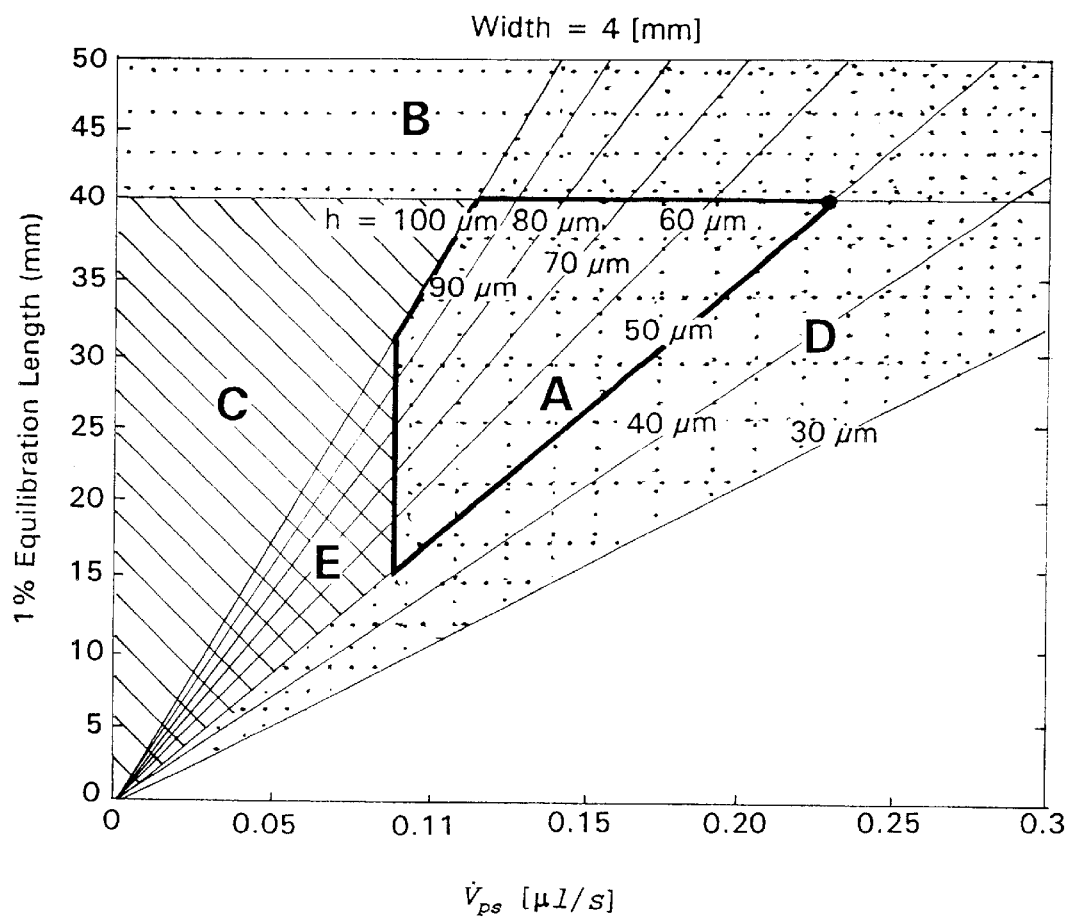
FIG. 9 illustrates optimization of extraction channel length, channel depth and product stream flow rates for a diffusion extraction system microfabricated on a 4 mm wide silicon chip for extracting albumin from a carrier fluid having the viscosity of water.
Figure 10:
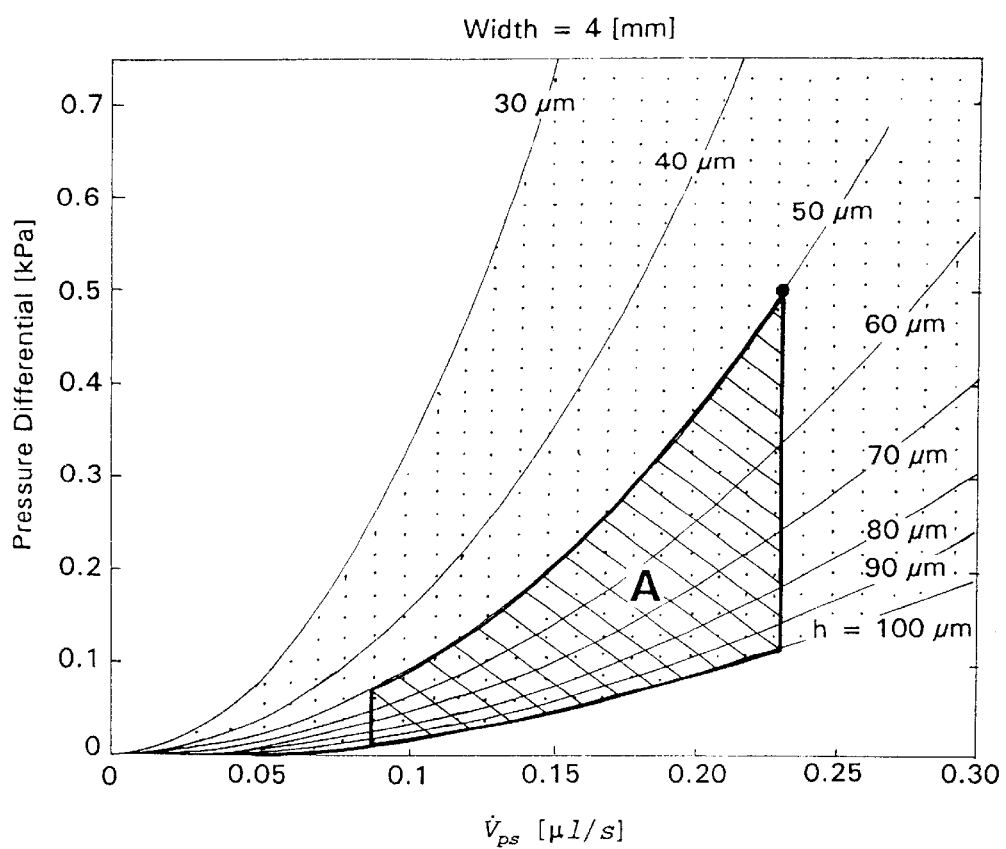
FIG. 10 illustrates optimization of pressure differential, channel depth and product stream flow rates for a diffusion extraction system microfabricated on a 4 mm wide silicon chip for extracting albumin from a carrier fluid having the viscosity of water.

FIGS. 9 and 10 present the process space for a family of diffusion extraction devices designed for $\alpha_{\infty}=1\%$.

FIG. 9 illustrates the design space for a 4 mm wide parallel flow diffusion extraction device to extract albumin from whole blood to achieve a 1% equilibration length, calculated assuming a flow ratio of 1:1 for the sample and extraction stream, and a fluid viscosity of $10^{-3}$ [Pas] and a fluid density of $10^3$ [kg/m$^3$]. The diffusion coefficient for albumin in the saline solution used in this study is $D_{albumin}=7\cdot 10^{-11}$ [m$^2$/s].

The physical constants are $D_i=7\cdot 10^{-11}$ m$^2$/s (albumin), $\mu=10^{-3}$ Pa/s (water), and p=$10^3$ kg/m$^3$(water). These properties are unvarying for a dilute aqueous solution of albumin. The constants would only change if one were to consider another chemical assay. The parameters chosen as fixed for this design optimization are: $\alpha=1\%$; $z_s/d=0.5$; and w=4 mm. These values were chosen as representative for this application and could be varied to achieve specific objectives. For instance, the channel width could be increased to increase the total flow throughput.

In FIG. 9, Area A illustrates the constrained parameters for the process, with the large black dot at the upper right of this area at a channel length of 40 mm, a channel depth 50 $\mu$m, and a product stream flow rate ($V_{ps}$) of about 0.23 $\mu$/s illustrating the most optimal design. Area B, requiring channel lengths greater than 40 mm, is outside the optimal design because these channel lengths exceed the 40 mm width of the silicon chip (L>$L_{max}$). Area C, where the required channel depth is greater than 100 $\mu$m, is outside the optimal design range because the channel depth exceeds that allowable for efficient diffusion (d>$d_{max}$). Area D is outside the optimal design range because the channel is too shallow to pass common cellular constituents (d<$d_{min}$). Area E, where the product stream flow rate 0 to about 0.10 $\mu$l/s is outside the optimal design range because the product flow rate is too small ($Q_{product}<Q_{product.min}$).

FIG. 10 shows the optimal design parameters for conditions as specified in FIG. 9 with respect to the pressure differential across the extraction channel in the direction of flow. Area A, as defined with respect to flow rate and channel depth as described for FIG. 9, is the optimal design area. The large black dot at the upper right of this area again illustrates the most optimal design at a pressure differential of 0.5 kPa.

Equilibration length ($L_{\alpha=1\%}$) is shown to be a linear function of $V_{ps}$ at a given channel depth (d). Equation 14 shows the exponential decay of concentration with $\tilde{x}$. Since the diffusivity is a constant for the given constituent of interest, $v_x$, and d control the rate of exponential decay. The factor $1/Pe=D_i/v_x d$ acts like a time constant. If as d is reduced and $v_x$ is increased to compensate with same 1/Pe resulting, then the $L_{\alpha\%=1\%}$ will remain unchanged. As $V_{ps}$ increases linearly at a given d, $v_x$ increases proportionately and $L_{\alpha=1\%}$ increases linearly due to the linear reduction in 1/Pe. Convection is becoming more important relative to diffusion and a longer channel length is required to reach equilibrium.

To maximize flow rate at a given equilibration length, one would be driven to the upper right hand corner of the constrained process space and operate at a small channel depth (FIG. 9) and high pressure differential (FIG. 10). To minimize area requirements, design to operate in the lower left of FIG. 10 at much lower pressure differentials. One should reduce d as far as possible as long as surface effects can be avoided.

In the following discussion, it is assumed that the two fluids being considered have differing viscosities and are homogeneous, immiscible fluids behaving as Newtonian fluids. To model the two-viscosity case and obtain design parameters and results, three separate steps are required. In what follows, the sample stream is identified as region 2 and the extraction stream is identified as region 1. The ratio of absolute viscosity in region 1 to that in region 2 is m, and location of the fluid interface from mid-channel in the direction of region 1 as a fraction of the half-channel width is $\alpha$. Here the height of the extraction channel is taken as 2$\omega$. The first step is to calculate the velocity profile across both streams in terms of m and $\alpha$. The second step is to use the velocity profiles to determine the numerical values of $\alpha$ and the ratio of mean velocity of each stream given a volume flow ratio $\dot{V}_{es}/\dot{V}_{ss}\equiv F$. The third step is to solve the diffusion equations based on the location of the interface, the mean velocities in each stream, and the diffusion coefficient of the particles of interest in each stream.

To accomplish the first step, the Navier-Stokes equations are solved for one-dimensional two-phase fully-developed steady flow of a Newtonian fluid in a rectangular duct to determine the axial velocity profile u(z). The equations in that case reduce to (White, F. M. (1994) Fluid Mechanics):

$$\nabla p + \mu \nabla^2 u = 0. \quad (24)$$

The resulting velocity profile non-dimensionalized by $\omega^2 \Delta p/\mu_1 L$ and with $\tilde{z}=z/\omega$) measured from mid-channel into region 1 is given by $$\tilde{u}_1(\tilde{z}) = \quad (25)$$
$$\frac{1}{2}\left(-\tilde{z}^2 + \frac{\tilde{z}(\alpha^2 m - \alpha^2 + 1 - m) - \alpha^2 m + 2m + \alpha^2 - \alpha + m\alpha}{m + m\alpha - \alpha + 1}\right) \alpha < \tilde{z} < 1$$

and $$\tilde{u}_2(\tilde{z}) = \quad (26)$$
$$\frac{1}{2}\left(-m\tilde{z}^2 + \frac{m\tilde{z}(\alpha^2 m - \alpha^2 + 1 - m) + m(\alpha^2 m - \alpha^2 - \alpha + m\alpha + 2)}{m + m\alpha - \alpha + 1}\right) -$$
$$1 < \tilde{z} < \alpha.$$

The second step is to calculate the numerical value of $\alpha$ for a particular value of F by solving for $\alpha$ in the equation $$F = \frac{\int_\alpha^1 \bar{u}_1 d\tilde{z}}{\int_{-1}^\alpha \bar{u}_2 d\tilde{z}}, \quad (27)$$

and then with that value of $\alpha$ calculate the ratio of mean flows in each region from $$\frac{\overline{U}_1(1-\alpha)}{\overline{U}_2(1+\alpha)} = F. \quad (28)$$

The last step is to solve the diffusion equation (7) in each region subjected to the boundary conditions given by Eqs. (9), (10), and (12) with two additional interface conditions that require continuity of concentration and conservation of mass of the diffusing species at the interface. Now taking $\tilde{z}$ to be measured from the interface into region 1, those conditions are $$\tilde{c}_{i1}(\tilde{x},0+)=\tilde{c}_{i2}(\tilde{x},0-) \quad (29)$$

and $$D_1 \frac{\partial \tilde{c}_{i1}(\tilde{x}, 0+)}{\partial \tilde{z}} = D_2 \frac{\partial \tilde{c}_{i2}(\tilde{x}, 0+)}{\partial \tilde{z}}. \tag{30}$$

The resulting equation for the mass concentration throughout the channel is given by $$\tilde{c}_i(\tilde{x}, \tilde{z}) = \xi + \sum_{n=1}^{\infty} K_n f_n(\tilde{z}) \exp\left(\frac{-\lambda^2 \tilde{x}}{Pe_1}\right) \tag{31}$$

where $\tilde{x} = x/\omega$, the eigenfunctions $f_n(\tilde{z})$ are given by $$f_n(\tilde{z}) = \begin{cases} \cos k\lambda_n \beta_2 \cos \lambda_n (\tilde{z} - \beta_1) & 0 \langle \tilde{z} \langle \beta_1 \\ \cos \lambda_n \beta_1 \cos k\lambda_n (\tilde{z} + \beta_2) - \beta_2 \langle \tilde{z} \langle 0 \end{cases} \tag{32}$$

the eigenvalues $\lambda_n$ are solutions of the characteristic equation $$\tan \lambda_n(\beta_1) + \sigma \tan k\lambda_n(\beta_2) = 0, \tag{33}$$

the constants $K_n$ are given by $$K_n = 4 \frac{\begin{array}{l}-\xi \cos k\lambda_n \beta_2 \sin \lambda_n \beta_1 + \\ (1-\xi)\sigma \cos \lambda_n \beta_1 \sin k\lambda_n \beta_2\end{array}}{\begin{array}{l}\cos^2 k\lambda_n \beta_2 (\sin 2\lambda_n \beta_1 + 2\lambda_n \beta_1) + \\ \sigma \cos^2 \lambda_n \beta_1 (\sin 2k\lambda_n \beta_2 + 2k\lambda_n \beta_2)\end{array}} \tag{34}$$

with $$\beta_1 = 1-\alpha, \beta_2 = 1+\alpha, k = \sqrt{Pe_2/Pe_1}, \text{ and } \sigma = k(D_2/D_1).$$

Figure 11:
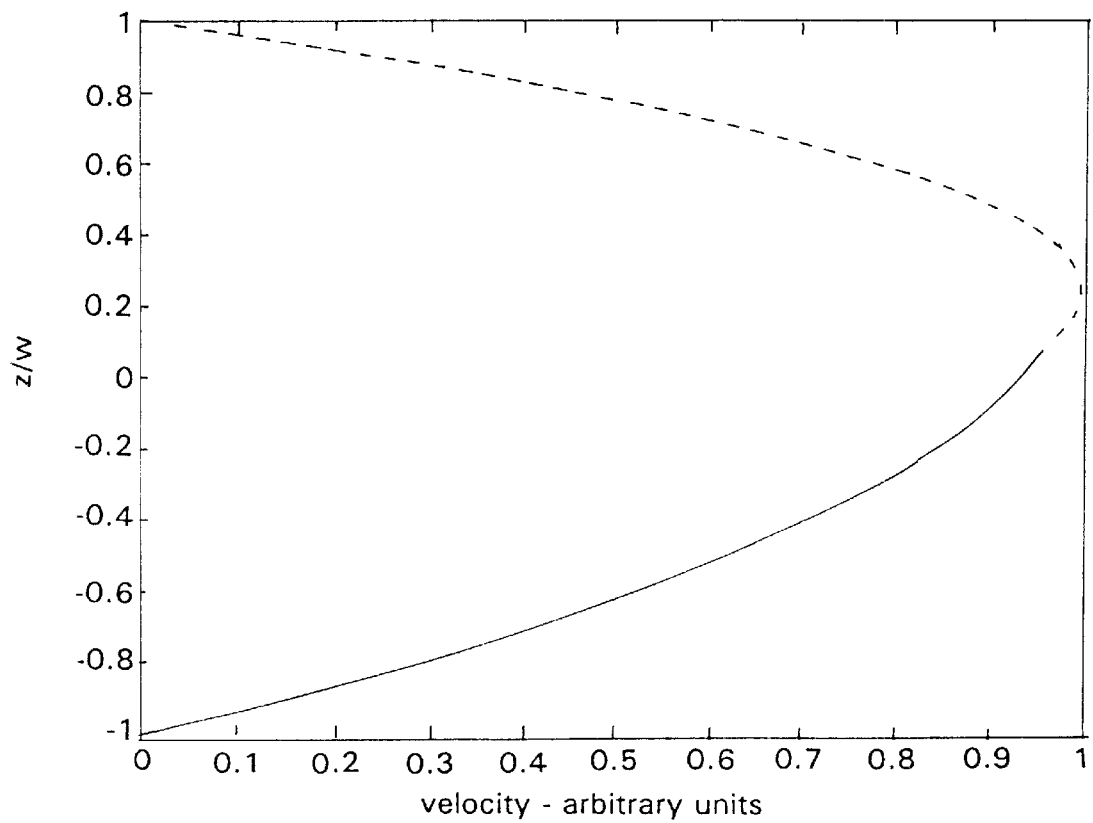
FIG. 11 illustrates the velocity profiles of two homogenous, immiscible fluids behaving as Newtonian fluids but having differing viscosities. The dotted line shows a fluid having the viscosity of water. The solid line shows a fluid having a viscosity three times that of water.
Figure 12:
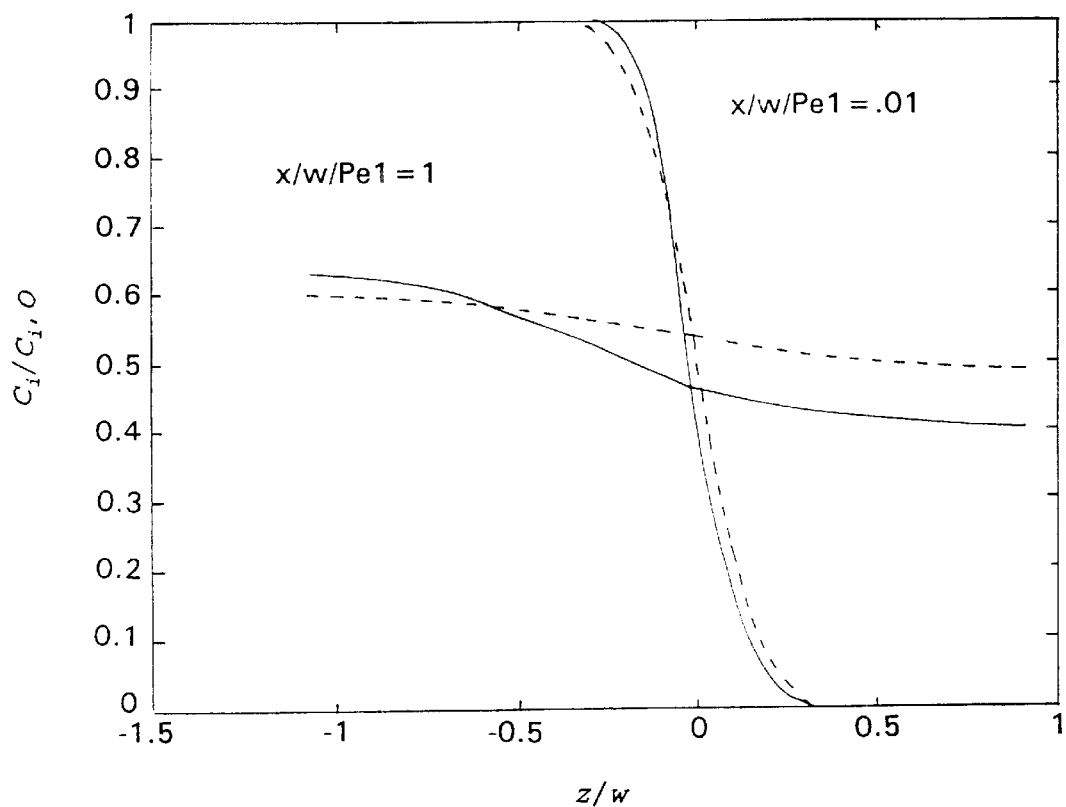
FIG. 12 illustrates a comparison between a two-viscosity model of a diffusion-based extraction system of this invention using the fluids of FIG. 11, and a model assuming the same interface location but with no differences in diffusivity or viscosity in the two fluids.

As an example of the use of the art described above for streams of different viscosity, consider the extraction stream (1) to be water and the sample stream (2) to be a fluid having three times the viscosity of water. Also consider the ratio of volume flow rates to be equal, F=1. Also assume m≠⅓, and $D_2/D_1 \neq ½$. From the equations above α=0.0960, $\overline{U}_1/\!/\overline{U}_2 = 1.21$, and the velocity profile across the channel is shown in FIG. 11. In FIG. 12 a comparison is shown between the two-viscosity model of these fluids and one assuming the same interface location, but with no difference in viscosity or diffusivity in each stream. The comparisons in the concentration across the height of the channel are made near the upstream end of the extraction channel (x/w/Pe1=0.01) and also relatively far downstream (x/w/Pe1=1.0). The two-viscosity calculations are shown as solid lines, and the simpler one-viscosity calculations are shown as dashed lines. Note particularly at the downstream location there is a significant difference between the curves. These results demonstrate the importance of the art as described above for the design and quantitative use of the differential extraction device when used with fluids of different viscosity in each stream.

Figure 13:
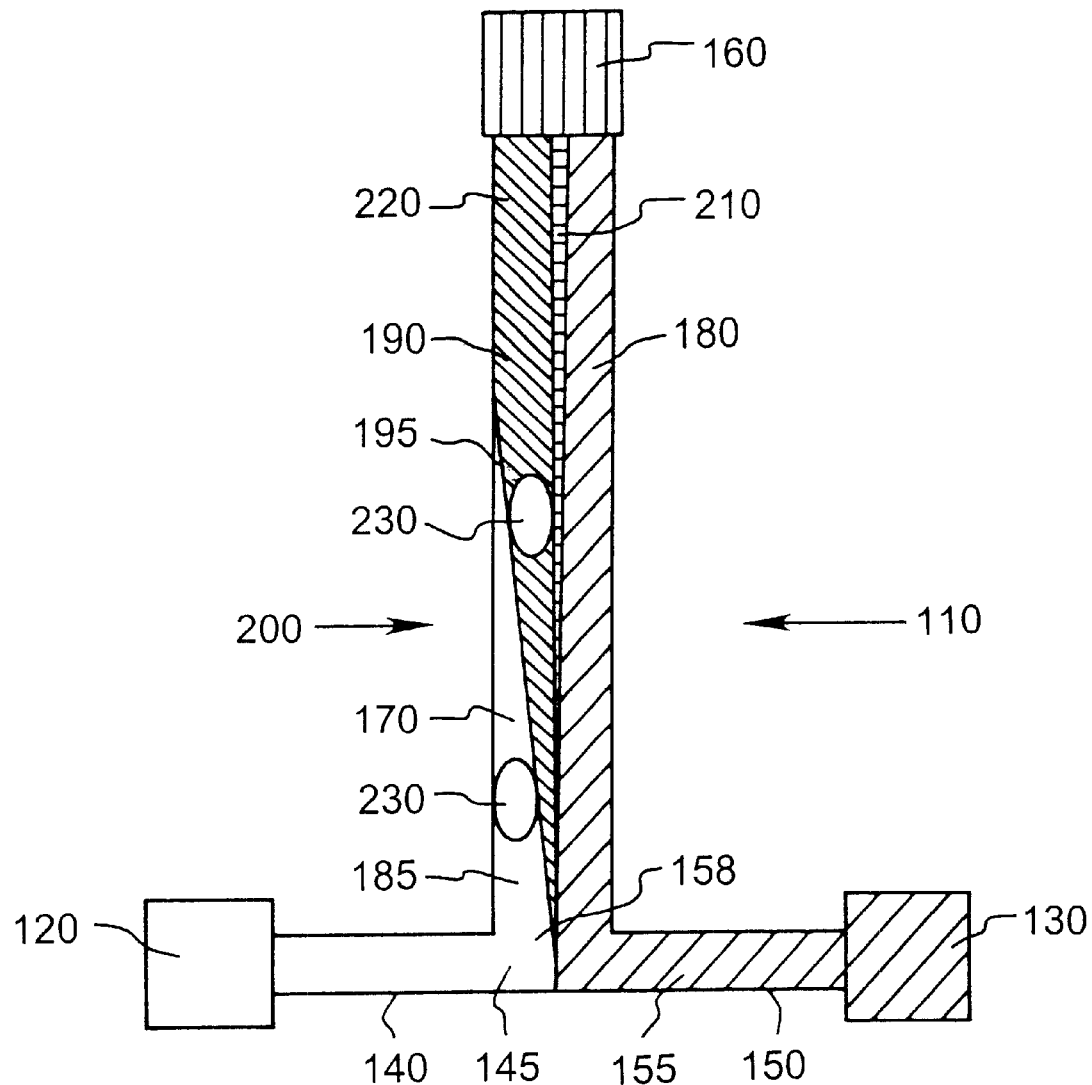
FIG. 13 is a schematic representation of flow and diffusion within the T-sensor channel cell embodiment of this invention.

As shown in FIG. 13, a channel cell in the form of a "T" is provided, referred to herein as T-sensor 110. The device can be microfabricated by etching on a silicon microchip. The geometry need not necessarily be a "T," as a "Y." Any angle that can be fabricated will also suffice. As discussed above, there may be a plurality of input channels. It is necessary only that all input channels merge into a single flow channel, and all channels be sufficiently small that laminar flow is preserved for all operating conditions. In general, the Reynolds number of the system is less than 1.

The sample containing small molecules of interest, sample stream 180, is brought into the device through sample stream inlet port 130, from whence it flows into sample stream inlet channel 150, where it is referred to as sample inlet stream 155. An indicator stream 70 is brought into indicator stream inlet port 120, from whence it flows into indicator stream inlet channel 140, where it is referred to as indicator inlet stream 145.

Sample inlet stream 155 meets indicator inlet stream 145 at T-joint 158 at the beginning of flow channel 200, and the two streams flow in parallel laminar flow as indicator stream 170 and sample stream 180 to exit port 160. The indicator stream 170 contains an indicator substance such as a dye which reacts with analyte particles in the sample stream 180 by a detectable change in physical properties. Indicator stream 70 is shown in white in FIG. 13. Due to the low Reynolds number in the small flow channel 200, no turbulence-induced mixing occurs and the two streams flow parallel to each other without mixing. However, because of the short distances involved, diffusion does act perpendicular to the flow direction, so sample components (analyte particles) diffuse to the left into indicator stream 170 and eventually become uniformly distributed across the width of flow channel 200 at uniform analyte particle diffusion area 220.

The indicator stream 170 flows into flow channel 200 to form an initial reference area 185 into which analyte particles have not yet diffused. Analyte particles from sample stream 180 diffusing into indicator stream 170 form an analyte detection area 190 where analyte particles create a detectable change in the indicator stream 170, preferably by causing a detectable change in property in an indicator substance within the indicator stream 170. Particles of an indicator substance, e.g. dye particles, may also diffuse into sample stream 180 to form a diffused indicator area 210. If this change in local concentration of the indicator substance is a problem in some applications, its diffusion rate can be made arbitrarily small by immobilization on polymers or beads, e.g. indicator beads 230.

In the T-sensor 110 of FIG. 13, a sample stream 180, e.g. blood, and an indicator stream 170 containing an indicator dye are joined at the intersection of sample stream inlet channel 150 and indicator stream inlet channel 140, with flow channel 200 (i.e., T-joint 158) and flow laminarly next to each other in flow channel 200 until they exit the structure at exit port 160. Small ions such as $H^+$ and $Na^+$ diffuse rapidly across the diameter of flow channel 200, whereas larger ions such as the dye anion diffuse only slowly. Larger particles such as sugars, proteins, and the like and blood cells show no significant diffusion within the time the indicator stream 170 and sample stream 180 are in contact with each other. The smaller sample components diffuse more rapidly and equilibrate close to the T-joint 158, whereas larger components equilibrate further up in flow channel 200. Furthermore, as the indicator has a particular half-saturation concentration ($pK_a$, in the case of a pH dye), a front or detection area boundary 195 of indicator dye color or fluorescence change exists as diffusion proceeds up the channel to form detection area 190. In practice the detection area boundary 195 and reference area 185 may form a curved line best seen in FIG. 14. The location and curvature of the front can have its "resting location" adjusted by changing flow speed and channel width to optimize signal size and intensity.

Although this is a flow system, the physical location of the detection area boundary 195 in flow channel 200 for a given analyte stays the same over time as long as the flows are constant and the sample unchanged. Analyte concentration is determined either by monitoring indicator signal at uniform analyte particle diffusion area 220 after substantial equilibration, or by noting the position of the front of steepest indicator color change, for example with a multi-element detector (see FIG. 15). The analyte detection area 190 can be as large as necessary to provide a detectable indicator signal. Similarly reference area 185 can be made to be as large as necessary to provide a detectable reference signal. Adjustments of these areas can be made as described below based on the diffusion coefficients of the analyte and indicator substance, flow rates and channel sizes.

Figure 14:
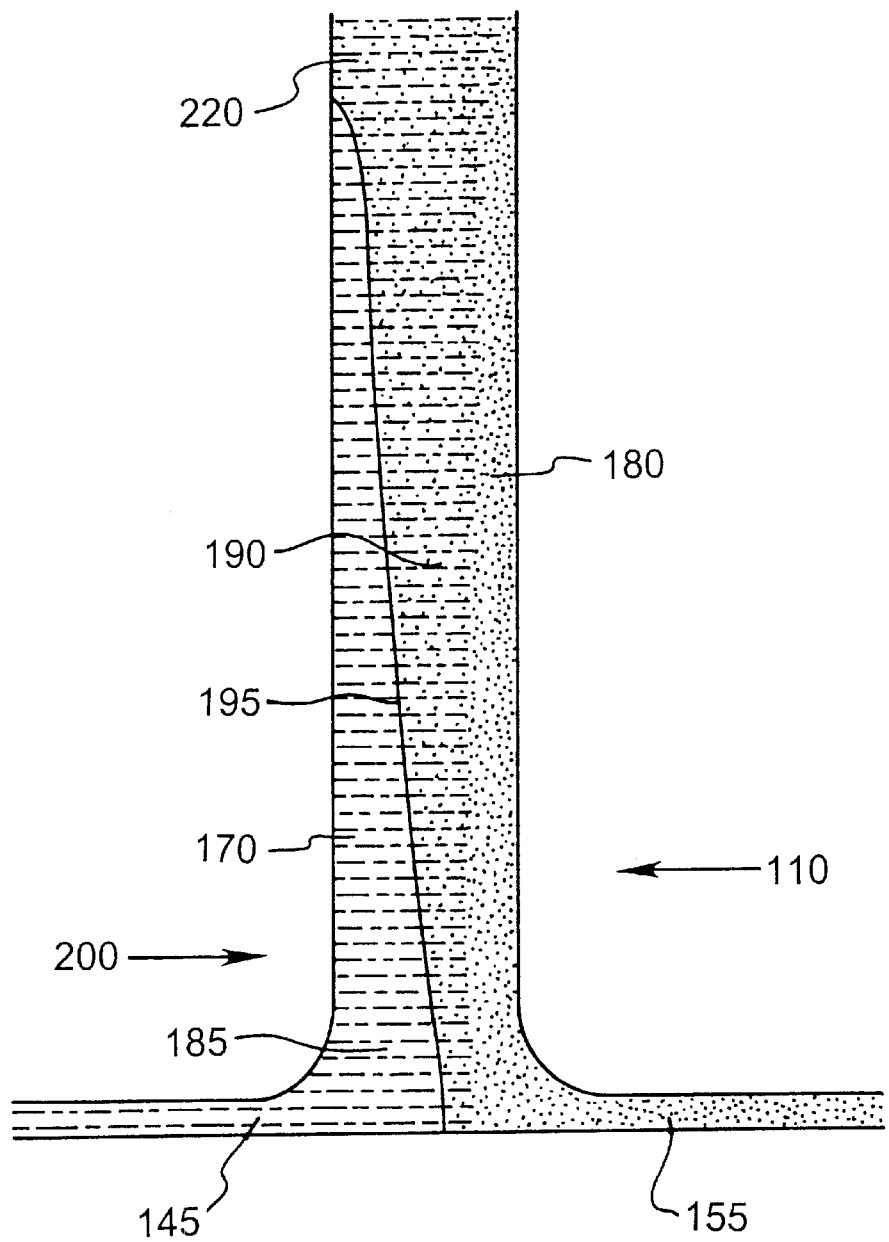
FIG. 14 is a fluorescence micrograph of a T-sensor of this invention in which a buffer solution of pH 9 (right inlet) is flowing into the device, and a weakly buffered indicator dye solution (pH 5) enters from the left. The distinct conversion of the dye from one form to the other as diffusion proceeds is clearly visible.

FIG. 14 shows a fluorescence microscope photograph of the T-sensor of FIG. 13 featuring an indicator inlet stream 145 which is a weakly buffered indicator dye solution of pH 5, and a sample inlet stream 155 which is a buffer solution of pH 9. The bright zone at the right is light reflecting on the silicon and does not relate to the sample and indicator streams. The sample stream 180 appears as a dark clear fluid on the right. The bright zone on the left is reference area 185 where analyte particles have not yet diffused into indicator stream 170. The grey area in the middle is analyte detection area 190 where OH⁻ ions from the sample stream 180 have diffused into indicator stream 170 to form detection area 190. The fuzzy right edge of the grey detection area 190 is caused by dye particles diffusing into the sample stream 180. Uniform analyte particle diffusion area is shown at 220 where the OH⁻ ions are uniformly diffused. The strongest signal is in the middle of detection area 190.

Figure 15:
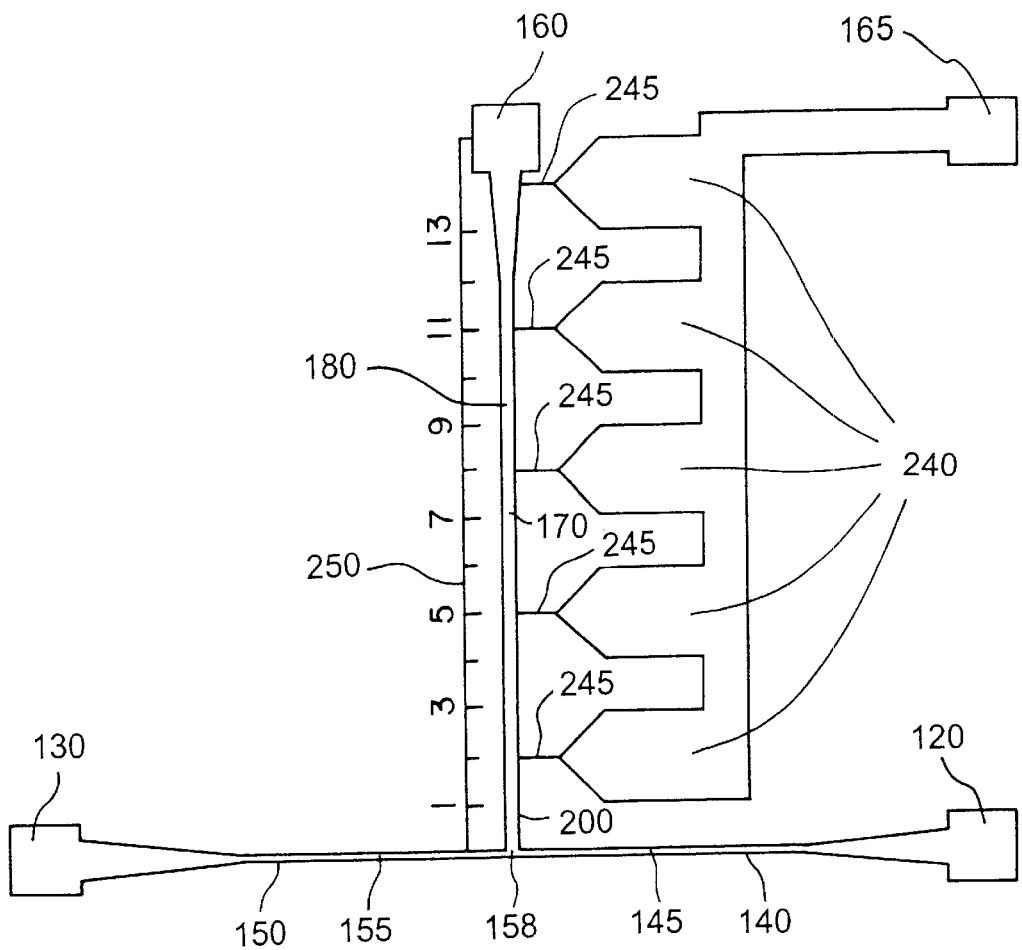
FIG. 15 shows the layout of the viewport-T-sensor embodiment of this invention. In this embodiment the indicator stream comes from the right T-leg, and is a solution of indicator dye in a low ionic strength buffer of pH 9. The sample stream, which is introduced from the left, here is a 0.15 M buffer solution of pH 5. Several portions of the indicator stream which contains the indicator dye are continuously taken out of the channel as specimen streams at various locations.

FIG. 15 shows another embodiment of the T-sensor channel cell device of this invention having multiple specimen channels and viewports spaced along the length of the flow channel. In FIG. 15 an indicator inlet stream 145 enters from the right (rather than the left as in FIGS. 13 and 14) at indicator stream inlet port 120. A solution of indicator dye in a low ionic strength buffer of pH 9 is used. A sample inlet stream 155 which is a 0.15 M buffer solution of pH 5, enters from the left at sample stream inlet port 130. The concentration of the dye is only about 10% of the dye concentration used in FIG. 14. The indicator and sample streams 145 and 155 respectively, flow along indicator stream inlet channel 140 and sample stream inlet channel 150 respectively, to meet at T-joint 158 and flow laminarly together along flow channel 200. Specimen streams 245 from indicator stream 170 which contain the indicator dye are continuously taken out of flow channel 200 at various locations. These specimen streams 245 flow through widenings which serve as viewports 240. Due to the size of the viewports 240 (several square millimeters), the fluorescence intensity can be easily monitored through a fluorescence microscope, or directly with a photodetector.

The viewport closest to T-joint 158 contains mainly undisturbed dye solution, whereas the viewport closest to exit port 160 contains the sample stream 180 completely equilibrated with the indicator stream 170. The viewports in between contain the indicator stream 170 in various degrees of equilibration with the sample components. The closer to T-joint 158, the more likely the viewport is to contain only small ions from the sample. A fluorescence micrograph of the viewports shows that the color in the viewport closest to T-joint 158 is the red color of the base form of the undisturbed indicator dye, whereas the yellow-green color of the viewports closest to exit port 160 represent the acid form of the dye, after the pH of the indicator stream 170 was altered from basic to acidic when diffusion-based equilibration has been reached.

The viewport T-sensor of FIG. 15 lends itself to simple referencing techniques. The integral fluorescence intensity of each viewport at one or more wavelengths can easily be measured through a fluorescence microscope, or directly, with photodiodes. In the easiest case, with an indicator dye showing no cross-sensitivity to other sample components, the intensity ratio between selected viewports gives a measurement value largely independent of dye concentration and excitation light intensity. Measuring at more than one viewport increases the redundancy and therefore the measurement accuracy.

In cases of cross-sensitivity of the indicator to larger sample components (e.g. larger biomolecules such as albumin), this interference can be referenced out by comparing the ratios of the different viewports. The viewports closer to T-joint 158 will contain mainly smaller sample components, whereas the viewports further up flow channel 200 will also contain larger particles.

The T-sensor device of the present invention can be used with reporter beads to measure pH, oxygen saturation and ion content, in biological fluids. (U.S. patent application Ser. No. 08/621,170 "Fluorescent Reporter Beads for Fluid Analysis," now U.S. Pat. No. 5,747,349, which is incorporated by reference herein in its entirety, discloses fluorescent and absorptive reporter molecules and reporter beads.) Reporter beads can also be used to detect and measure alcohols, pesticides, organic salts such as lactate, sugars such as glucose, heavy metals, and drugs such as salicylic acid, halothane and narcotics. Each reporter bead comprises a substrate bead having a plurality of at least one type of fluorescent reporter molecules immobilized thereon. Plurality as used herein refers to more than one. A fluorescent property of the reporter bead, such as intensity, lifetime or wavelength, is sensitive to a corresponding analyte. Reporter beads are added to a fluid sample and the analyte concentration is determined by measuring fluorescence of individual beads, for example, in a flow cytometer. Alternatively, absorptive reporter molecules, which change absorbance as a function of analyte concentration, can be employed. The use of reporter beads allows for a plurality of analytes to be measured simultaneously, and for biological cells, the cell content can also be measured simultaneously. A plurality of analytes can be measured simultaneously because the beads can be tagged with different reporter molecules.

The fluorescent reporter molecules of this invention can be any fluorescent molecules having fluorescence properties which are a function of the concentration of a particular analyte or class of analytes. Many dyes and fluorochromes known in the art can be used as reporter molecules in this invention (see, for example, R. P. Haugland, Handbook of Fluorescent Probes and Research Chemicals, 5th Edition, Molecular Probes Inc., Eugene, 1992). The criteria for reporter molecule selection are that the molecules can be immobilized on a substrate bead and that their fluorescence is a function of the concentration of an analyte. In contrast with previously used fluorescent beads, wherein the number of beads in an aggregate changes, the reporter beads of U.S. patent application Ser. No. 08/621,170, now U.S. Pat. No. 5,747,379, are not required to have an immunoreagent, such as a ligand, antiligand, antigen or antibody, on the surface in combination with the reporter molecules.

Fluorescent reporter molecules interact with the analyte in a way that changes the fluorescent properties of the reporter molecule. In some instances the reporter molecule reacts with the analyte, as in the case of albumin detection by AB 580 (Molecular Probes). In some cases the interaction is not a chemical reaction. For example the reporter molecule fluorescence can be quenched by nonradiative energy transfer to the analyte, as in the case of $O_2$ detection by ruthenium diphenyl phenanthroline. For some reporter molecules the fluorescence is sensitive to polarity changes in the fluid, which can be used to detect organic solvents and hydrocarbons within an aqueous fluid. The interaction can also be through other solvent effects, wherein the ionic strength of the solvent affects the fluorescence. Solvent effects can be used to determine the total concentration of all dissolved ions. The interaction can be a ligand/antiligand or antigen/antibody reaction. The interaction preferably does not lead to an aggregate with other particles and, in particular, does not create an aggregate containing a plurality of reporter beads. It is preferred that the interaction of the analyte with the reporter molecules does not significantly perturb the analyte concentration in the fluid.

In the case of fluorescent reporter beads, at least one fluorescence property of the reporter molecules is a function of analyte concentration. The property measured for the reporter beads can be any property which is affected by the analyte interaction with the beads, such as the fluorescence intensity, decay time or spectrum.

Alternatively, the reporter molecules can be absorption indicators, for example the physiological pH indicator N9 (Merck, Germany) immobilized on a substrate bead. Such indicators change their absorption as a function of analyte concentration. Typically the color of the molecules changes (i.e., the wavelength of their absorption maximum changes).

Absorptive reporter molecules can be used in combination with fluorescent reporter molecules on a substrate bead, and absorptive beads can be used in combination with fluorescent beads.

The substrate bead function is to allow the detection of an analyte, and optionally its concentration, with optical measurements of single beads. More than one type of reporter bead, i.e., beads with different reporter molecules immobilized thereon, can be used to analyze a given sample, provided that the bead type can be identified. Beads can be identified by various means, including means employing bead size, e.g., light scattering; fluorescent tag(s) attached to the bead which has a different excitation and/or emission wavelength from that of the fluorescent reporter molecule attached to that bead; or by directly identifying the fluorescent molecule attached to the bead. This allows for detection of more than one analyte at a time. The substrate bead also functions to immobilize the reporter molecules to prevent their diffusion into the sample stream. The reporter molecules can be on the surface of or within the substrate bead. The beads can be fabricated from a variety of materials and can have any shape, not limited to spherical. Suitable materials include glass, latex, hydrogels, polystyrene and liposomes. The beads can have added surface groups to facilitate attaching reporter molecules, such as carboxyl groups on latex and amino-modified polystyrene.

Various techniques can be employed to immobilize the reporter molecules on the substrate bead. Adsorption based coatings can be prepared by immersing the substrate beads in a reporter molecule solution and then washing off excess reporter molecules. Reporter molecules can similarly be diffused into the cavity of controlled pore glass beads. Reporter molecules can also be covalently immobilized by chemically attaching them to functional groups of suitable substrate beads. Polymerized beads can be formed in a solution containing reporter molecules, thereby trapping the molecules in a fixed polymer cavity. To immobilize reporter molecules in a liposome, lipids can be mixed with a reporter molecule solution, the solution shaken, and the liposomes separated.

To employ reporter beads in the methods of this invention, the beads are mixed with a fluid sample and the fluorescence or absorption of individual beads is measured. The beads can be dry before mixing with the sample or can be dispersed in a fluid. For microscale measurements it is preferred that the added volume of beads and any accompanying fluid be small compared to the sample volume (for example <1%) so that sample dilution is insignificant.

The channel cells of this invention may be formed by any techniques known to the art, preferably by etching the flow channels onto the horizontal surface of a silicon microchip and placing a lid, preferably of an optically clear material such as glass or a silicone rubber sheet, on the etched substrate. Other means for manufacturing the channel cells of this invention include using silicon structures or other materials as a template for molding the device in plastic, micromachining, and other techniques known to the art. The use of precision injection molded plastics to form the devices is also contemplated. Microfabrication techniques are known to the art, and more particularly described below.

In a preferred embodiment of this invention, channel cells of this invention have hydrophilic surfaces to facilitate flow of liquid therein and allow operation of the device without the necessity for pressurization. The substrate may be treated by means known to the art following fabrication of the channels, to render it hydrophilic. The lid is also preferably treated to render it hydrophilic.

The channel systems of this invention can be in fluid connection with one or more v-groove channels. A silicon microchip can be etched to form a v-groove with reflective surfaces/walls of the channels. Thus, optical measurements can exploit reflected, rather than transmitted, incident light. Detection can be achieved by reflection, that is by detecting reflected light. Small angle scattered light (scattered off the surfaces of any particles in the channel) is also reflected by the v-groove wall and can be collected by a small angle photodetector. Large angle scattered light and fluorescent light can exit the channel without reflection and can be collected by the a large angle photodetector. In addition, the reflective wall of the v-groove behind the illuminated particle enhances the fluorescence collection efficiency. Any part of the incident light, e.g., laser beam, that is not within the v-groove channel is reflected from the silicon surface in a direction away from either the small or large angle detectors. The fraction of light reflected from the lid, e.g., transparent cover plate, in a case wherein light enters from air without being directly coupled into the lid/cover plate, is also directed away from the small and large angle detectors thereby reducing undesirable background light intensity from the measurements.

Because the v-groove flow channel reflects the incident light, rather than transmitting it, fabrication of the microchannel system of this invention is extremely simple. The microchannel is fabricated from a single microchip of silicon which is patterned on a single side. A transparent cover plate is attached to the top of the microchip to seal the channel.

Figure 16:
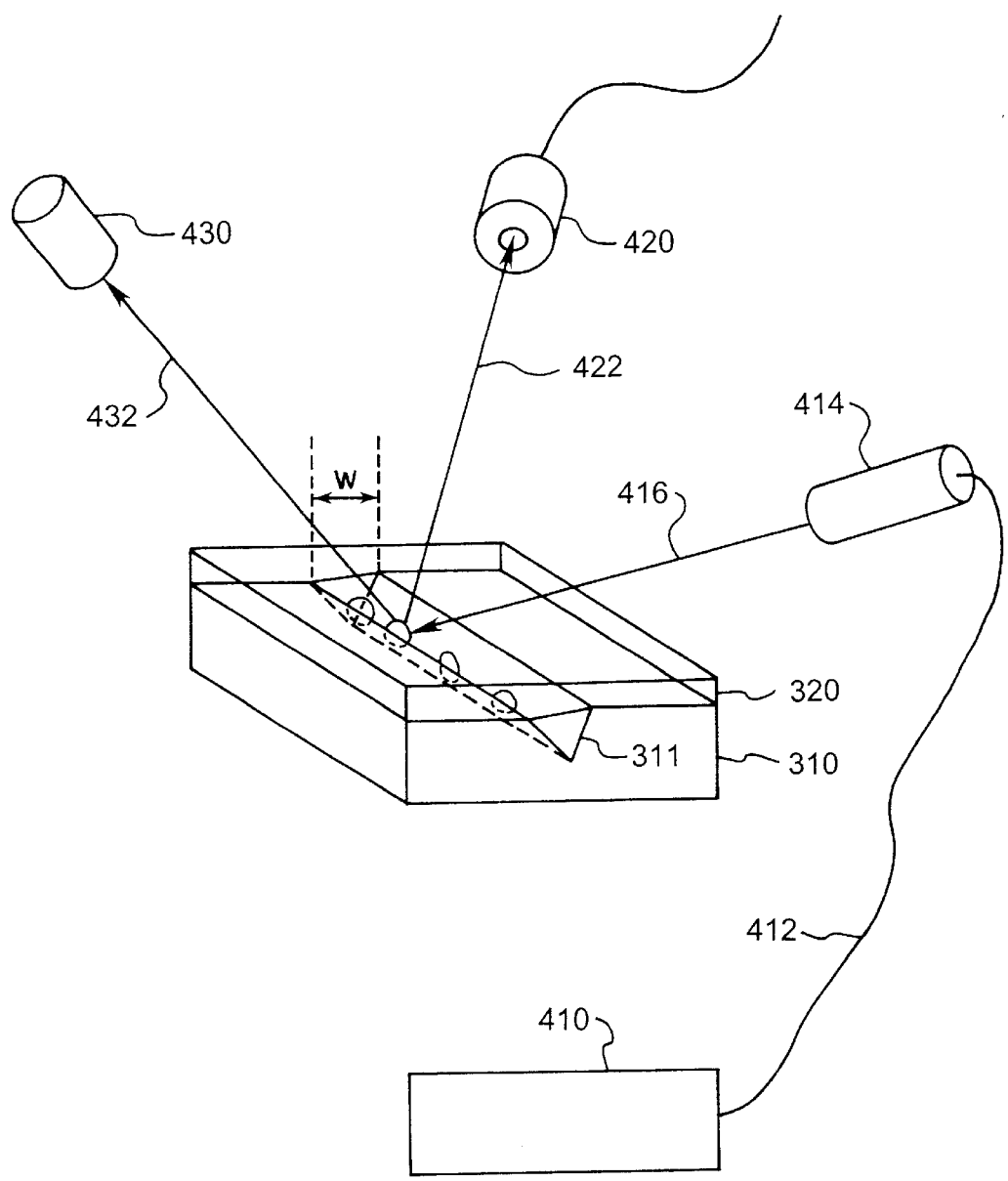
FIG. 16 shows a v-groove flow channel coupled with a flow cytometer optical head.

FIG. 16 shows a v-groove flow channel and optional optical head. Silicon microchip 310 has v-groove 311 therein. The term v-groove is used herein for a substantially "V" shaped groove in the surface of a silicon microchip. Depending on the fabrication process the point of the "V" can be flat (a trapezoidal groove), but only if the flat portion does not fall within the analyte detection area defined by the interception of the illumination beam with the sample flow. In a preferred embodiment, microchip 310 has a <100> surface orientation and the walls of groove 311 are along <111> planes, providing an angle of 54.7° between the walls of the groove and the plane of the surface of the microchip. Transparent cover plate 320 is sealed to the surface of microchip 310. In a preferred embodiment the cover plate is made of pyrex and is anodically bonded to the silicon microchip. In the illustrated embodiment the light source includes diode laser 410, optical fiber 412 and focusing head 414. Non-scattered light, i.e., light which has not been scattered by a particle, is specularly reflected by a wall of channel 311 and travels along path 422. Small angle (forward) scattered light deviates slightly from path 422 and impinges on small angle detector 420. Some of the light scattered at large angles travels along path 432 to large angle photodetector 430. The photodetectors can be photodiodes or photomultipliers. Large angle detector 430 can be used to measure large angle scattering and/or fluorescence.

Means for applying pressure to the flow of the feed fluids through the device can also be provided. Such means can be provided at the feed inlets and/or the outlet (e.g. as vacuum exerted by chemical or mechanical means). Means for applying such pressure are known to the art, for example as described in Shoji, S. and Esashi, M. (1994), "Microflow devices and systems," J. Micromechanics and Microengineering, 4:157–171, and include the use of a column of water or other means of applying water pressure, electroendoosmotic forces, optical forces, gravitational forces, and surface tension forces. Pressures from about $10^{-6}$ psi to about 10 psi may be used, depending on the requirements of the system. Preferably about $10^{-3}$ psi is used. Most preferred pressures are between about 2 mm and about 100 mm of water pressure.

An example of an embodiment using multiple streams is a channel cell having three inlet streams flowing in laminar flow wherein the middle stream is a reagent stream. For example, the sample stream may be blood, the middle stream glucose oxidase, and the third stream an indicator stream containing pH sensitive dye. As glucose particles diffuse through the reagent stream they are changed to gluconic acid which is detected by a pH-sensitive dye when the gluconic acid molecules diffuse into the indicator stream. Other examples of multiple-stream systems include systems having several sample streams with analyte at different concentrations for calibration of the detection means. Indicator streams not adjacent to the sample streams may also be used as control streams.

The indicator stream can be measured by the detection means before and after diffusion of particles into the stream has taken place, and such measurements as well as the rate of change of the indicator stream along its length can be used to assay analyte concentration. In addition, multiple detection means of different types can be used to measure the indicator stream. Field effects which are ion or chemical sensitive can be measured at different locations in the device.

The channel cells of this invention and the channels therein can be sized as determined by the size of the particles desired to be detected or separated. As is known in the art, the diffusion coefficient for the analyte particles is generally inversely related to the size of the particle. Once the diffusion coefficient for the particles desired to be detected is known, the contact time of the two streams, size of the central channel, relative volumes of the streams, pressure and velocities of the streams can be adjusted to achieve the desired diffusion pattern.

The Reynolds number is the ratio of inertial forces to viscous forces. As the Reynolds number is reduced, flow patterns depend more on viscous effects and less on inertial effects. Below a certain Reynolds number, e.g. below about 1, (based on lumen size for a system of channels with bends and lumen size changes), inertial effects can essentially be ignored. The microfluidic devices of this invention do not require inertial effects to perform their tasks, and therefore have no inherent limit on their miniaturization due to Reynolds number effects. Applicants' channel cell designs, while significantly different from previous reported designs, operate in this range. These microfluidic devices of this invention require laminar, non-turbulent flow and are designed according to the foregoing principles to produce flows having low Reynolds numbers, preferably below about 1, e.g., below about 0.1.

The devices of the preferred embodiment of this invention are capable of analyzing a sample of a size between about 0.01 microliters and about 20 microliters within a few seconds, e.g. within about three seconds. They also may be reused. Clogging is minimized and reversible. The sizes and velocities of 100 µm wide and 100 µm/s, for example, indicate a Reynolds number ($R_c$=plv/η) of about $10^{-2}$ so that the fluid is in a regime where viscosity dominates over inertia.

The magnitude of the pressure drop needed to obtain an average velocity, v, of a fluid with absolute viscosity, η, and density, ρ, through a circular channel (length, l, diameter, d) can be calculated from Poiseuille's Law (Batchelor, G. K., *An Introduction to Fluid Dynamics*, Cambridge Univ. Press 1967), $$\frac{P}{l} = \frac{32\eta v}{d^2} \tag{35}$$

Using v=100 µm/sec and d=100 µm, we get a pressure drop equivalent to about 0.3 mm of $H_2O$ per cm of channel length. Since Poiseuille's equation is strictly valid only for circular flow channels and the channels of this invention are substantially rectangular in cross-section it can be considered only as an approximate relation between the variables represented.

When a liquid is introduced into a device there is at first an effective pressure, $P_{eff}=P_o+P_{st}$, equal to the sum of the applied pressure, $P_o$, and a pressure due to the surface tension, $$P_{st} = \frac{\gamma \cos\Theta}{r}. \tag{36}$$

$P_{st}$ is a function of the surface tension of the fluid, γ, the contact angle of the fluid with the surface, Θ, and the radius of curvature of the fluid surface, r.

For hydrophilic surfaces, cos Θ is close to 1, and for small channels no applied pressure is needed to wet the device. This is referred to as "wetting by capillary action." However, once the device is completely wet, one has to worry about the surface tension at the exit area. In the device described in the example hereof, the radius of curvature of the fluid in the exit area was several millimeters, so that the pressure due to the surface tension was negligible With a channel width of 100 µm, $P_{st}$ is about 1 cm of $H_2O$, so surface tension on the exit channel is significant. However, using an etchant such as EPW F-Etch as described below, which attacks the <100> planes of silicon, means that the corners as etched are not as sharp as shown in the figures. This results in a gradual widening of the channel to about 1 mm which reduces the effect of the surface tension.

By adjusting the configuration of the channels in accordance with the principles discussed above to provide an appropriate channel length, flow velocity and contact time between the sample stream and the other stream, the size of the particles remaining in the sample stream and diffusing into the other stream can be controlled. The contact time required can be calculated as a function of the diffusion coefficient of the particle D and the distance d over which the particle must diffuse by $t=d^2/D$. Particles or molecules that have diffusion coefficients larger than D will diffuse into the other stream, and particles or molecules having a diffusion coefficient substantially smaller than D will not. If the diffusion coefficient of the larger particles is about ten times smaller than D, the other stream should be entirely free of the large particles.

For a given flow speed, some particles with relatively small diffusion coefficients, a straight channel cell system, preferably 5–50 mm in length, does not provide a long enough flow channel for diffusion to occur adequately. Typically, silicon microchips are 3 inches, 4 inches, 6 inches, or 8 inches in diameter. A straight channel etched into a microchip of such size can be no longer than the microchip diameter. Detection of analytes with relatively small diffusion coefficients, e.g. relatively large analytes or non-spherical analytes, preferably employs a convoluted flow channel. FIGS. 17 and 18 show two different channel geometries which allow for longer flow channels on a typical 3–4 inch silicon microchip.

In the channel cell system (T-sensor) of FIG. 17, the left and right streams, e.g., sample and indicator streams, have the same overall pathlength. If multiple measurements are taken in this embodiment, they should be taken along the vertical center line of the sensor so that both streams are flowing at the same flow speed and have had the same flow distance. In this embodiment, wherein the convoluted flow channel has a square wave shape, the streams flow at different speeds through the curves. Therefore, it may be preferable to use slower flow speeds than the speeds used in straight flow channels because the tight/narrow curves and sheer forces between the streams flowing at different speeds can cause zones in which laminar recirculation occurs. Laminar recirculation is not turbulence; the flow is still laminar and predictable. Nonetheless, laminar recirculation is not preferable and can be avoided by maintaining a Reynolds number below about 1.

The channel cell system (T-sensor) of FIG. 18 shows a coiled/spiral flow channel. In this geometry, four separate T-sensors each having a 220 mm long flow channel, can be fabricated on a single 3 inch microchip. Because the bending radius is larger in this geometry than in the square wave geometry, laminar recirculation is less likely to occur. The difference in relative flow speeds of the left and right streams (sample and indicator streams) is minimal, leading to less sheer stress between the two streams if the two streams have different viscosities. This channel geometry does, however, create different overall flow distances for the left and right streams.

FIGS. 19A and 19B illustrate channel cell systems (T-sensor devices) of this invention wherein the T-joint 158 is rounded. FIG. 19A shows a T-sensor similar to the one shown in FIG. 13, except that the T-joint 158 is rounded in FIG. 19A. FIG. 19B shows a viewport T-sensor similar to the one shown in FIG. 15, except that the T-joint 158 is rounded in FIG. 19B. A rounded T-joint is preferable because it helps prevent laminar recirculation in the T-joint which can occur at Reynolds number above about 1. A rounded T-joint is preferable also because it decreases the chance of contamination of the sample stream with the indicator stream, and vice versa.

The channel cell system of this invention can be used to measure concentration of an analyte as a function of distance (from the T-joint) rather than time. An increment of distance is proportional to an increment of time. With laminar flow and a known flow speed, an increment of distance can be converted to an increment of time.

Other methods for making kinetic measurements employ plotting concentration, or some physical property resulting from concentration, e.g., absorbance or fluorescence, versus time. The decrease in concentration of a starting material, or increase in concentration of a product, with time determines the kinetic rate constant for a reaction.

Figure 20:
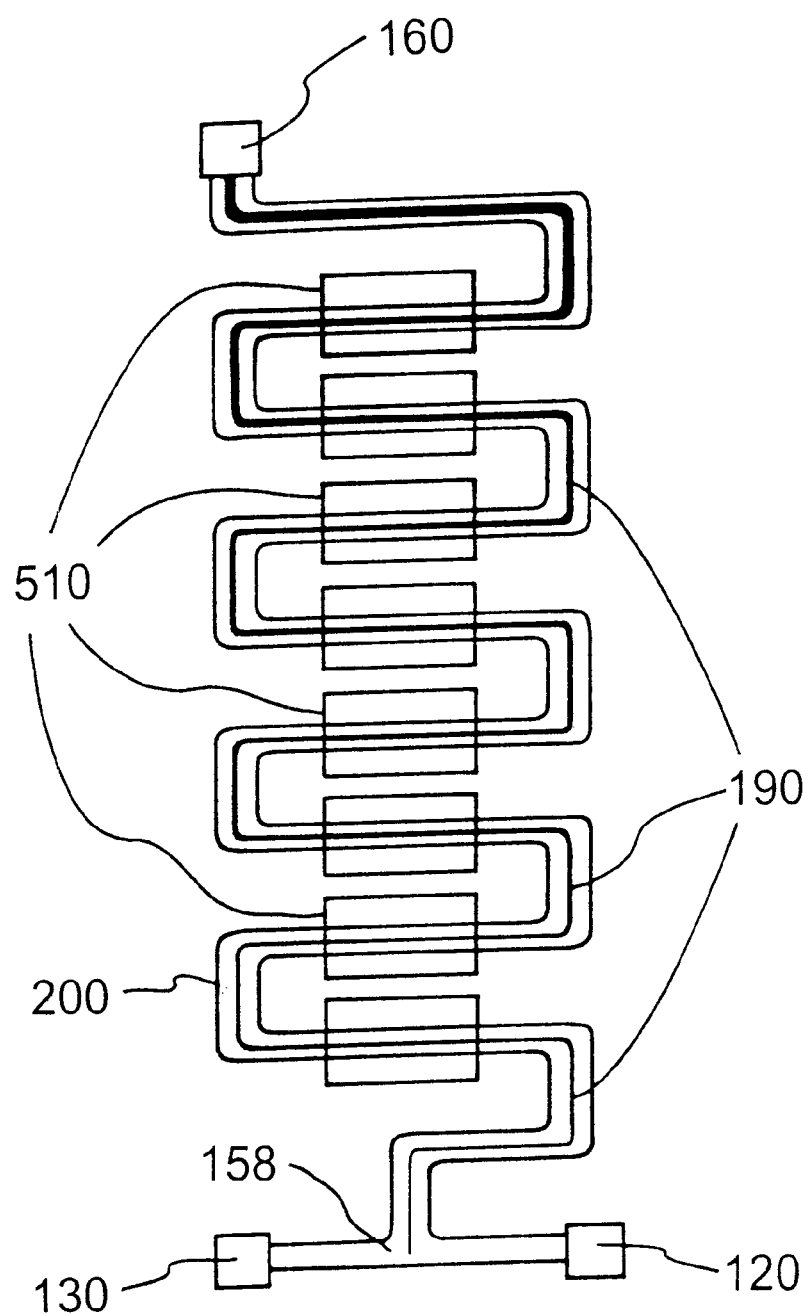
FIG. 20 shows a convoluted flow channel with a plurality of detection areas for making kinetic measurements as a function of distance.

The rate of, or rate constant for, a reaction can be determined using the T-sensor device of this invention. Detection, e.g., absorption or fluorescence measurements, can be performed at one or more analyte detection area. Referring to FIG. 20, a plurality of analyte detectors 510 can be positioned at various distances from the T-joint 158. Alternatively, one detector can be used to monitor the flow channel at various distances from the T-joint 158. FIG. 20 shows a square-wave/serpentine shaped flow channel. However, a T-sensor of any geometry which maintains laminar flow can be employed to make kinetic measurements, particularly according to the methods disclosed herein. A sample stream is introduced via sample stream inlet port 130 and an indicator stream is introduced via indicator stream inlet port 120. The two streams meet at T-joint 158. Analytes from the sample stream begin to diffuse into the indicator stream, and a measurable change, e.g., increase in fluorescence, occurs. A measurable change occurs as a result of analytes diffusing into the indicator stream, shown at analyte detection areas 190.

The intensity of fluorescence or absorbance in the analyte detection area and the width of the analyte detection area are measured at various distances from the T-joint 158. The intensity and width of the analyte detection area are a function of the concentration of the analyte being measured. As the analyte diffuses into the indicator stream, a change in color (i.e. change in optical absorbance) or fluorescence occurs in the analyte detection area. This optical change becomes more intense with increasing distance from the T-joint, because the analyte and the indicator have had a longer time to interact with each other. The width of the analyte detection area also increases with increasing distance from the T-joint. Two independent causes lead to this increase in width. First, the analytes diffuse farther with increasing time, and therefore with increasing distance. Second, the more the interaction between the analyte and indicator has progressed, the greater the absorbance or fluorescence at the analyte detection area. Hence, absorbance or fluorescence can be detected at a greater width in the analyte detection area.

Referring to FIG. 20, the analyte detection area 190 becomes wider and more intense with increasing distance from the T-joint 158.

Using the device and methods of this invention, a rate constant for a reaction can be determined with as few as one measurement, e.g., fluorescence at a certain distance from the T-joint. As is known in the art, increasing the number of measurements leads to increased accuracy of the kinetic rate constant calculated from such measurements.

Figure 21A:
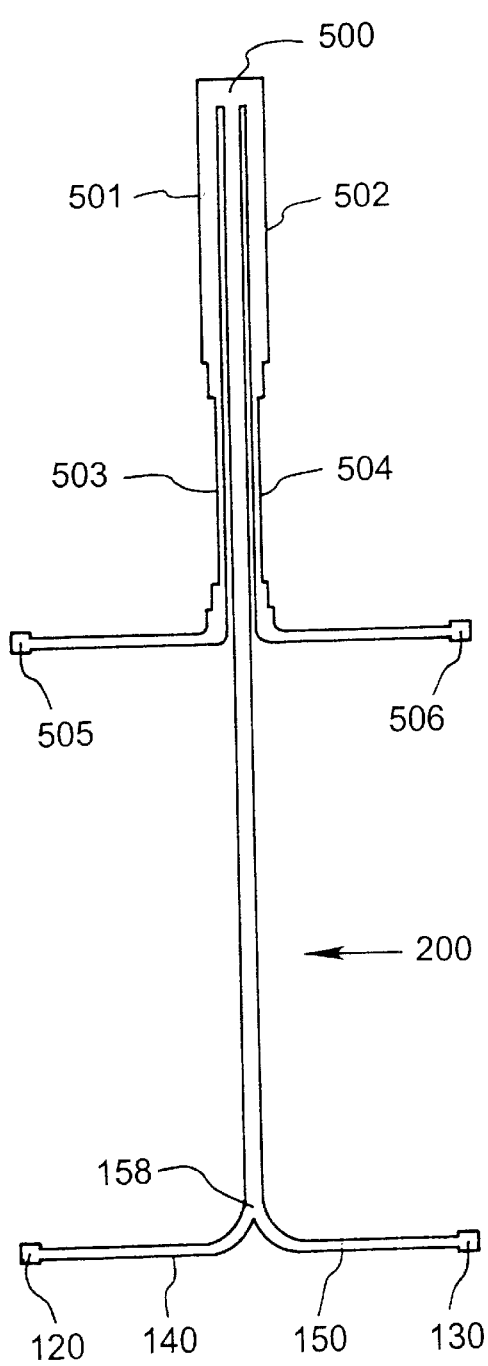
FIGS. 21A–21C, shows embodiments with branching flow channels for dual detection of both dissolved and undissolved analytes.
Figure 21B:
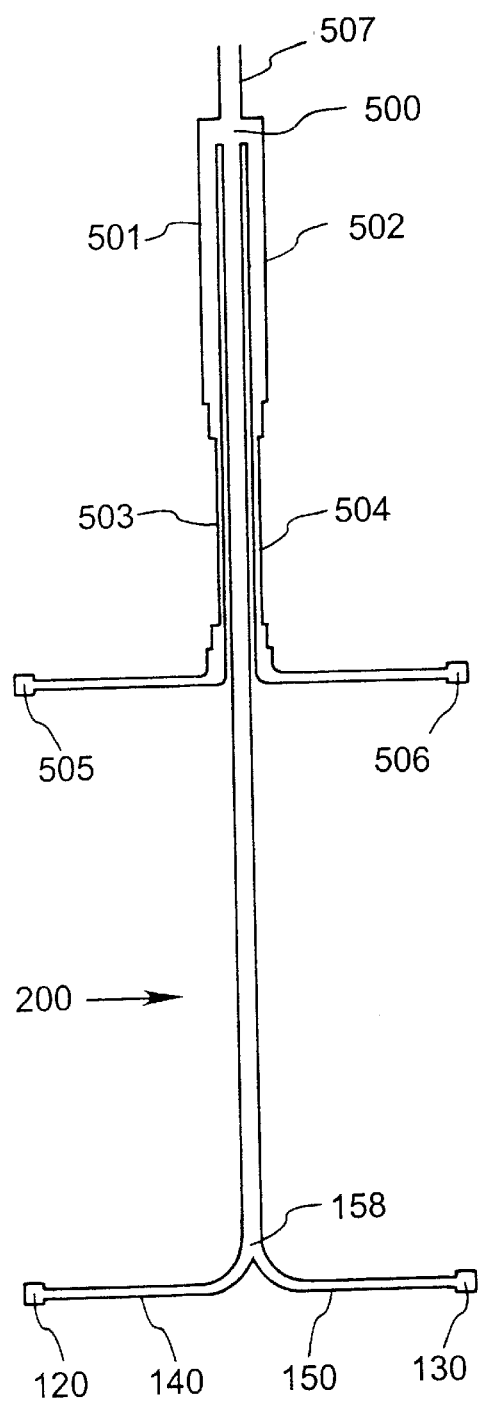

In another embodiment, the T-sensor channel cell system of this invention can comprise branching flow channels 501 and 502 as illustrated in FIG. 21A. The sample containing small molecules of interest is brought into the device through sample stream inlet port 130, from whence it flows into sample stream inlet channel 150. An indicator stream is brought into indicator stream inlet port 120, from whence it flows into indicator stream inlet channel 140. The two streams flow parallel to one another in laminar flow, and small molecules (analytes) from the sample stream diffuse into the indicator stream. Branching flow channels as used herein refer to flow channels in fluid connection with the flow channel 200. A W-joint 500 as shown in FIGS. 21A and 21B may be used to correct the branching flow channels 501 and 502 with flow channel 200. Branching flow channels allow for detection of both undissolved and dissolved particles. A detector, preferably positioned above or below the device, monitors the flow channel 200 and v-grooves 503 or 504. This dual detection embodiment can detect dissolved and undissolved particles in the flow channel 200 as well as undissolved particles flowing in single file fashion in the v-groove(s). Particle detection can be performed by standard optical techniques, e.g., imaging, light scattering, or spectroscopy, as the particles flow through one or both of the v-grooves 503 or 504, which are in fluid connection with branching flow channels 501 and 502, respectively. Branching flow channels 501 and 502 are in fluid connection with exit ports 505 and 506, respectively.

For example, in this embodiment a sample, e.g., whole blood, can be introduced via sample stream inlet port 130 from whence it flows into sample stream inlet channel 150 and a buffered solution containing reporter beads can be introduced via indicator stream inlet port 120 from when it flows into indicator stream inlet channel 140. The sample and indicator stream flow parallel to each other in laminar flow in flow channel 200. Small analytes in the sample, e.g., protons, diffuse into the indicator stream. Referring to FIG. 21A, the sample flows into branching flow channel 502 and then into v-groove 503, through which particles, e.g., red and white blood cells, flow in single file fashion. At the same time, the reporter beads flow into branching flow channel 502 and then into v-groove 503, through which the beads flow in single file fashion. An optical detector, preferably positioned above or below the device simultaneously monitors the two streams in flow channel 200 and the undissolved sample particles in v-groove 504 and beads in v-groove 503, the beads being indicators of dissolved sample analytes.

Alternatively, the indicator stream can include a dissolved indicator dye which is monitored with the monitoring of the undissolved sample particles when this embodiment of the present device is employed. A dissolved indicator dye does not need to be monitored in a v-groove. Hence, both branching flow channels need not be connected to v-grooves, as illustrated in FIG. 21C.

Another example of the dual detection embodiment of this invention is the following. A sample of whole blood can be monitored in a v-groove channel to detect the number of white blood cells. Then the same sample flows into a T-sensor in fluid connection with the v-groove channel. In the T-sensor the white blood cells react with fluorescent reporter beads tagged with an antibody. Then the sample flows into another v-groove channel in fluid connection with the T-sensor. In this v-groove channel the white blood cells are identified by fluorescence.

The T-sensor channel system of the present invention can further comprise a waste port 507, as illustrated in FIG. 21B. To insure that only sample stream enters branching flow channel 502, and that only indicator stream enters branching flow channel 501, a portion of each stream can be diverted to a waste port 507. The waste port is in fluid connection with the flow channels at the W-joint to divert a portion of each stream to a waste outlet.

Figure 21C:
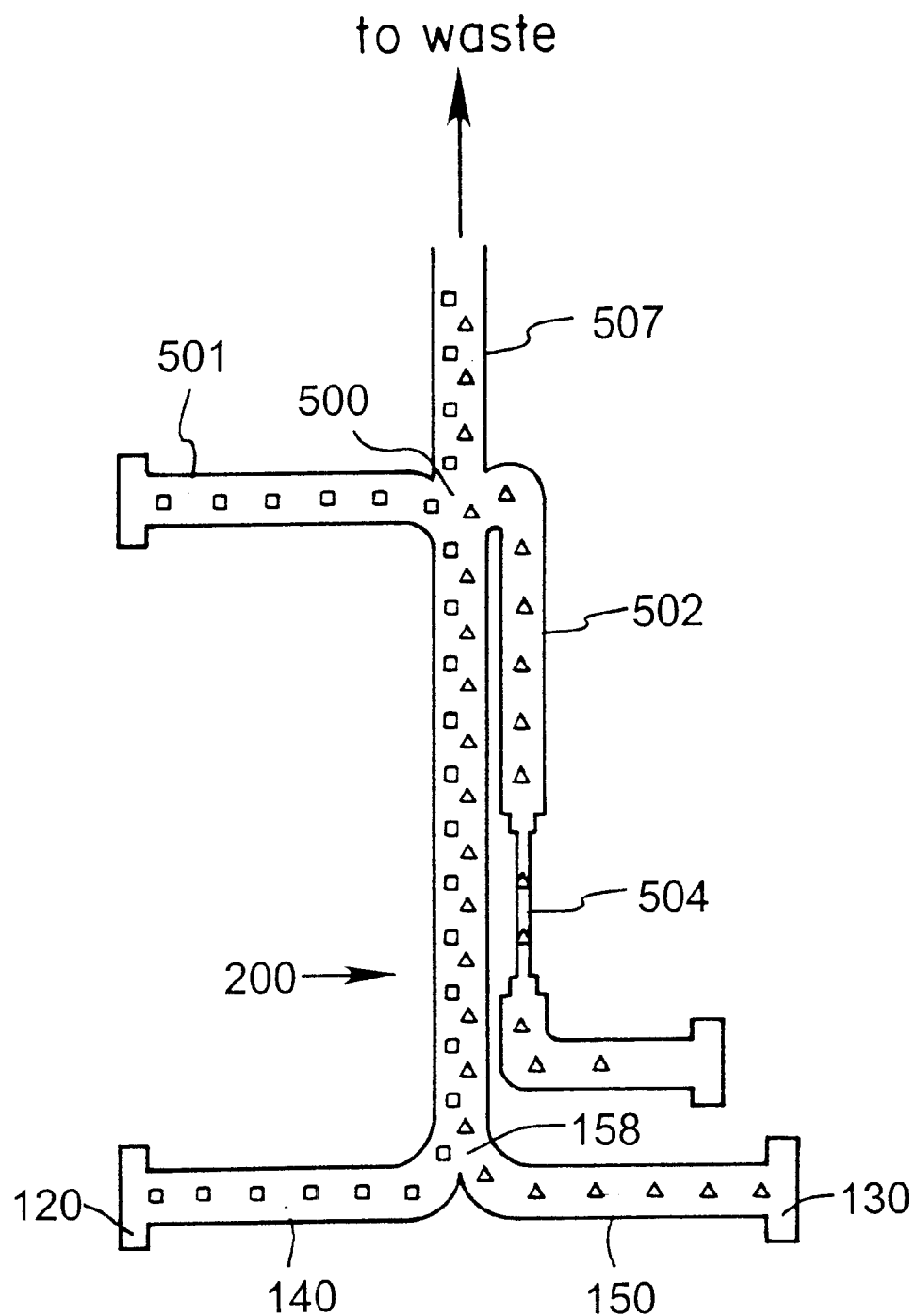

FIG. 21C illustrates sample stream (represented by x) and indicator stream (represented by squares) flowing through the channel system of this invention comprising branching flow channels and a waste port. FIG. 21C further illustrates that the branching flow channels do not have to loop back and run parallel to the flow channel 200. Branching flow channels can connect to the flow channel 200 in any angle desired. In order to monitor the flow through the various channels simultaneously and with one detector it is preferable th at the branching flow channels connect with the flow channel 200 at an angle which allows for such monitoring.

Detection of dissolved and undissolved particles in one device employing this embodiment is economically advantageous, as measurements can be performed with only one set of pumps and one detector.

Another means for detecting undissolved particles in single file flow employs a sheath flow module. A sample can first flow through a flow channel of a T-sensor where the sample reacts with reporter beads, e.g., an analyte in the sample diffuses into an indicator stream containing reporter beads. The fluid containing reporter beads can then flow into a sheath flow module in fluid connection with the T-sensor flow channel. In the sheath flow module the beads are focused so that they flow in single file fashion for detection.

Figure 22A:
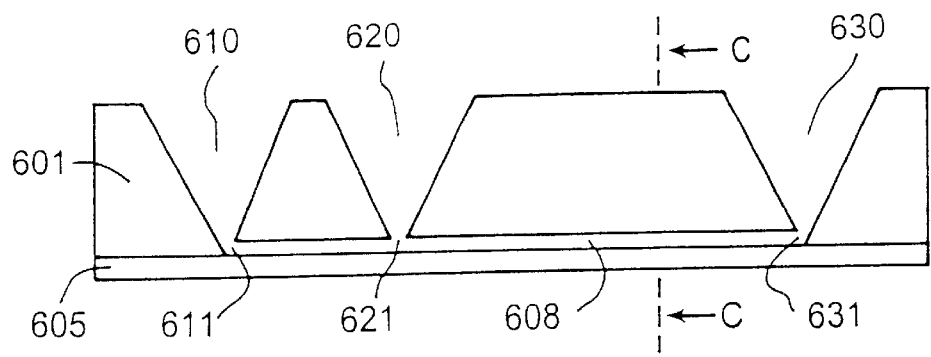
FIGS. 22A–22C, shows a sheath flow module.
Figure 22B:
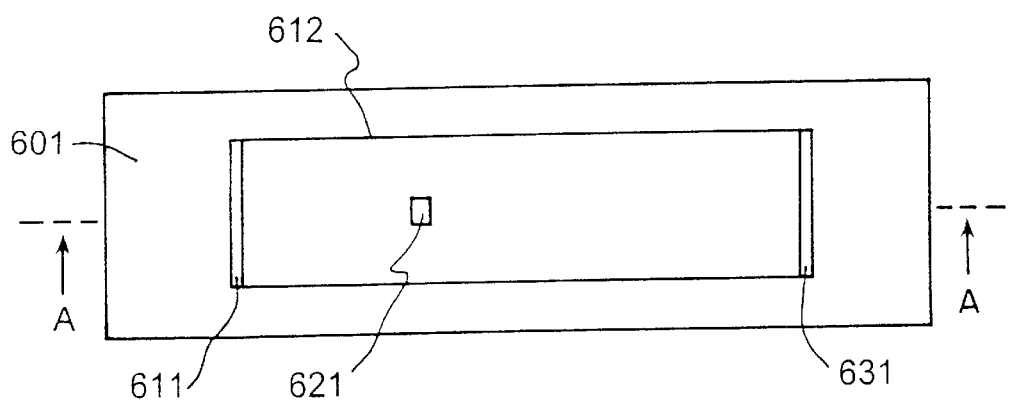
Figure 22C:
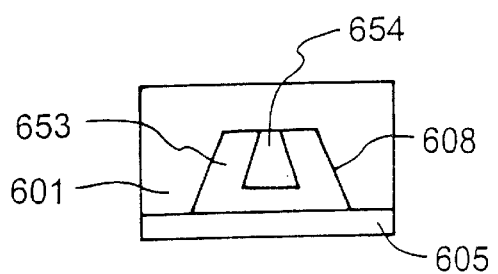

As with the v-groove channel, the order of the sheath flow module and the T-sensor can be reversed, i.e., the fluids can flow first through the sheath flow module and then through the T-sensor. FIG. 22A is a lengthwise section through the center of a flow module, as described in U.S. patent application Ser. No. 08/823,747 filed Mar. 26, 1997, now U.S. Pat. No. 6,159,739. Plate 601 is machined, molded or etched to form the flow channel. The plate can be selected from the following which include, but are not limited to, silicon wafers, plastics, e.g., polypropylene, and casting materials. Techniques for etching silicon wafers and molding and machining plastics are well-known in the art. A laminar flow channel 608 is formed in a flat plane of the plate. A first inlet 610 passes through the plate at the upstream end of the channel and joins the flow channel at first inlet junction 611. An outlet 630 passes through the plate at the downstream end of the channel and joins the flow channel at outlet junction 631. A second inlet 620 passes through the plate between the first inlet and the outlet and joins the flow channel at second inlet junction 621, which is narrower than the first inlet junction. A second plate 605 is sealed to the flat plane of the first plate, thereby forming one side of the laminar flow channel. A view of the channel surface is illustrated in FIG. 22B. The relative widths of the inlet junctions are shown, as well as the edge 612 of the flow channel 608. The second inlet junction 621 is narrower than the first inlet junction 611. Referring again to FIGS. 22A and 22B, a sheath fluid is introduced into the flow channel 608 via the first inlet 610 and flows through the flow channel toward the outlet 630. A center fluid is introduced via the second inlet 620, preferably at lower pressure and speed than the sheath fluid. FIG. 22C is a cross section of the flow channel of FIGS. 22A and 22B, illustrating the sheath flow attained in one embodiment of the present invention. In this embodiment flow channel 608 is trapezoidal. A center fluid 654, injected from inlet 620, is surrounded on both sides (left and right) and on top by a sheath fluid 653.

Figure 23:
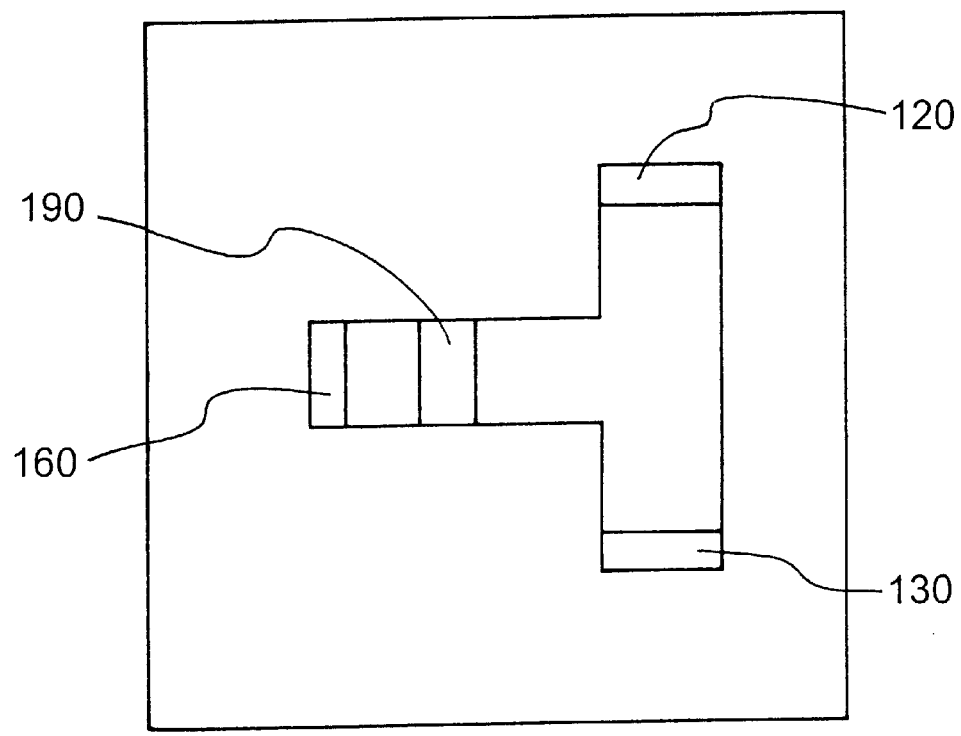
FIG. 23 shows a T-sensor in which the analyte detection area is etched all the way through the width of the substrate plate.

As discussed above, forming the channel system in a reflective material allows for optical measurements by reflection. Alternatively, optical measurements by transmission can be performed in the embodiment described next. A T-sensor channel system can be etched all the way through a substrate plate, e.g., a silicon microchip or other slab of material. The entire channel system can be etched all the way through, and therefore transect, that is, extend through the width of, the substrate plate. Alternatively, only that part of the channel system comprising the analyte detection area 190 can be etched all the way through, and therefore extend through the width of, the substrate plate, as shown in FIG. 23. Indicator stream inlet port 120, sample stream inlet port 130, and exit port 160 are shown also. An optically transparent plate, e.g., a cover plate, is sealed to both sides of the microchip. If only part of the channel system is etched all the way through the microchip, then the transparent plate need cover only that part of the microchip.

As in the other embodiments of this invention, the dimensions of the device are chosen so that laminar flow is maintained. In this embodiment, if a silicon microchip is etched by anisotropic EPW etching, it is preferable to use a thin microchip so that the channel diameters can be kept small enough to maintain laminar flow. The anisotropic EPW etching creates channels which are wider at the top than at the bottom of the channel. Etching all the way through a microchip can create a channel which is undesirably wide at the top and therefore with an undesirably large channel diameter. Undesirably large channel diameters may not maintain laminar flow. Preferable widths of a thin microchip are between 100 and 300 microns, and more preferably between 100 and 200 microns. Alternatively, other methods of etching silicon, e.g., reactive ion etching, can be used to keep channel diameters small enough to maintain laminar flow. Other materials, e.g., plastics, which are machined or molded to form the channel system need not necessarily be thin to keep channel diameters small.

A microchip can be made thinner by etching prior to formation of the channel system therein. An uncoated microchip, that is a microchip with no photoresist on it, can be made thinner by submerging it in etching solution. A channel system, or at least the analyte detection area, can then be etched all the way through the microchip.

Alternatively, a T-sensor channel system which maintains a low Reynolds number, i.e. laminar flow, can be formed wherein the depth of the channel is greater than the width. However, because the flow speed is parabolic with respect to the channel width, i.e., it is fastest in the center of the channel and approaches zero at the walls, it is preferable that the channel dimensions are such that diffusion from top to bottom and bottom to top counteracts this parabolic flow speed profile. Increasing the depth of the flow channel decreases the effect of diffusion from top to bottom and bottom to top.

Numerous embodiments besides those mentioned herein will be readily apparent to those skilled in the art and fall within the range and scope of this invention. All references cited in this specification are incorporated in their entirety by reference herein. The following examples illustrate the invention, but are in no way intended to limit the invention.

EXAMPLES

Example 1

In a preferred process for making a device of this invention, a 1 $\mu$m thick wet thermal oxide is grown in a 3" silicon wafer. This oxide is photolithographically patterned with the flow channels and etched to a depth of 60 nm. The wafer is recoated with photoresist and patterned with the through-hole connections. The oxide is completely removed from this pattern. EDP etching is done to etch completely through the wafer (approximately 400 $\mu$m). An oxide etch is performed to uniformly remove 400 nm of oxide from the wafer. The flow channels are etched into the silicon approximately 10 $\mu$m deep. Finally the wafer is anodically bonded to a 3" disk of Pyrex glass.

The following example demonstrates the use of diffusion based extraction to separate diffusing constituents from a particle laden sample stream using micron sized devices microfabricated in silicon. See FIG. 2. Fluorescein dye was extracted from a sample stream containing 0.5 $\mu$m fluorescent polystyrene spheres and fluorescein dye. Operation was demonstrated with zero contamination of the extraction stream by fluorescent spheres. The device had a total extraction channel fluid volume of approximately 1 femtoliter. The example demonstrates that separation is possible at the femtoliter scale given appropriate attention to precise flow stream regulation. Further, it demonstrates that efficient separation is possible in extraction channels with aspect ratios much less than 50 and in channels with diffusion direction dimension much less than 100 $\mu$m. The extraction device with w/d<<50, d<100 $\mu$m demonstrated the effectiveness of a micro-fluidic system fabricated using silicon microfabrication technology and the essential attributes of ultra-low Reynolds number flow.

A two mask level process was needed to fabricate the device. The first level defined connection ports, which were etched completely through the wafer to the rear side of the silicon. The second level defined the fluid transport channels.

Four-inch chrome masks were made to our specifications by Photo Sciences, Inc. (Torrance, Calif.) and 3" wafers ({100}, n-type) with 500 nm of $SiO_2$ grown on them.

Wafers were cleaned in a Piranha bath ($H_2SO_4$ and $H_2O_2$) (2:1) before processing. A primer (HMDS spun on at 3000 rpm) was used to enhance photoresist adhesion. About one $\mu$m of AZ-1370-SF (Hoechst) photoresist was deposited by spin coating (3000 rpm), and this was followed by a soft bake (30 min at 90° C.).

A contact aligner was used to align and expose wafers. Exposure time was varied to yield best results. No post-exposure bake was done. Wafers were developed in AZ-351 (diluted 4:1) (Hoechst) for one minute, and rinsed in DI water. Blue tack tape (Semiconductor Equipment Corporation, Moorpark, Calif.) was applied to the backsides of the wafers to protect the oxide from the oxide etch.

The wafers were immersed in a buffered oxide etch (BOE, 10:1 HF (49%) and $NH_4F$ (10%)) for eleven minutes to completely etch away the unprotected oxide. The blue tack tape was removed by hand, and the photoresist was removed in an acetone rinse.

Silicon etching was done in a mixture of ethylenediamine, pyro-catechol, and water (EPW F-etch) set up in a reflux boiling flask. This etch attacks the {100} planes of silicon at a rate of about 100 $\mu$m an hour. Fluid attachment ports were etched in the first step. Flow channels between fluid ports and the filter region were etched in the second step. The barrier was etched in the final step.

After final processing the wafers were once again cleaned in a Piranha bath and rinsed in DI water. They were then diced into individual devices.

We used anodic bonding (Wallis, G. and Pomerantz, D. I. (1969), J. Appl. Physics 40:3946–3949) to attach Pyrex glass to the silicon devices. We obtained 1" square pieces of Pyrex glass (100 $\mu$m thickness) from Esco Products Inc. (Oak Ridge, N.J.). First, the silicon and Pyrex glass were immersed in a solution of $H_2O$, $NH_4OH$, and $H_2O$ (1:4:6) heated to 50° C. This process removes any organic matter on the surfaces and also makes the surfaces hydrophilic. After 20 minutes in this solution, the silicon and Pyrex were rinsed with DI water and dried. Anodic bonding was done at 400° C. with 400 V applied between the glass and the silicon.

Fluid connections were made to ports on the back side of the wafer. A glass tube (⅛" inner diameter, about 3 cm long) was epoxied around the fluid ports. The flow was driven by a pressure difference between the entrance ports and the exit port. This pressure difference, less than 3 cm of $H_2O$, is enough to induce a flow velocity of greater than 100 $\mu$m per second.

Observations were made on a Zeiss ICM-405 inverted microscope and recorded with a Dage silicon intensified target camera. First, the device was wet with isopropyl alcohol and any trapped air bubbles were removed by applying approximately 70 kPa of pressure. Then a mixture of water, carboxyfluoroscein (Molecular Probes), and 0.5 $\mu$m diameter fluorescent balls (Duke Scientific) was introduced into one of the fluid entrance ports. Pure water was introduced at the other entrance port. All the 0.5 $\mu$m spheres flowed to the exit channel for the sample stream. The dye diffused throughout the extraction channel and some flows out with the product stream.

Example 2

Fabrication of Diffusion Analysis Channel Cell

A two-mask level process was used to fabricate a channel cell of this invention on a silicon wafer. The channel cell had a flow channel 400 micrometers wide and 20 mm long. The "branches" or crossbar of the "T" comprising the inlet channels was a groove 30 mm long and 200 micrometers wide. Channel depth was 50 micrometers.

The first mask level defined the inlets and outlet ports, which were etched completely through the wafer to the rear side of the silicon. The second level defined the fluid transport channels.

Four inch chrome masks were made to these specifications by Photo Sciences, Inc. (Torrance, Calif.) and 3" wafers ({100}, n-type) with 500 nm of $SiO_2$ grown on them were used.

Wafers were cleaned in a Piranha bath ($H_2SO_4$ and $H_2O_2$) (2:1) before processing. A primer (HMDS spun on at 3000 rpm) was used to enhance photoresist adhesion. About one $\mu$m of AZ-1370-SF (Hoechst) photoresist was deposited by spin coating (3000 rpm), and this was followed by a soft bake (30 min at 90° C.).

A contact aligner was used to align and expose wafers. Exposure time was varied to yield best results. No post-exposure bake was done. Wafers were developed in AZ-351 (diluted 4:1) (Hoechst) for one minute and rinsed in DI water. Blue tack tape (Semiconductor Equipment Corporation, Moorpark, Calif.) was applied to the backsides of the wafers to protect the oxide from the oxide etch.

The wafers were immersed in a buffered oxide etch (BOE, 10:1 HF (49%) and $NH_4F$ (10%)) for eleven minutes to completely etch away the unprotected oxide. The blue tack tape was removed by hand, and the photoresist was removed in an acetone rinse.

Silicon etching was done in a mixture of ethylene-diamine, pyro-catechol, and water (EPW F-etch as described in Reisman, A., et al. (1979) J. Electrochem. Soc. 126:1406–1415) set up in a reflux boiling flask. This etch attacks the {100} planes of silicon at a rate of about 100 $\mu$m an hour. Fluid attachment ports were etched in the first step for about three hours. Photoresist was again applied, and the mask containing flow channels between fluid ports and the barrier region was exposed. The wafers were developed and etched in this second step for about one hour.

After final processing, the wafers were once again cleaned in a Piranha bath and rinsed in DI water. They were then diced into individual devices about 1 cm by 1 cm.

Anodic bonding according to Wallis, G. and Pomerantz, D. I (1969) J. Appl. Physics 40:3946–3949, was used to attach Pyrex glass to the silicon devices. One inch square pieces of Pyrex glass (100 $\mu$m thickness) from Esco Products Inc. (Oak Ridge, N.J.) were used. First, the silicon and Pyrex glass were immersed in a solution of $H_2O_2$, $NH_4OH$, and $H_2O$ (1:4:6) heated to 50° C. This process removes any organic matter on the surfaces and also makes the surfaces hydrophilic. After 20 minutes in this solution, the silicon and Pyrex were rinsed with DI water and dried. Anodic bonding was done at 400° C. with 400 V applied between the glass and the silicon.

Example 3

Fluorescence Color changes with pH

Five 0.01 M HEPES Buffer solutions, with pH 7.2, 7.4, 7.6, 7.8 and 8.0 were prepared from analytical grade chemicals (Aldrich). The resulting solutions were used consecutively as sample streams. The analyte in question in this experiment is $H^+$ or $OH^-$. 1 mg of the fluorescent pH indicator dye carboxy-SNAFL 2 (Molecular Probes, Eugene, Oreg.), was dissolved in 2 ml of DMSO (0.9%, Aldrich). 0.1 ml of this solution was mixed with 1 ml of a 0.0001 M HEPES Buffer of pH 7.0. The resulting solution was used as the indicator stream.

The T-sensor channel cell was attached to the stage of a microscope so that the joint of the T-sensor was in the view field of the objective. The inlet ports and the outlet port were connected to injector loops and to upright tubes which were filled with water so that there was a pressure difference of 30 mm water column between the inlet ports and the outlet port. Both inlet ports were exposed to identical pressure so that the two streams joined in the middle of the T-joint, and were flowing parallel to the outlet port. One injector loop was filed with indicator dye solution, the other loop was filled with one of the sample solutions. The loops contained enough volume to operate the device for roughly one hour.

After both injection loops were allowed to flow into the T-sensor, and after 1 min of equilibration and flushing time, photographs were taken through a camera attachment on the microscope. The excitation filter center wavelength was 480 nm, the emission filter was a longpass 510 nm filter.

The experiment yielded photographs in which the color of the analyte detection area between the indicator stream and the sample stream was a function of the pH of the sample stream. The color changed from red over orange to yellow as the pH decreased from 8.0 to 7.2. Computer-enhanced images showed the color of the indicator stream per se to be yellow, and the analyte detection area between the streams to range from red to orange, whereas the colorless ample stream appeared black. By color mapping, numeric values are assigned to the different colors which are used to calibrate the system. Alternatively, light intensity change is measured at two wavelengths, thereby measuring the decrease of the red portion and the increase of the yellow portion of the spectrum with decreasing pH.

Example 4

Kinetic Measurements as a Function of Distance

Alkaline phosphatase in serum and 0.1 M p-nitrophenol phosphate (PNPP)(weakly yellow) in 0.1 M HEPES buffer, pH 7.40, were injected into a T-sensor device. The alkaline phosphatase catalyzed the reaction of PNPP to p-nitrophenol (strongly yellow) and phosphate. The formation, (and rate thereof), of p-nitrophenol was detected by an increase in yellow color. The rate of change of yellow color intensity as a function of distance from the T-joint was a function of enzyme concentration, enabling calculation of a rate constant.

The invention has been illustrated with specific embodiments; however, as will be appreciated by those skilled in the art, various substitutions can be made for the specific elements and process steps disclosed herein. The invention is limited only by the scope of the appended claims.

What is claimed is:

1. A microfluidic system comprising:
   (a) a plurality of inlets;
   (b) a microfluidic flow channel in fluid communication with said inlets;
   (c) at least two outlets in fluid communication with said microfluidic flow channel; and
   (d) flow control means connected to all but one of said inlets and said outlets.

2. The microfluidic system of claim 1 comprising means for controlling fluid flow through each of said outlets.

3. The microfluidic system of claim 1 having two inlets.

4. The microfluidic system of claim 1 having two outlets.

5. The microfluidic system of claim 1 having at least three outlets.

6. The microfluidic system of claim 1 having at least four outlets.

7. The microfluidic system of claim 1 having at least six inlets and at least six outlets.

8. The microfluidic system of claim 1 wherein said means for controlling fluid flow are connected to all of said inlets.

9. The microfluidic system of claim 1 wherein said means for controlling fluid flow are connected to all of said outlets.

10. The microfluidic system of claim 1 wherein said means for controlling fluid flow are pressure control means.

11. The microfluidic system of claim 1 wherein said pressure control means is selected from the group consisting of include columns of water, electroendoosmotic forces, optical forces, gravitational forces and surface tension forces.

12. The microfluidic system of claim 1 wherein said flow channel contains at least a first and second fluid stream in side-by-side laminar flow.

13. The microfluidic system of claim 12 wherein particles contained in said first fluid stream diffuse into said second fluid stream within said channel.

14. A microfluldic system comprising:
   (a) a plurality of inlets;
   (b) a microfluidic flow channel in fluid communication with said inlets;
   (c) at least three outlets in fluid communication with said microfluidic flow channel; and
   (d) flow control means connected to all but one of said inlets and said outlets.

15. The system of claim 14 having at least four outlets.

16. The system of claim 14 having at least six inlets and at least six outlets.

17. The microfluidic system of claim 14 wherein said means for controlling fluid flow are connected to all of said inlets.

18. The microfluidic system of claim 14 wherein said means for controlling fluid flow are connected to all of said outlets.

19. The microfluidic system of claim 14 wherein said means for controlling fluid flow are pressure control means.

20. The microfluidic system of claim 19 wherein said pressure control means is chosen from the group consisting of columns of water, electroendoosmotic forces, optical forces, gravitational forces and surface tension forces.

21. The microfluidic system of claim 14 wherein said flow channel contains at least a first and second fluid stream in side-by-side laminar flow.

22. The microfluidic system of claim 21 wherein particles contained in said first fluid stream diffuse into said second fluid stream within said channel.

23. A method for creating a fluid interface between two or more streams flowing within a microfluidic channel comprising:
   (a) providing an inlet for each of said streams in fluid communication with said inlets;
   (b) providing at least two outlets in fluid communication with said microfluidic flow channel;
   (c) providing flow control means at all but one of said inlets and said outlets;
   (d) simultaneously flowing each of said streams through an inlet into said microfluidic flow channel;
   (e) allowing said streams to flow in side-by-side laminar flow within said channel; and
   (f) removing said streams through the at least two outlets.

24. The method of claim 23 wherein said streams are of equal volume.

25. The method of claim 23 wherein said streams are of equal flow rate.

26. The method of claim 23 comprising forming a fluid barrier between said streams.

27. The method of claim 26 wherein said fluid barrier is formed by flowing a greater volume of one stream than the other stream into said channel.

28. The method of claim 26 wherein the fluid barrier is formed by allowing a lesser volume of one stream that the other to exit said channel.

29. The method of claim 23 wherein said streams comprise a particle-containing stream and a particle-receiving stream, and particles contained in the particle-containing stream are allowed to diffuse into the particle-receiving stream.

* * * * *